US012788505B2

(12) United States Patent
Konduri et al.

(10) Patent No.: US 12,788,505 B2
(45) Date of Patent: Nov. 10, 2026

(54) RELAXATION TENSION MONITORING AND HOMING OF MEDICAL INSTRUMENTS

(71) Applicant: Auris Health, Inc., Santa Clara, CA (US)

(72) Inventors: Shyamprasad Konduri, Daly City, CA (US); Michael David Leslie, San Francisco, CA (US); Chauncey F. Graetzel, Palo Alto, CA (US)

(73) Assignee: Auris Health, Inc., Santa Clara, CA (US)

( * ) Notice: Subject to any disclaimer, the term of this patent is extended or adjusted under 35 U.S.C. 154(b) by 325 days.

(21) Appl. No.: 18/421,413

(22) Filed: Jan. 24, 2024

(65) Prior Publication Data

US 2024/0245472 A1 Jul. 25, 2024

Related U.S. Application Data

(60) Provisional application No. 63/441,128, filed on Jan. 25, 2023.

(51) Int. Cl.
*A61B 34/30* (2016.01)
*A61B 34/00* (2016.01)

(52) U.S. Cl.
CPC .............. *A61B 34/30* (2016.02); *A61B 34/71* (2016.02); *A61B 2034/301* (2016.02); *A61B 2034/306* (2016.02)

(58) Field of Classification Search
CPC ......... A61B 34/30; A61B 34/71; A61B 34/37; A61B 2034/715
See application file for complete search history.

(56) References Cited

U.S. PATENT DOCUMENTS

| | | | | |
|---|---|---|---|---|
| 2018/0080533 | A1* | 3/2018 | Awtar | A61B 34/71 |
| 2019/0000566 | A1* | 1/2019 | Graetzel | A61B 34/71 |
| 2020/0038127 | A1 | 2/2020 | Chaplin et al. | |
| 2020/0138532 | A1 | 5/2020 | Podolsky et al. | |
| 2021/0196415 | A1 | 7/2021 | Castillo et al. | |
| 2025/0303554 | A1* | 10/2025 | Yang | A61B 34/71 |

FOREIGN PATENT DOCUMENTS

JP 2022185651 A 12/2022

OTHER PUBLICATIONS

International Search Report for Appl. No. PCT/IB2024/050663, dated Apr. 26, 2024, 3 pages.
Written Opinion for Appl. No. PCT/IB2024/050663, dated Apr. 26, 2024, 3 pages.
Notification, International Preliminary Report on Patentability from PCT Application No. PCT/IB2024/050663, dated Aug. 7, 2025, 5 pages.

* cited by examiner

*Primary Examiner* — William J Levicky
(74) *Attorney, Agent, or Firm* — Paradice & Li LLP

(57) ABSTRACT

A robotic system includes an end effector comprising one or more drive outputs configured to cause articulation of an elongate shaft of an instrument coupled to the end effector, a memory, and a memory storing computer-executable instructions, that when executed, cause the processor to: determine a pulley rotation, when applied to a pulley coupled to the elongate shaft by the end effector, expected to articulate the elongate shaft to a desired articulation, drive the one or more drive outputs based at least in part on the pulley rotation, monitor tension on one or more pull wires coupled to the pulley, and controlling the one or more drive outputs based at least in part on the tension.

20 Claims, 18 Drawing Sheets

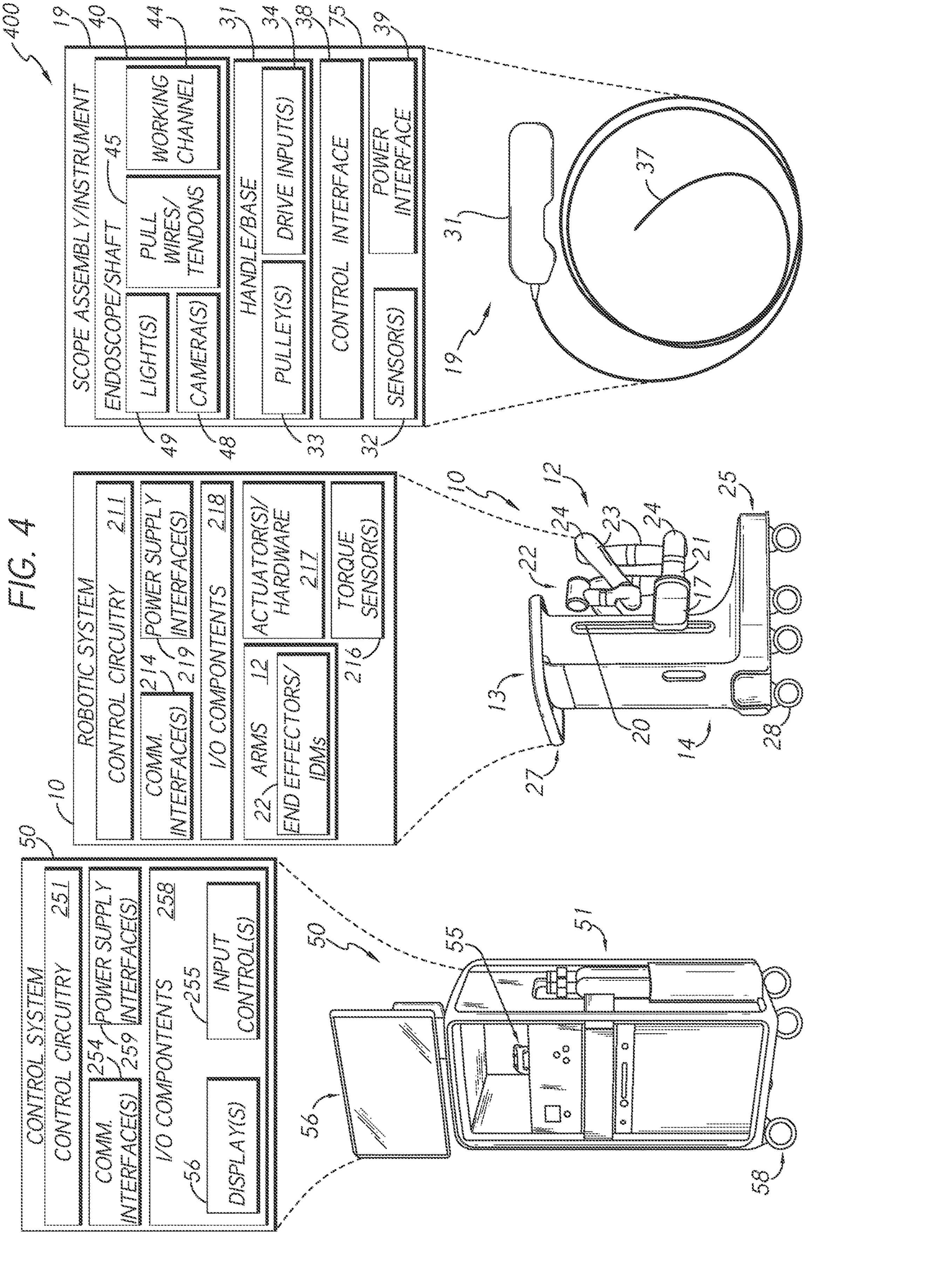
FIG. 4
400
SCOPE ASSEMBLY/INSTRUMENT
ENDOSCOPE/SHAFT
LIGHT(S)
CAMERA(S)
PULL WIRES/ TENDONS
WORKING CHANNEL
HANDLE/BASE
PULLEY(S)
DRIVE INPUT(S)
CONTROL INTERFACE
SENSOR(S)
POWER INTERFACE
ROBOTIC SYSTEM
CONTROL CIRCUITRY 211
COMM. INTERFACE(S)
POWER SUPPLY INTERFACE(S)
I/O COMPONTENTS 218
ARMS 12
END EFFECTORS/ IDMs
ACTUATOR(S)/ HARDWARE 217
TORQUE SENSOR(S)
CONTROL SYSTEM
CONTROL CIRCUITRY 251
COMM. INTERFACE(S)
POWER SUPPLY INTERFACE(S)
I/O COMPONTENTS 258
INPUT CONTROL(S)
DISPLAY(S)

RELAXATION TENSION MONITORING AND HOMING OF MEDICAL INSTRUMENTS

RELATED APPLICATION(S)

This application claims priority to U.S. Provisional Patent Application Ser. No. 63/441,128, filed on Jan. 25, 2023 and entitled RELAXATION TENSION MONITORING AND HOMING OF MEDICAL INSTRUMENTS, the complete disclosure of which is hereby incorporated by references in its entirety.

BACKGROUND

Field

The present disclosure relates to robotic medical systems.

Description of Related Art

Certain robotic medical procedures can involve the use of shaft-type instruments, such as endoscopes, which may be inserted into a patient through an orifice (e.g., a natural orifice) and advanced to a target anatomical site. Such medical instruments can be articulatable, such that the tip and/or other portion(s) of the shaft can deflect in one or more dimensions using robotic controls.

SUMMARY

Described herein are systems, devices, and methods to facilitate the instrument articulation control in connection with certain medical procedures. In particular, systems, devices, and methods in accordance with one or more aspects of the present disclosure can facilitate the monitoring of shaft articulation and/or shaft articulation pull wire tension and tensioning. For example, pull wire tensioning for the purpose of articulating an instrument shaft can be mitigated in certain respects in response to determined/detected articulation and/or tension conditions.

In some aspects, the techniques described herein relate to a robotic system including: an end effector including one or more drive outputs configured to cause articulation of an elongate shaft of an instrument coupled to the end effector; a processor; and a memory storing computer-executable instructions, that when executed, cause the processor to: determine a pulley rotation that, when applied to a pulley coupled to the elongate shaft by the end effector, is expected to relax the elongate shaft to a neutral position; drive the one or more drive outputs based at least in part on the pulley rotation; monitor tension on one or more pull wires coupled to the pulley; and control the one or more drive outputs based at least in part on the tension.

In some aspects, the techniques described herein relate to a robotic system, wherein the pulley is a dual-wire pulley and the pulley rotation is determined based on a kinematic model for the dual-wire pulley.

In some aspects, the techniques described herein relate to a robotic system, wherein: the neutral position is a zero degree articulation, the memory further includes computer-executable instructions, that when executed, causes the processor to determine that the tension is below a minimum tension threshold, and the controlling includes stopping the driving the one or more outputs based on the tension falling below the minimum tension threshold.

In some aspects, the techniques described herein relate to a robotic system, wherein the memory further includes computer-executable instructions, that when executed, causes the processor to: determine that a magnitude of the tension is increasing; and drive the one or more drive outputs in the opposite direction of the pulley rotation.

In some aspects, the techniques described herein relate to a robotic system, wherein the memory further includes computer-executable instructions, that when executed, causes the processor to: determine a homing offset; and apply the homing offset to a kinematic model associated with the elongate shaft.

In some aspects, the techniques described herein relate to a robotic system, wherein the elongate shaft is docked to the end effector with a non-zero articulation, and wherein the determining the homing offset includes determining the non-zero articulation.

In some aspects, the techniques described herein relate to a robotic system, wherein the determining the homing offset includes determining a point in the kinematic model where the driving the one or more drive outputs based at least in part on the pulley rotation causes: the tension to increases for a time period; and the tension at an end of the time period to be greater than a maximum tension during relaxation threshold.

In some aspects, the techniques described herein relate to a robotic system, wherein the determining the homing offset includes computing the homing offset based on a difference between the point and a pulley rotation corresponding to an edge of a center dead zone.

In some aspects, the techniques described herein relate to a robotic system, wherein the memory further includes computer-executable instructions, that when executed, causes the processor to: receive a relaxation command.

In some aspects, the techniques described herein relate to a robotic system, wherein the relaxation command is received while the elongated shaft is in a patient body.

In some aspects, the techniques described herein relate to a method of robotically articulating an instrument, the method including: determining a pulley rotation that, when applied to a pulley coupled to an elongate shaft by a robotic manipulator, is expected to relax the elongate shaft to a neutral position; driving one or more drive outputs based at least in part on the pulley rotation; monitoring tension on one or more pull wires coupled to the pulley; and controlling the driving the one or more drive outputs based at least in part on the tension.

In some aspects, the techniques described herein relate to a method, wherein the pulley is a dual-wire pulley and the pulley rotation is determined based on a kinematic model for the dual-wire pulley.

In some aspects, the techniques described herein relate to a method, further including determining that the tension is below a minimum tension threshold, wherein the neutral position is a zero degree articulation, and the controlling includes stopping the driving the one or more outputs based on the tension falling below the minimum tension threshold.

In some aspects, the techniques described herein relate to a method, further including: determining that a magnitude of the tension is increasing; and driving the one or more drive outputs in the opposite direction of the pulley rotation.

In some aspects, the techniques described herein relate to a method, further including: determining a homing offset; and applying the homing offset to a kinematic model associated with the elongate shaft.

In some aspects, the techniques described herein relate to a method, wherein the elongate shaft is docked to the robotic manipulator with a non-zero articulation, and wherein the determining the homing offset includes determining the non-zero articulation.

In some aspects, the techniques described herein relate to a method, wherein the determining the homing offset includes determining a point in the kinematic model where the driving the one or more drive outputs based at least in part on the pulley rotation causes: the tension to increases for a time period; and the tension at an end of the time period to be greater than a maximum tension during relaxation threshold.

In some aspects, the techniques described herein relate to a method, wherein the determining the homing offset includes computing the homing offset based on a difference between the point and a pulley rotation corresponding to an edge of a center dead zone.

In some aspects, the techniques described herein relate to a method, further including: receiving a relaxation command.

In some aspects, the techniques described herein relate to a method, wherein the relaxation command is received while the elongated shaft is in a patient body.

In some aspects, the techniques described herein relate to a robotic system including: an end effector including one or more drive outputs configured to cause articulation of an elongate shaft of an instrument coupled to the end effector; a processor; and a memory storing computer-executable instructions, that when executed, cause the processor to: determine a pulley rotation that, when applied to a pulley coupled to the elongate shaft by the end effector, is expected to articulate the elongate shaft to a desired articulation; drive the one or more drive outputs based at least in part on the pulley rotation; and during the driving the one or more drive outputs: monitor tension on one or more pull wires coupled to the pulley; determine that the tension is greater than an allowable center dead zone tension band; and perform homing to determine a homing offset.

In some aspects, the techniques described herein relate to a robotic system, wherein the pulley is a dual-wire pulley and the pulley rotation is determined based on a kinematic model for the dual-wire pulley.

In some aspects, the techniques described herein relate to a robotic system, wherein the performing the homing includes computing the homing offset based on a difference between a first pulley rotation associated with the tension greater than the allowable center dead zone tension band and a second pulley rotation corresponding to an edge of a center dead zone.

In some aspects, the techniques described herein relate to a robotic system, wherein the performing the homing is executed during an initial articulation of the elongate shaft.

In some aspects, the techniques described herein relate to a robotic system, wherein the memory further includes computer-executable instructions, that when executed, causes the processor to: apply the homing offset to a kinematic model associated with the elongate shaft.

In some aspects, the techniques described herein relate to a robotic system, wherein the monitoring tension on the one or more pull wires includes: sampling the monitored tension over a lookback window; and computing at least one of a mean, a median, or a mode of the monitored tension over the lookback window.

In some aspects, the techniques described herein relate to a robotic system, wherein the elongate shaft is docked to the end effector with a non-zero articulation, and wherein the determining the homing offset includes determining the non-zero articulation.

In some aspects, the techniques described herein relate to a robotic system, wherein the memory further includes computer-executable instructions, that when executed, causes the processor to: determine that the tension is greater than a bypass tension threshold; and terminate the homing based at least in part on the determining that the tension is greater than the bypass tension threshold.

In some aspects, the techniques described herein relate to a robotic system, wherein the memory further includes computer-executable instructions, that when executed, causes the processor to: determine that a current pulley rotation is greater than an allowable pulley rotation threshold; and terminate the homing based at least in part on the determining that the current pulley rotation is greater than the allowable pulley rotation threshold.

In some aspects, the techniques described herein relate to a robotic system, wherein at least one of an allowable center dead zone tension band, a bypass tension threshold, or an allowable pulley rotation threshold is associated with a kinematic model for the elongated shaft.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIG. 4 illustrates medical system components that may be implemented in any of the medical systems of FIGS. 1-3 in accordance with one or more embodiments.

DETAILED DESCRIPTION

Figure 1:
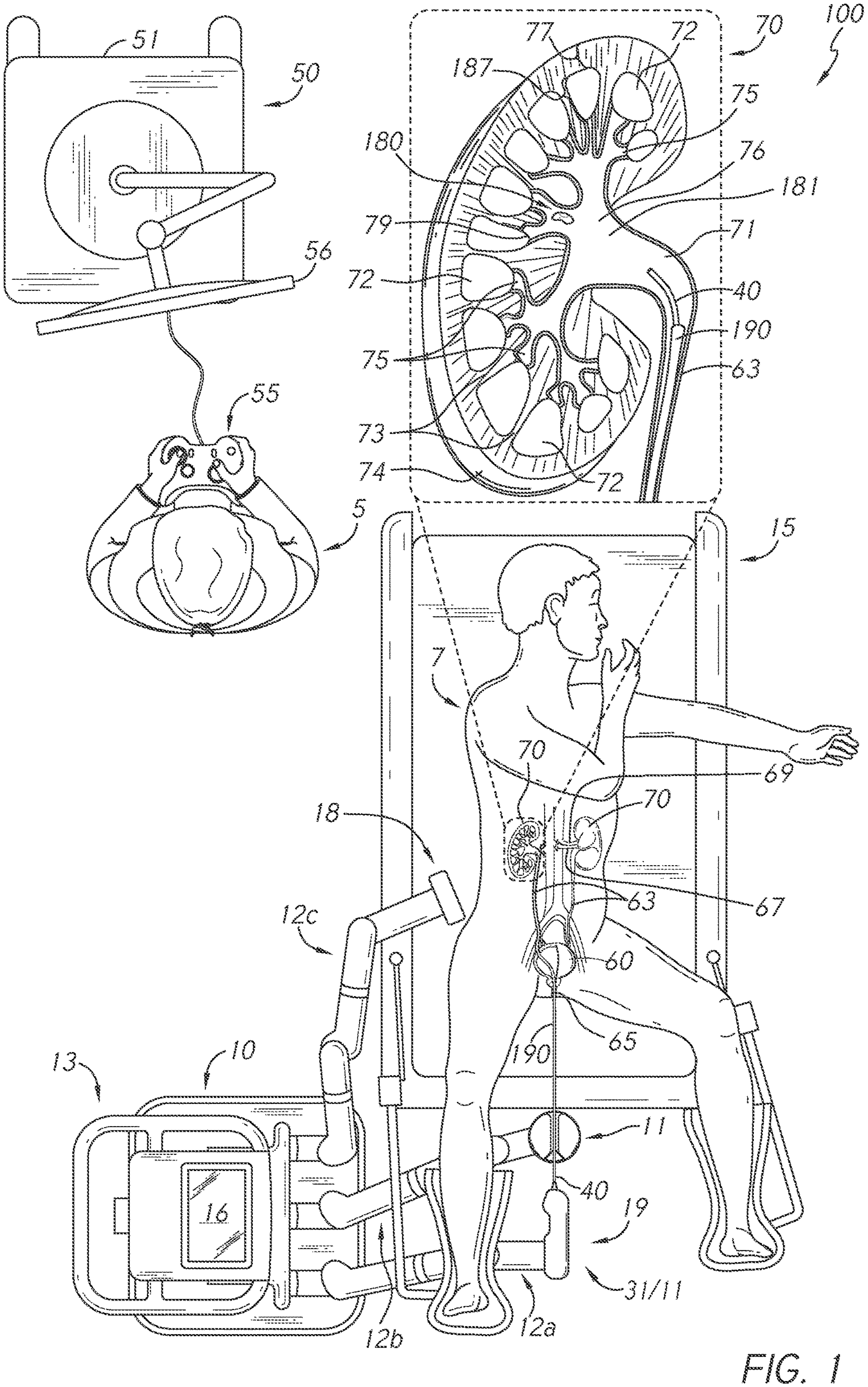
FIG. 1 illustrates an embodiment of a robotic medical system including a shaft-type instrument coupled to a robotic end effector in accordance with one or more embodiments.

The headings provided herein are for convenience only and do not necessarily affect the scope or meaning of the claimed invention. Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain reference numbers are re-used across different figures of the figure set of the present disclosure as a matter of convenience for devices, components, systems, features, and/or modules having features that may be similar in one or more respects. However, with respect to any of the embodiments disclosed herein, re-use of common reference numbers in the drawings does not necessarily indicate that such features, devices, components, or modules are identical or similar. Rather, one having ordinary skill in the art may be informed by context with respect to the degree to which usage of common reference numbers can imply similarity between referenced subject matter. Use of a particular reference number in the context of the description of a particular figure can be understood to relate to the identified device, component, aspect, feature, module, or system in that particular figure, and not necessarily to any devices, components, aspects, features, modules, or systems identified by the same reference number in another figure. Furthermore, aspects of separate figures identified with common reference numbers can be interpreted to share characteristics or to be entirely independent of one another. In some contexts, features associated with separate figures that are identified by common reference numbers are not related and/or similar with respect to at least certain aspects.

The present disclosure provide systems, devices, and methods for monitoring and controlling articulation of an instrument shaft, such as a medical endoscope. Articulation of instruments in accordance with the present disclosure can be implemented by tensioning one or more tendons, referred to herein as "pull wires," that traverse a shaft of the instrument. With respect to medical instruments described in the present disclosure, the term "instrument" is used according to its broad and ordinary meaning and may refer to any type of tool, device, assembly, system, subsystem, apparatus, component, or the like. In some contexts herein, the term "device" may be used substantially interchangeably with the term "instrument." Furthermore, the term "shaft" is used herein according to its broad and ordinary meaning and may refer to any type of elongate cylinder, tube, scope (e.g., endoscope), prism (e.g., rectangular, oval, elliptical, or oblong prism), wire, or similar, regardless of cross-sectional shape. It should be understood that any reference herein to a "shaft" or "instrument shaft" can be understood to possibly refer to an endoscope. The term "algorithm" is used according to its broad and ordinary meaning and may refer to any process or set of rules to be followed in calculations or other operations to solve a problem. The process or set of rules of the "algorithm" may be performable on a computing device, system, server, cloud, control circuitry, or other machines, as well as performable by one or more persons.

Medical Procedures

Although certain aspects of the present disclosure are described in detail herein in the context of renal, urological, and/or nephrological procedures, such as kidney stone removal/treatment procedures, it should be understood that such context is provided for convenience and clarity, and instrument articulation control concepts disclosed herein are applicable to any suitable medical procedures, such as robotic bronchoscopy, laproscopy, arthroscopy, colonoscopy, laryngoscopy, neuroendoscopy, proctoscopy, anoscopy, gastroscopy, sigmoidoscopy, thoracoscopy, colposcopy, esophagoscopy, or other endoscopic or elongate-shaft-based procedure.

In certain medical procedures, such as ureteroscopy procedures, elongate medical instruments that access the treatment site through an access sheath may be utilized to remove debris, such as kidney stones and stone fragments or other refuse or contaminant(s), from the treatment site. Kidney stone disease, also known as urolithiasis, is a medical condition that involves the formation in the urinary tract of a solid piece of material, referred to as "kidney stones," "urinary stones," "renal calculi," "renal lithiasis," or "nephrolithiasis." Urinary stones may be formed and/or found in the kidneys, the ureters, and the bladder (referred to as "bladder stones"). Such urinary stones can form as a result of mineral concentration in urinary fluid and can cause significant abdominal pain once such stones reach a size sufficient to impede urine flow through the ureter or urethra. Urinary stones may be formed from calcium, magnesium, ammonia, uric acid, cystine, and/or other compounds or combinations thereof.

Several methods can be used for treating patients with kidney stones, including observation, medical treatments (such as expulsion therapy), non-invasive treatments (such as extracorporeal shock wave lithotripsy (ESWL)), minimally invasive or surgical treatments (such as ureteroscopy and percutaneous nephrolithotomy ("PCNL")), and so on. In some approaches (e.g., ureteroscopy and PCNL), the physician gains access to the stone, the stone is broken into smaller pieces or fragments, and the relatively small stone fragments/particulates are extracted from the kidney using a basketing device and/or aspiration.

In some procedures, surgeons may insert an endoscope (e.g., ureteroscope) into the urinary tract through the urethra to remove urinary stones from the bladder and ureter. Typically, a ureteroscope includes a camera at its distal end configured to enable visualization of the urinary tract. The ureteroscope can also include, or allow for placement in a working channel of the ureteroscope, a lithotripsy device configured to capture or break apart urinary stones. In some procedures, such as procedures for removing relatively large stones/fragments, physicians may use a percutaneous nephrolithotomy ("PCNL") technique that involves inserting a nephroscope through the skin (i.e., percutaneously) and intervening tissue to provide access to the treatment site for breaking-up and/or removing the stone(s). A percutaneous-access device (e.g., nephroscope, sheath, sheath assembly, and/or catheter) used to provide an access channel to the target anatomical site (and/or a direct-entry endoscope) may include one or more fluid channels for providing irrigation fluid flow to the target site and/or aspirating fluid from the target site (e.g., through passive outflow and/or active suction).

Robotic-assisted ureteroscopic procedures can be implemented in connection with various medical procedures, such as kidney stone removal procedures, wherein robotic tools can enable a physician/urologist to perform endoscopic target access as well as percutaneous access/treatment. Advantageously, aspects of the present disclosure relate to systems, devices, and methods for robotically controlling articulation of instrument shafts (e.g., endoscope shafts) in a manner as to reduce the risk of injury or damage to the patient anatomy and/or the instrument.

Medical System

FIG. 1 illustrates an example medical system 100 for performing various medical procedures in accordance with aspects of the present disclosure. The medical system 100 may be used for, for example, endoscopic (e.g., ureteroscopic) procedures. As referenced and described above, certain ureteroscopic procedures involve the treatment/removal of kidney stones. In some implementations, kidney stone treatment can benefit from the assistance of certain robotic technologies/devices. Robotic medical solutions can provide relatively higher precision, superior control, and/or superior hand-eye coordination with respect to certain instruments compared to strictly manual procedures. For example, robotic-assisted ureteroscopic access to the kidney in accordance with some procedures can advantageously enable a urologist to articulate a ureteroscope using robotically controlled gears/drives coupled to a handle/base portion of the ureteroscope. Although the medical system 100 of FIG. 1 is presented in the context of a ureteroscopic procedure, it should be understood that the principles disclosed herein may be implemented in any type of endoscopic procedure.

The medical system 100 includes a robotic system 10 (e.g., mobile robotic cart) configured to engage with and/or control a medical instrument 19 (e.g., endoscope/ureteroscope) including a proximal handle/base 31 and a shaft 40 coupled to the handle 31 at a proximal portion thereof to perform a direct-entry procedure on a patient 7. In some instances, the term "medical instrument" may interchangeably refer to any portions of the medical instrument 19 including the proximal handle/base 31, the shaft 40, a scope, a scope tip, or the like. The term "direct entry" is used herein according to its broad and ordinary meaning and may refer to any entry of instrumentation through a natural or artificial opening in a patient's body. For example, with reference to FIG. 1, the direct entry of the scope/shaft 40 into the urinary tract of the patient 7 may be made through the urethra 65. The term "patient" is used herein to refer to live patient as well as any subjects to which the present disclosure may be applicable. For example, the "patient" may refer to subjects including mannequins used in dry runs, models in computer simulations, or the like that covers non-live patients or subjects.

It should be understood that the direct-entry instrument 19 may be any type of shaft-based medical instrument, including an endoscope (such as a ureteroscope), catheter (such as a steerable or non-steerable catheter), nephroscope, laparoscope, or other type of medical instrument. Embodiments of the present disclosure relating to ureteroscopic procedures for removal of kidney stones through a ureteral access sheath (e.g., the ureteral access sheath 190) are also applicable to solutions for removal of objects through percutaneous access, such as through a percutaneous access sheath. For example, instrument(s) may access the kidney percutaneously through, for example, a percutaneous access sheath to capture and remove kidney stones. The term "percutaneous access" is used herein according to its broad and ordinary meaning and may refer to entry, such as by puncture and/or minor incision, of instrumentation through the skin of a patient and any other body layers necessary to reach a target anatomical location associated with a procedure (e.g., the calyx network of the kidney 70).

The medical system 100 includes a control system 50 configured to interface with the robotic system 10, provide information regarding the procedure, and/or perform a variety of other operations. For example, the control system 50 can include one or more display(s) 56 configured to present certain information to assist the physician 5 and/or other technician(s) or individual(s). The medical system 100 can include a table 15 configured to hold the patient 7. The medical system 100 may further include an electromagnetic (EM) field generator 18, which may be held by one or more of the robotic arms 12 of the robotic system 10 or may be a stand-alone device and/or mounted to the table 15. Although the various robotic arms 12 are shown in various positions and coupled to various tools/devices, it should be understood that such configurations are shown for convenience and illustration purposes, and such robotic arms may have different configurations over time and/or at different points during a medical procedure. Furthermore, the robotic arms 12 may be coupled to different devices/instruments than shown in FIG. 1, and in some cases or periods of time, one or more of the arms may not be utilized or coupled to a medical instrument. Articulation of the shaft 40 may be controlled robotically, such as through operation of an end effector associated with the robot arm 12*a*, wherein such operation may be controlled by the control system 50 and/or robotic system 10. The term "end effector" is used herein according to its broad and ordinary meaning and may refer to any type of robotic manipulator device, component, and/or assembly. In implementations in which an adapter, such as a sterile adapter, is coupled to a robotic end effector or other robotic manipulator, the term "end effector" may refer to the adapter (e.g., sterile adapter), or any other robotic manipulator device, component, or assembly associated with and/or coupled to the end effector. In some contexts, the combination of a robotic end effector and adapter may be referred to as an instrument manipulator assembly, wherein such assembly may or may not also include a medical instrument (or instrument handle/base) physically coupled to the adapter and/or end effector. The terms "robotic manipulator" and "robotic manipulator assembly" are used according to their broad and ordinary meanings, and may refer to a robotic end effector and/or sterile adapter or other adapter component coupled to the end effector, either collectively or individually. For example, the terms "robotic manipulator" and "robotic manipulator assembly" may refer to an instrument device manipulator (IDM) including one or more drive outputs, whether embodied in a robotic end effector, sterile adapter, and/or other component(s). The terms "associated" and "associated with" are used herein according to their broad and ordinary meanings. For example, where a first feature, element, component, device, or member is described as being "associated with" a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly.

In an example use case, if the patient 7 has a kidney stone (or stone fragment) 180 located in a kidney 70, the physician 5 may perform a procedure to remove the stone 180 through the urinary tract (63, 60, 65). In some embodiments, the physician 5 can interact with the control system 50 and/or the robotic system 10 to cause/control the robotic system 10 to advance and navigate the medical instrument shaft 40 (e.g., a scope) from the urethra 65, through the bladder 60, up the ureter 63, and into the renal pelvis 71 and/or calyx network of the kidney 70 where the stone 180 is located. The physician 5 can further interact with the control system 50 and/or the robotic system 10 to cause/control the advancement of a basketing device or other instrument through a working channel of the instrument shaft 40 to facilitate capture and removal of a kidney stone or stone fragment. The control system 50 can provide information via the display(s) 56 that is associated with the medical instrument 40, such as real-time endoscopic images captured therewith, and/or other instruments of the medical system 100, to assist the physician 5 in navigating/controlling such instrumentation.

The renal anatomy is described herein for reference with respect to certain medical procedures relating to aspects of the present inventive concepts. The kidneys 70, shown roughly in typical anatomical position in FIG. 1, generally comprise two bean-shaped organs located on the left and right sides, respectively, in the retroperitoneal space. In adult humans, the kidneys are generally about 11 cm in height/length. The kidneys receive blood from the paired renal arteries 69; blood exits the kidney via the paired renal veins 67. Each kidney 70 is fluidly coupled with a respective ureter 63, which generally comprises a tube that carries excreted urine from the kidney 70 to the bladder 60.

The kidneys 70 are typically located relatively high in the abdominal cavity and are positioned in a retroperitoneal position at a slightly oblique angle. The asymmetry within the abdominal cavity, generally caused by the position of the liver, results in the right kidney (shown in detail in FIG. 1) typically being slightly lower and smaller than the left, and being placed slightly more to the middle than the left kidney. On top of each kidney is an adrenal gland (not shown). The upper parts of the kidneys 70 are partially protected by the $11^{th}$ and $12^{th}$ ribs (not shown). Each kidney, with its adrenal gland, is generally surrounded by two layers of fat: the perirenal fat disposed between renal fascia and renal capsule and pararenal fat that is superior to the renal fascia.

The kidneys 70 help control the volumes of various body fluid compartments, fluid osmolality, acid-base balance, various electrolyte concentrations, and removal of toxins. The kidneys 70 provide filtration functionality by secreting certain substances and reabsorbing others. Examples of substances secreted into the urine are hydrogen, ammonium, potassium and uric acid. In addition, the kidneys also carry out various other functions, such as hormone synthesis, and others.

A recessed area on the concave border of the kidney 70 is the renal hilum 181, where the renal artery 69 enters the kidney 70 and the renal vein 67 and ureter 63 leave. The kidney 70 is surrounded by tough fibrous tissue, the renal capsule 74, which is itself surrounded by perirenal fat, renal fascia, and pararenal fat. The anterior (front) surface of these tissues is the peritoneum, while the posterior (rear) surface is the transversalis fascia.

The functional substance, or parenchyma, of the kidney 70 is divided into two major structures: the outer renal cortex 77 and the inner renal medulla 187. These structures take the shape of a plurality of generally cone-shaped renal lobes, each containing renal cortex surrounding a portion of medulla called a renal pyramid 72. Between the renal pyramids 72 are projections of cortex called renal columns 73. Nephrons (not shown in detail in FIG. 1), the urine-producing functional structures of the kidney, span the cortex 77 and medulla 187. The initial filtering portion of a nephron is the renal corpuscle, which is located in the cortex and is followed by a renal tubule that passes from the cortex deep into the medullary pyramids. Part of the renal cortex, a medullary ray, is a collection of renal tubules that drain into a single collecting duct.

The tip/apex, or papilla 79, of each renal pyramid empties urine into a respective minor calyx 75; minor calyces 75 empty into major calyces 76, and major calyces 76 empty into the renal pelvis 71, which transitions to the ureter 63. The manifold-type collection of minor and major calyces may be referred to herein as the "calyx network" of the kidney. At the hilum 181, the ureter 63 and renal vein 67 exit the kidney and the renal artery 69 enters the kidney. Hilar fat and lymphatic tissue with lymph nodes surround these structures. The hilar fat is contiguous with a fat-filled cavity called the renal sinus. The renal sinus collectively contains the renal pelvis 71 and calyces 75, 76 and separates these structures from the renal medullary tissue. The funnel/tubular-shaped anatomy associated with the calyces can be referred to as the infundibulum/infundibula. That is, an infundibulum generally leads to the termination of a calyx where a papilla is exposed within the calyx.

With further reference to the medical system 100, the medical instrument shaft 40 (e.g., scope, directly-entry instrument, etc.) can be advanced into the kidney 70 through the urinary tract. Specifically, a ureteral access sheath 190 may be disposed within the urinary tract to an area near the kidney 70. The shaft 40 may be passed through the ureteral access sheath 190 to gain access to the internal anatomy of the kidney 70, as shown. The distal portion of the scope/shaft 40 deployed from the sheath 190 may be articulatable to allow the surgeon 5 to use inputs of the control device 55 to cause the robotic system 10 to articulate the shaft 40 towards the target kidney stone. Once at the site of the kidney stone 180 (e.g., within a target calyx 75 of the kidney 70 through which the stone 180 is accessible), the medical instrument 19 and/or shaft 40 thereof can be used to channel/direct the basketing device to the target location. Once the stone 180 has been captured in the distal basket portion of the basketing device/assembly, the utilized ureteral access path may be used to extract the kidney stone 180 from the patient 7.

The various scope/shaft-type instruments disclosed herein, such as the shaft 40 of the medical system 100, can be configured to navigate within the human anatomy, such as within a natural orifice or lumen of the human anatomy. The terms "scope" and "endoscope" are used herein according to their broad and ordinary meanings, and may refer to any type of elongate (e.g., shaft-type) medical instrument having image generating, viewing, and/or capturing functionality and being configured to be introduced into any type of organ, cavity, lumen, chamber, or space of a body. A scope can include, for example, a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), colonoscope (e.g., for accessing the colon and/or rectum), borescope, and so on. Scopes/endoscopes, in some instances, may comprise an at least partially rigid and/or flexible tube, and may be dimensioned to be passed within an outer sheath, catheter, introducer, or other lumen-type device, or may be used without such devices.

Figure 2:
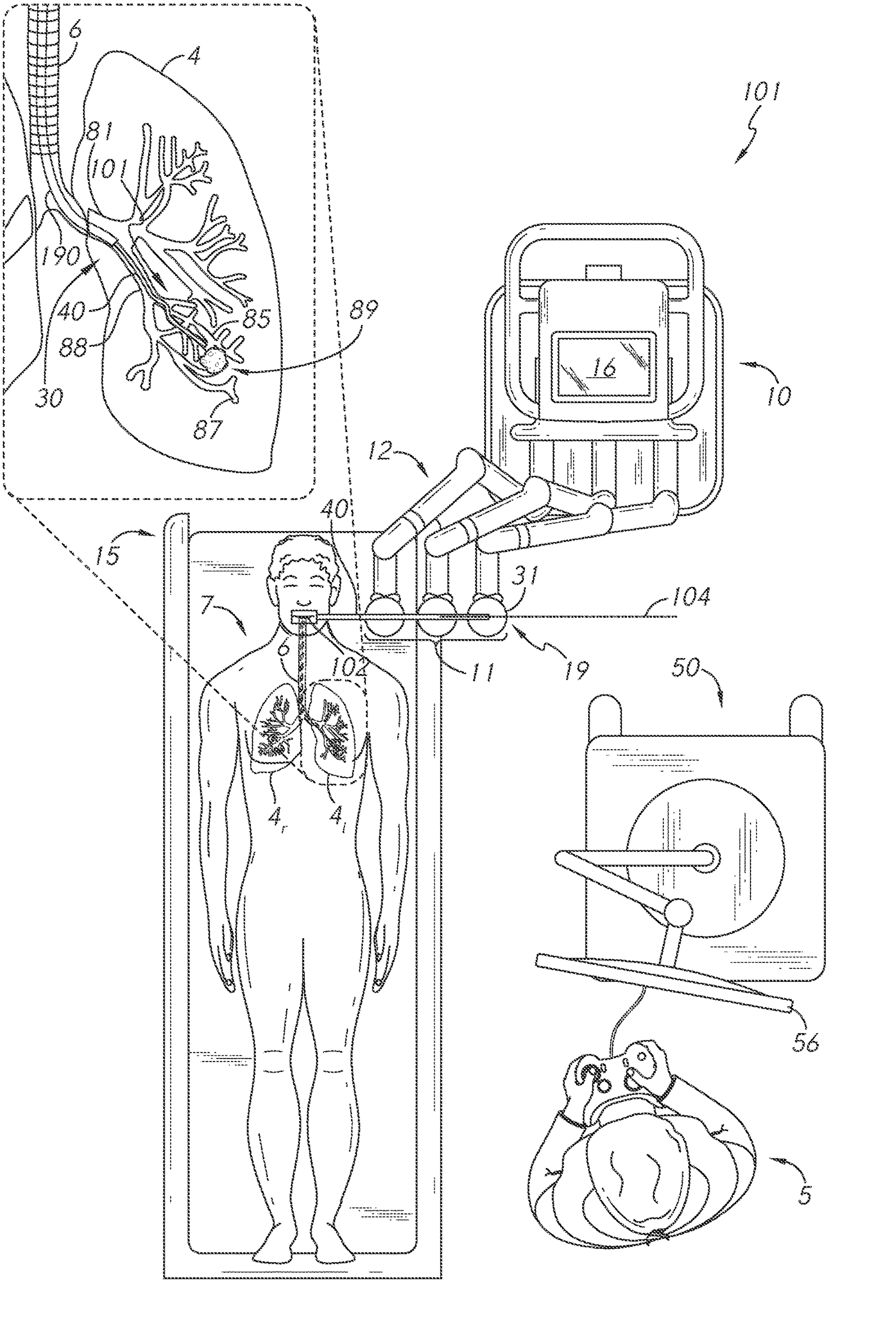
FIG. 2 illustrates a robotic system arranged for diagnostic and/or therapeutic bronchoscopy in accordance with one or more embodiments.

FIG. 2 illustrates a cart-based robotic system 101 arranged for diagnostic and/or therapeutic bronchoscopy in accordance with one or more embodiments. During a bronchoscopy, the arm(s) 12 of the robotic system 10 may be configured to drive a medical instrument shaft 40, such as a steerable endoscope, which may be a procedure-specific bronchoscope for bronchoscopy, through a natural orifice access point (e.g., the mouth of the patient 7 positioned on a table 15 in the present example) to deliver diagnostic, therapeutic tools, and/or treatments. Depending on a medical procedure performed, the robotic arms 12 may include more or fewer arms. As shown, the robotic system 10 (e.g., cart) may be positioned proximate to the patient's upper torso in order to provide access to the access point. Similarly, the robotic arms 12 may be actuated to position the bronchoscope/shaft 40 relative to the access point. The arrangement in FIG. 2 may also be utilized when performing a gastrointestinal (GI) procedure with a gastroscope, a specialized endoscope for GI procedures.

Once the robotic system 10 is properly positioned, the robotic arms 12 may insert the steerable/articulatable endoscope 40 into the patient robotically, manually, or a combination thereof. The endoscope 40 may be advance within an outer sheath 190, wherein each of the scope 40 and the sheath 190 may be coupled to and/or associated with one of the set of instrument feeders and/or instrument handles 11, each instrument feeder/handle 11 being coupled to the distal end of a respective robotic arm 12. This linear arrangement of the feeder(s)/handle(s) 11 can create a "virtual rail" 104 that may be repositioned in space by manipulating the one or more robotic arms 12 into different angles and/or positions. One or more of the instrument feeder(s)/handle(s) 11 can be configured to implement robotic articulation of the shaft 40 and may be configured according to one or more embodiments disclosed herein for such purpose.

The endoscope 40 may be directed down the patient's trachea and lungs after insertion using precise articulation commands from the robotic system 10 until reaching the target operative site. For example, the endoscope 40 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. For example, when a nodule is identified as being malignant, the endoscope 40 may endoscopically deliver tools to resect the potentially cancerous tissue. In some instances, diagnostic and therapeutic treatments can be delivered in separate procedures. In those circumstances, the endoscope 40 may also be used to deliver a fiducial marker to "mark" the location of the target nodule as well.

In the robotic system 101, a patient introducer 102 can be attached to the patient 7 via a port (not shown; e.g., surgical tube). The curvature of the patient introducer 102 may enable the robotic system 10 to manipulate the instrument 40 from a position that is not in direct axial alignment with the patient-access port, thereby allowing for greater flexibility in the placement of the robotic system 10 within the room. Further, the curvature of the patient introducer 102 may allow the robotic arms 12 of the robotic system 10 to be substantially horizontally aligned with the patient introducer 102, which may facilitate manual movement of the robotic arm(s) 12 if needed. The control system 50 and/or robotic cart 10 can include control circuitry configured to implement scope articulation control as described herein.

For reference, FIG. 2 shows details of certain respiratory anatomy in which the scope 40 may be advanced and/or articulated. Generally, the respiratory system comprises certain passages, vessels, organs, and muscles that aid the body in the exchange of gases between the air and blood, and between the blood and the cells of the body. The respiratory system includes the upper respiratory tract, which comprises the nose/nasal cavity, the pharynx (i.e., throat), and the larynx (i.e., voice box). The respiratory system further includes the lower respiratory tract, which is shown in detail and comprises the trachea 6, the lungs 4, and the various segments of the bronchial tree 30, including the alveoli and alveolar ducts, which comprise clusters of small air sacs that are responsible for gas exchange between the lungs and the pulmonary blood vessels. The bronchial tree 30 is an example luminal network in which robotically controlled instruments may be navigated and articulated in accordance with the inventive solutions presented here. However, although aspects of the present disclosure are presented in the context of luminal networks including a bronchial network of airways (e.g., lumens, branches) of a patient's lung, embodiments of the present disclosure can be implemented in other types of luminal networks, such as renal networks, cardiovascular networks (e.g., arteries and veins), gastrointestinal tracts, urinary tracts, etc. The organs of the lower respiratory tract are located inside the chest cavity, which is surrounded by the sternum (i.e., chest bone) and ribcage on the front and the vertebrae (i.e., backbones) on the back, which collectively protect the lungs and other organs in the chest.

The trachea 6 is located just below the larynx 5 and provides the main airway to the lungs 4. The left 41 and right 4, lungs are responsible for providing oxygen to capillaries and exhaling carbon dioxide. The bronchi 7 branch from the trachea 6 into each lung 4 and create the network of intricate passages that supply the lungs 4 with air. The diaphragm is the main respiratory muscle that contracts and relaxes to allow air into the lungs. The trachea 6 is a tube that carries the air in and out of the lungs 4. Each lung 4 has associated therewith a tube 7 called a bronchus that connects to the trachea. The trachea and bronchi form the bronchial tree 30. The bronchial tree 30 includes primary bronchi 81, which branch off into smaller secondary 88 and tertiary 85 bronchi, and terminate in even smaller tubes called bronchioles 87. Each bronchiole tube is coupled to a cluster of aveoli. During the inspiration phase of the respiratory cycle, air enters through the mouth and nose and travel down the throat into the trachea 6, into the lungs 4 through the right and left main bronchi 81, into the smaller bronchi airways 88, 85, into the smaller bronchiole tubes 87, and into the alveoli, where oxygen and carbon dioxide exchange takes place.

Lung cancer and other cancers generally involve abnormal cell growth (e.g., in the area of the lungs or other anatomy), which can have the potential to invade or spread to other parts of the body. For example, cancer can form in tissues of the lung, such as in the cells that line the various air passages. When not treated in an effective and/or timely manner, lung cancers can spread/metastasize to lymph nodes or other organs in the body, which can severely impact patient recovery prospects. In FIG. 2, the patient 7 is shown having a mass of tissue 89, referred to as a lung nodule, that has formed in the area of the lungs 4. Such lung nodules can be benign or cancerous. Determination of whether a lung nodule is cancerous can involve utilization of one or more anatomical imaging modalities and/or minimally invasive lung biopsy, such as in connection with certain thoracoscopic, bronchoscopic, and/or robotic procedure(s). For example, robotically controlled instrumentation can be implemented to perform a diagnostic biopsy procedure from within the bronchial network.

In the illustrated example, the medical instrument 19 includes an endoscope 40. The scope 40 may be slideably positioned within a working channel of the sheath 190. The scope 40 may have a lumen (i.e., 'working channel') through which instruments, for example biopsy and/or injection needles, cytology brushes, and/or tissue sampling forceps, can be passed to the target tissue site of the nodule 89. The terms "lumen" and "channel" are used herein according to their broad and ordinary meanings and may refer to a physical structure forming a cavity, void, conduit, or other pathway, such as an at least partially rigid elongate tubular structure, or may refer to a cavity, void, pathway, or other channel, itself, that occupies a space within an elongate structure (e.g., a tubular structure). Therefore, with respect to an elongate tubular structure, such as a shaft, tube, or the like, the terms "lumen" or "channel" may refer to the elongate tubular structure and/or to the channel or space within the elongate tubular structure. The telescopic arrangement of the sheath 190 and the scope 40 may allow for a relatively thin design of the scope 40 and may improve a bend radius of the scope 40 while providing a structural support via the sheath 190. As shown, to reach the nodule 89, the scope shaft 40 may be navigated or guided through the lumens or branches of the luminal network 7. An operator (such as a surgeon) can navigate the instrument 40 to the nodule 89 using various advancement and articulation commands.

Figure 3:
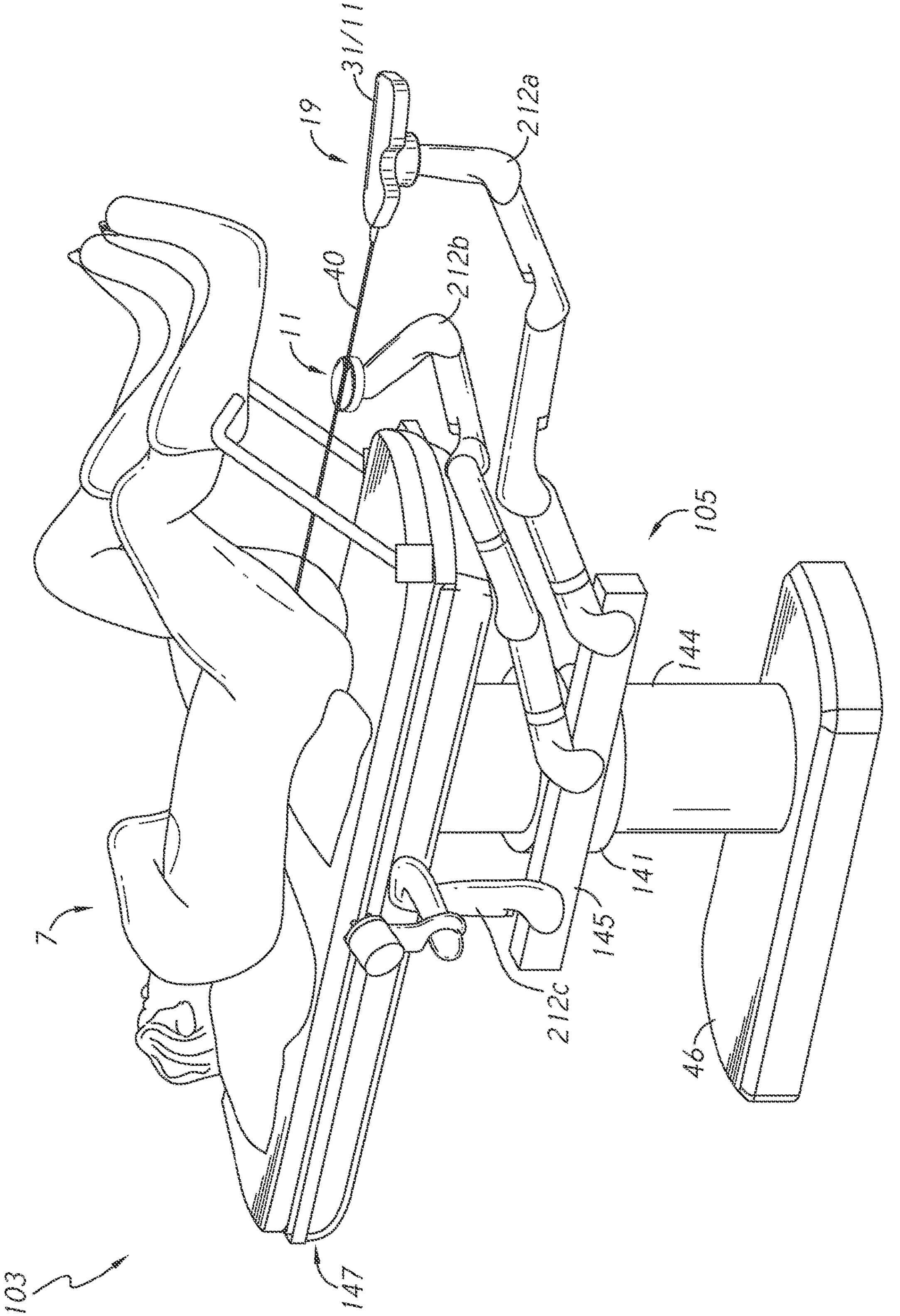
FIG. 3 illustrates a table-based robotic system in accordance with one or more embodiments.

FIG. 3 illustrates a table-based robotic system 103 in accordance with one or more embodiments of the present disclosure. The system 103 incorporates robotic components 105 with a table/platform 147, thereby allowing for a reduced amount of capital equipment within the operating room compared to some cart-based robotic systems, which can allow greater access to the patient 7 in some instances. Much like in cart-based systems, the instrument device manipulator assemblies associated with one or more robotic arms 212*a-c* of the system 103 may generally comprise instruments and/or instrument feeders that are designed to manipulate an elongated medical instrument/shaft, such as an endoscope 40 or the like, along a virtual rail/path.

As shown, the robotic-enabled table system 103 can include a column 144 coupled to one or more carriages 141 (e.g., ring-shaped movable structures), from which the robotic arms 212*a-c* may emanate. The carriage(s) 141 may translate along a vertical column interface that runs at least a portion of the length of the column 144 to provide different vantage points from which the robotic arms 212*a-c* may be positioned to reach the patient 7. The carriage(s) 141 may rotate around the column 144 in some embodiments using a mechanical motor positioned within the column 144 to allow the robotic arms 212*a-c* to have access to multiples sides of the table/platform 147. Rotation and/or translation of the carriage(s) 141 can allow the system 103 to align the medical instruments, such as endoscopes 40 and sheaths 190, into different access points on the patient 7. By providing vertical adjustment, the robotic arms 212*a-c* can advantageously be configured to be stowed compactly beneath the table/platform 147 of the table system 103 and subsequently raised during a procedure.

The robotic arms 212*a-c* may be mounted on the carriage (s) 141 through one or more arm mounts 145, which may comprise a series of joints that may individually rotate and/or telescopically extend to provide additional configurability to the robotic arms 212*a-c*. The column 144 structurally provides support for the table/platform 147 and a path for vertical translation of the carriage(s) 141. The column 144 may also convey power and control signals to the carriage(s) 141 and/or the robotic arms 212*a-c* mounted thereon. The system 103 can include certain control circuitry configured to control driving and/or articulation of the instrument shaft 40 using an end effector of one of the robotic arms 212*a-c*. Although a control tower/system is not shown in FIG. 3 for visual clarity, it should be understood that the system 103 may have a control tower/system as in any embodiment disclosed herein.

FIG. 4 shows an example embodiment of the control systems of any of FIGS. 1-3. The relevant control system 50 can be configured to provide various functionalities to assist in performing a medical procedure. In some embodiments, the control system 50 can be coupled to the robotic system 10 and operate in cooperation therewith to perform a medical procedure on the patient 7. For example, the control system 50 can communicate with the robotic system 10 via a wireless connection or a wired connection (e.g., to control the robotic system 10). Further, in some embodiments, the control system 50 can communicate with the robotic system 10 to receive position data therefrom relating to the position of the distal end of the scope 40. Such positional data relating to the position of the scope 40 may be derived using one or more electromagnetic sensors associated with the respective components, scope image processing functionality, and/or based at least in part on robotic system data (e.g., arm position data, known parameters/dimensions of the various system components, etc.).

FIG. 4 further shows an example embodiment of the robotic systems of any of FIGS. 1-3. The robotic system 10 can be configured to at least partly facilitate execution of a medical procedure. The robotic system 10 can be arranged in a variety of ways depending on the particular procedure. The robotic system 10 can include one or more robotic arms 12 configured to engage with and/or control, for example, the scope 40 to perform one or more aspects of a procedure. As shown, each robotic arm 12 can include multiple arm segments 23 coupled to joints 24, which can provide multiple degrees of movement/freedom. When the robotic system 10 is properly positioned, the scope 40 can be inserted into the patient 7 robotically using the robotic arms 12, manually by the physician 5, or a combination thereof. With reference to FIG. 1, a scope-driver/feeder instrument coupling 11 (i.e., instrument device manipulator (IDM)) can be attached to the distal end effector 22 of one of the arms 12*b* to facilitate robotic control/advancement of the scope 40. Another 12*a* of the arms may have associated therewith an instrument base/handle 31, wherein the scope 40 is physically coupled to the handle 31 at a proximal end of the scope 40. The scope 40 may include one or more working channels 44 through which additional tools, such as lithotripters, basketing devices, forceps, etc., can be introduced into the treatment site.

With reference to any of the systems of FIGS. 1-4, the robotic system 10 can be coupled to any component of the medical system, such as to the control system 50, the table 15, the EM field generator 18, the scope 40, and/or any type of percutaneous-access instrument (e.g., needle, catheter, nephroscope, etc.). In some embodiments, the robotic system 10 is communicatively coupled to the control system 50. For example, the robotic system 10 may be configured to receive control signals from the control system 50 to perform certain operations, such as to position one or more of the robotic arms 12 in a particular manner, manipulate (e.g., advance, articulate) the scope 40, and so on. In response, the robotic system 10 can control, using certain control circuitry 211, actuators 217, and/or other components of the robotic system 10, to perform the operations. For example, the control circuitry 211 may control articulation of the shaft/scope 40 by actuating drive output(s) of the end effector 22 coupled to the instrument handle 31. In some embodiments, the robotic system 10 and/or control system 50 is/are configured to receive images and/or image data from the scope 40 representing internal anatomy of the patient 7 and/or portions of the access sheath or other device components.

The robotic system 10 generally includes an elongated support structure (also referred to as a "column" 14), a robotic system base 25, and a console 13 at the top of the column 14. The column 14 may include one or more arm supports 17 (also referred to as a "carriage") for supporting the deployment of the one or more robotic arms 12 (three shown in FIGS. 1 and 2). The arm support 17 may include individually configurable arm mounts that rotate along a perpendicular axis to adjust the base of the robotic arms 12 for desired positioning relative to the patient.

The arm support 17 may be configured to vertically translate along the column 14. In some embodiments, the arm support 17 can be connected to the column 14 through slots 20 that are positioned on opposite sides of the column 14 to guide the vertical translation of the arm support 17. The slot 20 contains a vertical translation interface to position and hold the arm support 17 at various vertical heights relative to the robotic system base 25. Vertical translation of the arm support 17 allows the robotic system 10 to adjust the reach of the robotic arms 12 to meet a variety of table heights, patient sizes, and physician preferences. Similarly, the individually configurable arm mounts on the arm support 17 can allow the robotic arm base 21 of robotic arms 12 to be angled in a variety of configurations.

The robotic arms 12 may generally comprise robotic arm bases 21 and end effectors 22, separated by a series of linking arm segments 23 that are connected by a series of joints 24, each joint 24 comprising one or more independent actuators 217. Each actuator may comprise an independently controllable motor. Each independently controllable joint 24 can provide or represent an independent degree of freedom available to the robotic arm. In some embodiments, each of the arms 12 has seven joints, and thus provides seven degrees of freedom, including "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician 5 to move the arm joints into a clinically advantageous position away from the patient to create greater access, while avoiding arm collisions.

The robotic system base 25 balances the weight of the column 14, arm support 17, and arms 12 over the floor. Accordingly, the robotic system base 25 may house certain relatively heavier components, such as electronics, motors, power supply, as well as components that selectively enable movement or immobilize the robotic system. For example, the robotic system base 25 can include wheel-shaped casters 28 that allow for the robotic system to easily move around the operating room prior to a procedure. After reaching the appropriate position, the casters 28 may be immobilized using wheel locks to hold the robotic system 10 in place during the procedure.

Positioned at the upper end of column 14, the console 13 can provide both a user interface for receiving user input and a display screen 16 (or a dual-purpose device such as, for example, a touchscreen) to provide the physician/user 5 with both pre-operative and intra-operative data. Potential pre-operative data on the console/display (e.g., the display screen 16 of FIGS. 1 and 2) or display 56 may include pre-operative plans, navigation and mapping data derived from pre-operative computerized tomography (CT) scans, and/or notes from pre-operative patient interviews. Intra-operative data on display may include optical information provided from the tool, sensor, and coordinate information from sensors, as well as vital patient statistics, such as respiration, heart rate, and/or pulse. The console 13 may be positioned and tilted to allow the physician 5 to access the console from the side of the column 14 opposite arm support 17. From this position, the physician 5 may view the console 13, robotic arms 12, and patient while operating the console 13 from behind the robotic system 10. As shown, the console 13 can also include a handle 27 to assist with maneuvering and stabilizing the robotic system 10.

The end effector 22 of each of the robotic arms 12 may comprise, or be configured to have coupled thereto, an instrument device manipulator (IDM) (e.g., instrument base/handle) 11, which may be attached using a sterile adapter component in some instances. The combination of the end effector 22 and associated IDM, as well as any intervening mechanics or couplings (e.g., sterile adapter), can be referred to as a manipulator assembly. In some embodiments, the IDM 11 can be removed and replaced with a different type of IDM, for example, a first type of IDM/instrument may be configured to manipulate an endoscope/shaft, while a second type of IDM/instrument 31 may be associated with the shaft 40 (e.g., coupled to a proximal portion thereof) and configured to articulate the shaft. Another type of IDM/instrument may be configured to hold an electromagnetic field generator 18. An IDM can provide power and control interfaces. For example, the interfaces can include connectors to transfer pneumatic pressure, electrical power, electrical signals, and/or optical signals from the robotic arm 12 to the IDM 11. The IDMs 11 may be configured to manipulate medical instruments (e.g., surgical tools/instruments), such as the scope 40, using techniques including, for example, direct drives, harmonic drives, geared drives, belts and pulleys, magnetic drives, and the like. In some embodiments, the device manipulators 11 can be attached to respective ones of the robotic arms 12, wherein the robotic arms 12 are configured to insert or retract the respective coupled medical instruments into or out of the treatment site.

As referenced above, the systems of FIGS. 1-4 can include certain control circuitry configured to perform certain of the functionality described herein, including the control circuitry 211 of the robotic system 10 and the control circuitry 251 of the control system 50. That is, the control circuitry of the systems 100, 101, 103, 400 may be part of the robotic system 10, the control system 50, or some combination thereof. Therefore, any reference herein to control circuitry may refer to circuitry embodied in a robotic system, a control system, or any other component of a medical system, such as the systems 100, 101, 103, and 400 shown in FIGS. 1-4, respectively. The term "control circuitry" is used herein according to its broad and ordinary meaning, and may refer to any collection of processors, processing circuitry, processing modules/units, chips, dies (e.g., semiconductor dies including one or more active and/or passive devices and/or connectivity circuitry), microprocessors, micro-controllers, digital signal processors, microcomputers, central processing units, field-programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry referenced herein may further include one or more circuit substrates (e.g., printed circuit boards), conductive traces and vias, and/or mounting pads, connectors, and/or components. Control circuitry referenced herein may further comprise one or more storage devices, which may be embodied in a single memory device, a plurality of memory devices, and/or embedded circuitry of a device. Such data storage may comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware and/or software state machine, analog circuitry, digital circuitry, and/or logic circuitry, data storage device(s)/register(s) storing any associated operational instructions may be embedded within, or external to, the circuitry comprising the state machine, analog circuitry, digital circuitry, and/or logic circuitry.

The control circuitry 211, 251 may comprise computer-readable media storing, and/or configured to store, hard-coded and/or operational instructions corresponding to at least some of the steps and/or functions illustrated in one or more of the present figures and/or described herein. Such computer-readable media can be included in an article of manufacture in some instances. The control circuitry 211, 251 may be entirely locally maintained/disposed or may be remotely located at least in part (e.g., communicatively coupled indirectly via a local area network and/or a wide area network). Any of the control circuitry 211, 251 may be configured to perform any aspect(s) of the various processes disclosed herein, including the processes shown in FIGS. 11 and 13, as described below.

With respect to the robotic system 10, at least a portion of the control circuitry 211 may be integrated with the base 25, column 14, and/or console 13 of the robotic system 10, and/or another system communicatively coupled to the robotic system 10. With respect to the control system 50, at least a portion of the control circuitry 251 may be integrated with the console base 51 and/or display unit 56 of the control system 50. It should be understood that any description herein of functional control circuitry or associated functionality may be understood to be embodied in the robotic system 10, the control system 50, or any combination thereof, and/or at least in part in one or more other local or remote systems/devices, such as control circuitry associated with a handle/base of a shaft-type instrument (e.g., endoscope) in accordance with any of the disclosed embodiments.

The control circuitry 211 and/or control circuitry 251 may be communicatively coupled to one or more torque sensors 216 configured to generate signals indicative of torque on one or more actuators of the robotic system 10. The torque sensor(s) 216 may have any suitable or desirable configuration. For example, the torque sensor(s) 216 can act as a sensed mounting structure or load cell. In some embodiments, the torque sensor(s) 216 is/are configured as a reactive torque sensor that measures torque induced strain using one or more self-contained strain gauges to create a load cell. Although torque sensors 216 of a robotic system are described herein in the context of determining tension on pull wires/tendons of an endoscopic instrument coupled to the robotic system 10, such references may be understood to represent any type of sensor(s) or sensing mechanism configured to generate signals indicative of pull wire tension, such as strain gauges or the like. References herein to strain gauges can be any type of sensor configured to measure force/load on a robotic actuator, whether such force is rotational or linear in nature. That is, although rotational robotic output drives are disclosed in some contexts herein, it should be understood that inventive concepts disclosed herein apply to other types of actuators, such as linear drives.

With further reference to FIGS. 1-4, the control system 50 can include various I/O components 258 configured to assist the physician 5 or others in performing a medical procedure. For example, the input/output (I/O) components 258 can be configured to allow for user input to control/navigate the scope 40 and/or other robotically controlled instrument (e.g., basketing system) within the patient 7. In some embodiments, for example, the physician 5 can provide input to the control system 50 and/or robotic system 10 using one or more input control(s) 255, wherein in response to such input, control signals can be sent to the robotic system 10 to manipulate the scope 40. The control system 50 can include one or more display devices 56 to provide various information regarding a procedure. For example, the display(s) 56 can provide information regarding the scope 40. For example, the control system 50 can receive real-time images that are captured by the scope 40 and display the real-time images via the display(s) 56. Additionally, or alternatively, the control system 50 can receive signals (e.g., analog, digital, electrical, acoustic/sonic, pneumatic, tactile, hydraulic, etc.) from a medical monitor and/or a sensor associated with the patient 7, and the display(s) 56 can present information regarding the health or environment of the patient 7. Such information can include information that is displayed via a medical monitor including, for example, information relating to heart rate (e.g., ECG, HRV, etc.), blood pressure/rate, muscle bio-signals (e.g., EMG), body temperature, blood oxygen saturation (e.g., $SpO_2$), $CO_2$, brainwaves (e.g., EEG), environmental and/or local or core body temperature, and so on. Similarly, the robotic system 10 can include various I/O components 218, such integrated on the console 13, configured to assist the physician 5 or others in setting up the robotic system 10.

The various components of the systems of FIGS. 1-4 can be communicatively coupled to each other over a network, which can include a wireless network and/or a wired network. Example networks include one or more personal area networks (PANs), local area networks (LANs), wide area networks (WANs), Internet area networks (IANs), cellular networks, the Internet, personal area networks (PANs), body area network (BANs), etc. For example, the various communication interfaces 214, 254 of the systems of FIGS. 1-4 can be configured to communicate with one or more device/sensors/systems, such as over a wireless network connection and/or a wired network connection. In some embodiments, the various communication interfaces 214, 254 can implement a wireless technology such as Bluetooth, Wi-Fi, near-field communication (NFC), or the like. Furthermore, in some embodiments, the various components of the systems can be connected for data communication, fluid exchange, power exchange, and so on via one or more support cables, tubes, or the like.

The control system 50 and/or the robotic system 10 can include certain user controls (e.g., controls 55), which may comprise any type of user input (and/or output) devices or device interfaces, such as one or more buttons, keys, joysticks, handheld controllers (e.g., video-game-type controllers), computer mice, trackpads, trackballs, control pads, and/or sensors (e.g., motion sensors or cameras) that capture hand gestures and finger gestures, touchscreens, and/or interfaces/connectors therefore. Such user controls are communicatively and/or physically coupled to the respective control circuitry. In some embodiments, the user may engage the user controls 55 to command robotic shaft articulation, as described herein. Additionally, the control system 50 and/or the robotic system 10 can include one or more power supply interface(s) 219, 259 configured to supply power.

FIG. 4 further shows details of an example articulatable scope assembly/instrument 19 that may be implemented in connection with any of the embodiments of the present disclosure. In some embodiments, the scope assembly 19 includes a handle or base 31 coupled to an endoscope/shaft 40. For example, the endoscope (i.e., "scope" or "shaft") can include an elongate shaft including one or more lights 49 and one or more cameras or other imaging devices, such as a camera 48. In some implementations, the imaging device may be a separate tool outside the scope assembly 19 or a tool releasably attachable to or slidable within the scope 40. The scope 40 can further include one or more working channels 44, which may run a length of the scope 40. The scope assembly 19 can be powered through a power interface 39 and/or controlled through a control interface 38, each or both of which may interface with a robotic arm/component of the robotic system 10. The scope assembly 19 may further comprise one or more sensors 32, such as pressure sensors and/or other force-reading sensors, which may be configured to generate signals indicating forces experienced at/by one or more components of the scope assembly 19.

The scope assembly 19 includes certain mechanisms for causing the shaft 40 to articulate/deflect with respect to an axis thereof. For example, the shaft 40 may have been associated with a proximal portion thereof, one or more drive inputs 34 associated, and/or integrated with one or more pulleys/spools 33 that are configured to tension/untension pull wires 45 of the scope shaft 40 to cause articulation of the shaft 40. The terms "untension" and "de-tension" are used herein according to their broad and ordinary meanings and can refer to a reduction in tension in a wire, cable, line, or similar, and such terms can be used interchangeably.

Figure 5:
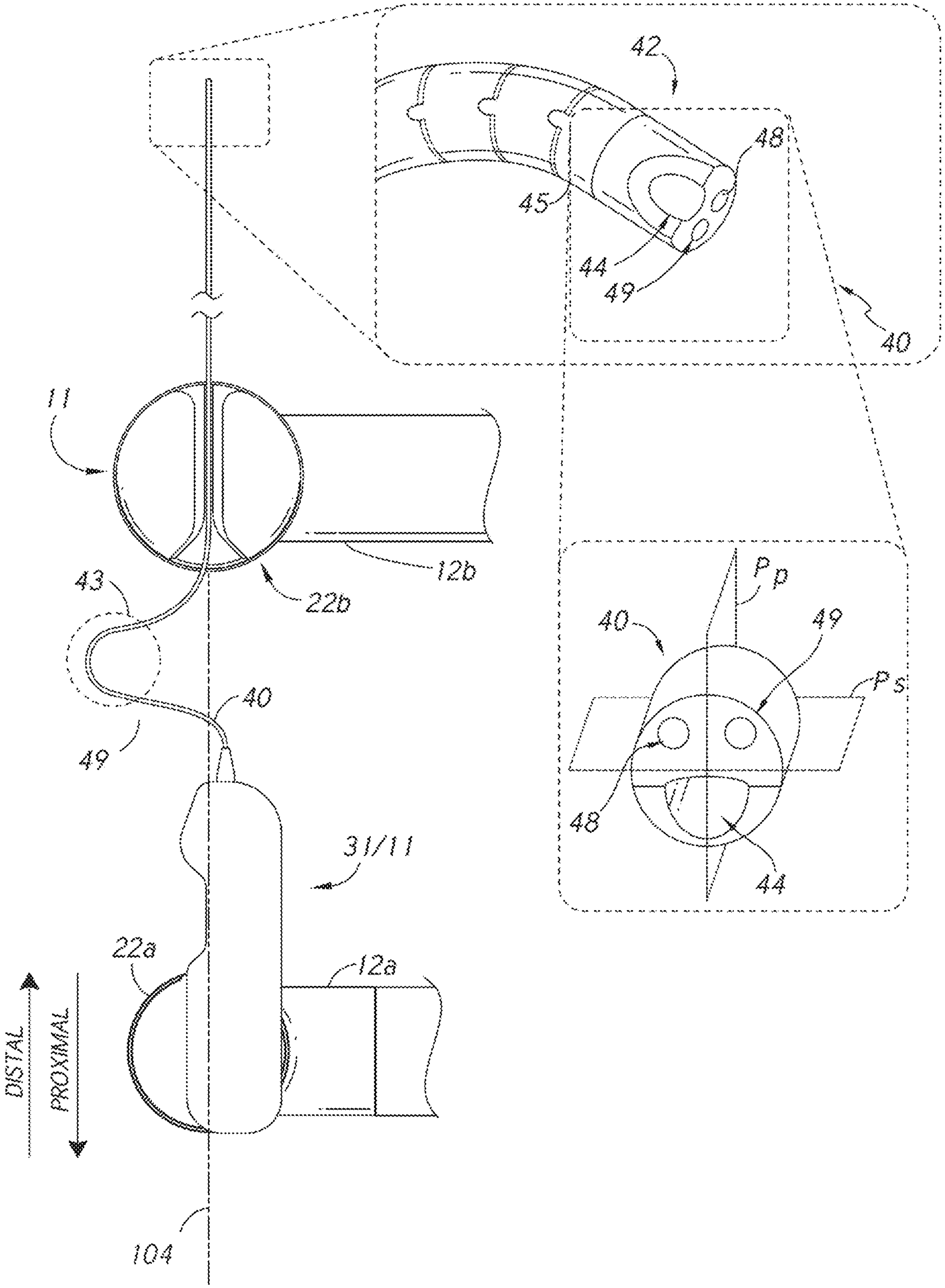
FIG. 5 illustrates an articulatable shaft-type instrument in accordance with one or more embodiments.
Figure 6:
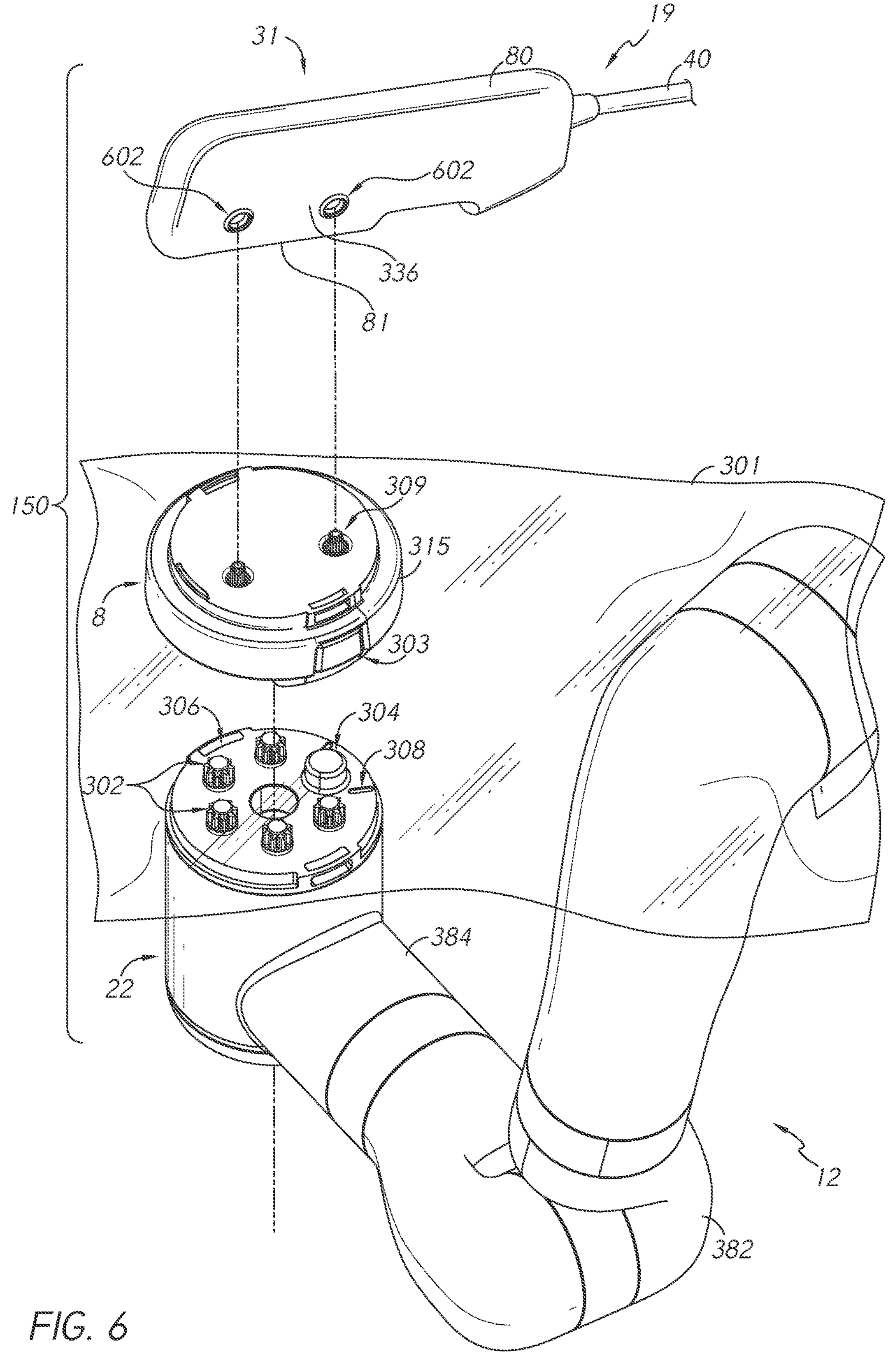
FIG. 6 shows an exploded view of an instrument manipulator assembly associated with a robotic end-effector in accordance with one or more embodiments.

FIG. 5 illustrates a robotically articulatable endoscope 40 coupled to a robotic end effector in accordance with one or more embodiments. FIG. 6 shows an exploded view of an instrument device manipulator assembly 150 associated with the robotic arm 12 in accordance with one or more embodiments. Robotic endoscope control can provide relatively greater precision, control, and/or coordination compared to strictly manual procedures. The description below may be understood in the context of FIGS. 5 and 6, as well as other embodiments presented herein.

The scope/shaft (e.g., endoscope/ureteroscope) 40 may comprise a tubular and flexible medical shaft/instrument that is configured to be inserted into the anatomy of a patient to capture images of the anatomy and to perform certain tasks using one or more working channels thereof. In some embodiments, the scope 40 can accommodate wires and/or optical fibers to transfer signals to/from an optical assembly at a distal end 42 of the scope 40, which can include one or more imaging devices 48, such as optical camera(s). The scope 40 can further include one or more light sources 49, such as LED or fiber-optic light source(s)/lens(es).

The scope 40 can be articulable with respect to at least a distal portion 42 of the scope 40, so that the scope 40 can be steered within the human anatomy. In some embodiments, the scope 40 is configured to be articulated with, for example, six degrees of freedom, including XYZ coordinate movement, as well as pitch, yaw, and roll. Certain position sensor(s) (e.g., electromagnetic sensors) of the scope 40, where implemented, may likewise have similar degrees of freedom with respect to the positional information they generate/provide.

For robotic implementations, robotic arms/rails 12 of a robotic system can be configured/configurable to manipulate the scope 40. For example, an instrument device manipulator (e.g., scope handle) 31 can be coupled to an end effector 22 of a robot arm/rail 12 and can manipulate the scope 40 using elongate movement members. The elongate movement members may include one or more pull wires (e.g., pull or push wires), cables, tendons, fibers, and/or flexible shafts. For example, the robotic end effector may be configured to actuate multiple pull wires (not shown) coupled to the scope 40 to deflect the tip 42 of the scope 40. Pull wires may include any suitable or desirable materials, such as metallic and non-metallic materials such as stainless steel, Kevlar, tungsten, carbon fiber, and the like. In some embodiments, the scope 40 is configured to exhibit nonlinear behavior in response to forces applied by the elongate movement members. The nonlinear behavior may be based on stiffness and compressibility of the scope, as well as variability in slack or stiffness between different elongate movement members. A robotic arm 12 can comprise one or more hinges 382 and/or joints configured to allow extension of a distal portion 384 of the robotic arm 12 in various directions and/or at various angles.

The scope 40 may further be configured to accommodate optical fibers to carry light from proximally located light sources, such as light-emitting diodes, to the distal end 42 of the scope. In some embodiments, the scope 40 is configured to be controlled by a robotic system similar in one or more respects to the systems 100, 101, 103, and 400 shown in FIGS. 1-4, respectively.

In some embodiments, the shaft (e.g., scope) 40 includes a sensor that is configured to generate and/or send sensor position data to another device or produce a detectable distortion or signature in an electromagnetic field. The sensor position data can indicate a position and/or orientation of the medical instrument 40 (e.g., the distal end 42 thereof) and/or can be used to determine/infer a position/orientation of the medical instrument. For example, a sensor (sometimes referred to as a "position sensor") can include an electromagnetic (EM) sensor with a coil of conductive material or other form/embodiment of an antenna.

The instrument base/handle 31 can be configured to attach, mount, or otherwise be connected or coupled to the robotic end effector 22. For example, a robotic arm can include an instrument drive mechanism/assembly 150 comprising an end effector 22 and/or sterile adapter 8, and the instrument base/handle 31, which is attached to the end effector 22 and/or adapter 8. The instrument drive mechanism can include drive outputs 302, 309 configured to engage with and actuate corresponding drive input(s) 602 on the instrument base/handle 31 to manipulate the medical instrument 19. For example, one or more drive outputs 302 of the robotic end effector 22 can be configured to control shaft articulation, as described in detail herein. The drive outputs 302 of the end effector 22 can be coupled to one or more drive couples of an adapter (e.g., sterile adapter) that are configured to transfer drive torque from the drive output(s) 302 of the end effector 22 to drive output(s) 309 of the adapter 8. References herein to a robotic end effector and/or drive output(s) or other features thereof can be understood to refer to an adapter (e.g., sterile adapter) coupled to an end effector and/or drive output(s) of the adapter. For example, description of docking of an instrument on an end effector should be understood to refer to docking the instrument on an adapter when an adapter is coupled to the end effector.

In some configurations, the elongated shaft 40 of the medical instrument 19 is arranged to form a service loop 43 between the instrument handle 31 and an instrument feeder 11 and/or between the associated robotic arms. The service loop 43 may comprise a length of the shaft 40 between the instrument base/handle 31 and the feeder device 11. The service loop 43 can provide slack in the shaft 40 that can be used to allow for faster insertion and/or retraction of the shaft 40. For example, during insertion, the slack in the service loop 49 can be taken up (shortening or contracting the service loop 49). During retraction, the service loop 49 can be generated (increasing in length or expanding).

The scope 40 can be deflectable in one or two directions within a first/primary plane $P_p$. The scope 40 can also be deflectable in one or two directions in a second/secondary plane $P_s$, which may be orthogonal to the primary plane $P_p$. For example, it can be desirable for the at least the distal section 42 of the scope 40 to be deflectable in more than one plane to reach the desired area. Although the primary $P_p$ and secondary $P_s$ deflection planes are shown in a particular configuration, it should be understood that the illustrated secondary plane $P_s$ may be the primary plane $P_p$ and vice versa.

In some embodiments, one or more cables, tendons, pull wires, or pull wire segments can run along the length of the shaft 40. Manipulation/tensioning of the one or more pull wires results in actuation or deflection of the distal section 42 of the scope 40. Manipulation/tensioning of the one or more pull wires can be controlled via one or more instrument drivers/pulleys positioned within or connected to the instrument base/handle 31.

The instrument base/handle 31 can generally include an attachment interface having one or more mechanical drive inputs 602 (e.g., receptacles, pulleys, spools, female inputs, etc.) that are designed to be reciprocally mated with one or more torque couplers on an attachment surface of an instrument driver. The instrument handle 31 can include a plurality of drive inputs 602, each associated with a respective pull wire articulation pulley. The plurality of pull wires can be coupled to the plurality of drive inputs 602 (and corresponding pulleys) and extend along the flexible shaft 40. The plurality of drive inputs 602 can be configured to control or apply tension to the plurality of pull wires in response to rotation of drive outputs 302 of the coupled robotic system.

In order to navigate the scope 40 through the anatomy, the articulation section of the scope 40 can be deflectable in the primary plane $P_p$. A distal section of the articulation section may further be deflectable in two directions within the secondary plane $P_s$. Therefore, the distal portion 42 of the articulation section of the scope 40 can be deflectable in two planes and four directions (e.g., left/right and up/down). The bend radius of the scope 40 may be greater in the primary plane $P_p$ (e.g., up to 270° or more in either direction) than in the secondary plane $P_s$ (e.g., 180° or less in either direction).

In embodiments in which the instrument device manipulator assembly 150 (see FIG. 6) includes an adapter component 8, the adapter 8 may be mountable to the end effector 22 and configured to provide a driver interface between the end effector 22 and the instrument handle 31. The adapter 8 and/or the instrument handle 31 may be removable or detachable from the robotic arm 12 and may be devoid of any electro-mechanical components, such as motors, in some embodiments. This dichotomy may be driven by the need to sterilize medical instruments used in medical procedures and the inability to adequately sterilize expensive capital equipment due to their intricate mechanical assemblies and sensitive electronics. Accordingly, the instrument handle 31 and/or adapter 8 may be designed to be detached, removed, and interchanged from the end effector 22 (and thus the system) for individual sterilization or disposal. In contrast, the end effector 22 need not be changed or sterilized in some cases and may be draped (e.g., using drape 301) for protection. The drape 301 may be coupled to the adapter 8 in such a way as to allow for translation of mechanical torque from the end effector 22 to the adapter 8. The adapter 8 may generally be configured to maintain a seal around the actuating components thereof, such that the adapter 8 provides a sterile barrier itself. With the arm 12 draped in plastic, the physician and/or other technician(s) may interact with the arm 12 and/or other components of the robotic cart (e.g., screen) during a procedure. Draping may further protect against equipment biohazard contamination and/or minimize clean-up after procedure.

In some embodiments, the adapter 8 can include connectors to transfer pneumatic pressure, electrical power, electrical signals, and/or optical signals from the robotic arm 12 and/or end effector 22 to the instrument handle 31. The robotic arm 12 can advance/insert or retract the coupled instrument handle 31 into or out of the treatment site. In some embodiments, the instrument handle 31 can be removed and replaced with a different type of instrument. The end effector 22 of the robotic arm 12 can include various components/elements configured to connect to and/or align with components of the adapter 8, instrument handle 31, and/or shaft 40. For example, the end effector 22 can include drive outputs 302 (e.g., drive splines, gears, or rotatable disks with engagement features) to control/articulate a medical instrument, a reader 304 to read data from the medical instrument 31 (e.g., radio-frequency identification (RFID) reader to read a serial number from a medical instrument), one or more fasteners 306 to attach the instrument handle 31 and/or adapter 8 to the end effector 22, marker(s) 308 to aid in instrument alignment and/or to define a front surface of the device manipulator assembly 150. In some embodiments, a portion (e.g., plate) 315 of the adapter 8 can be configured to rotate/spin independently of one or more other components of the adapter 8 and/or end effector 22 when coupled to the end effector 22. The adapter 8 may be configured to release from the end effector 22 via a release tab 303 and/or similar mechanism.

The instrument handle 31 can include a plurality of drive inputs 602 on a surface 336 of the housing 80 of the instrument handle 31. In the illustrated embodiment, the instrument handle 31 includes two drive inputs 602, although other numbers of drive inputs can be included in other embodiments. The drive inputs can be in fixed positions spaced apart along the mating surface 336 of the instrument handle 31, which facilitates coupling the drive inputs 602 to the corresponding drive outputs 302 of the end effector 22, which may be in fixed positions spaced apart along a corresponding mating surface designed for modular use and attachment to a variety of other instruments. The handle 31 can include latching clips or other latching features/means for physically coupling to corresponding structure of the adapter 8 and/or end effector 22.

A mechanical assembly within the instrument handle 31 can allow the drive inputs 602 to be used to drive articulation of the shaft 40. Each of the drive inputs 602 can be configured to engage with a corresponding drive output 302 on the end effector 22. For example, each drive input can comprise a receptacle configured to mate with a drive output that is configured as a spline. The drive inputs and drive outputs can be configured to engage to transfer motion therebetween. Thus, the drive outputs can be rotated to cause corresponding rotation of the drive inputs to control various functionality of the instrument handle 31.

References herein to an "instrument device manipulator assembly," "instrument manipulator assembly," "manipulator," "manipulator assembly," as well as other variations thereof, can refer to any subset of the components of the assembly 150 shown in FIG. 6, including a robot arm, an end effector of a robot arm, an adapter configured to be coupled to a robotic end effector, an instrument base/handle configured to be coupled to an end effector and/or adapter, and/or other actuator component(s), means, and/or mechanism associated with an instrument base/handle. Furthermore, it should be understood that references herein to an "actuator" can refer to any component of the assembly 150 shown in FIG. 6 that affects or causes, either directly or indirectly, movement of an instrument/component engaged with, coupled to, or otherwise actuatable by, a component of the assembly 150. For example, in accordance with embodiments disclosed here, an "actuator" may comprise any set or subset of the following devices or components: feed roller(s), shaft-actuating wheel(s)/roller(s), feed roller channel(s), instrument feeder drive input(s), adapter drive output(s), adapter drive input(s), pulleys, belts, gears, pegs, pins, end effector drive output(s), and/or structures and/or control circuitry configured to cause actuation of the same. For example, an actuator may be any component, device, or structure configured such that movement thereof causes corresponding movement in another component, device, or structure, whether integrated with or separate from the actuator.

Dual-Wire Pulley

Figure 7:
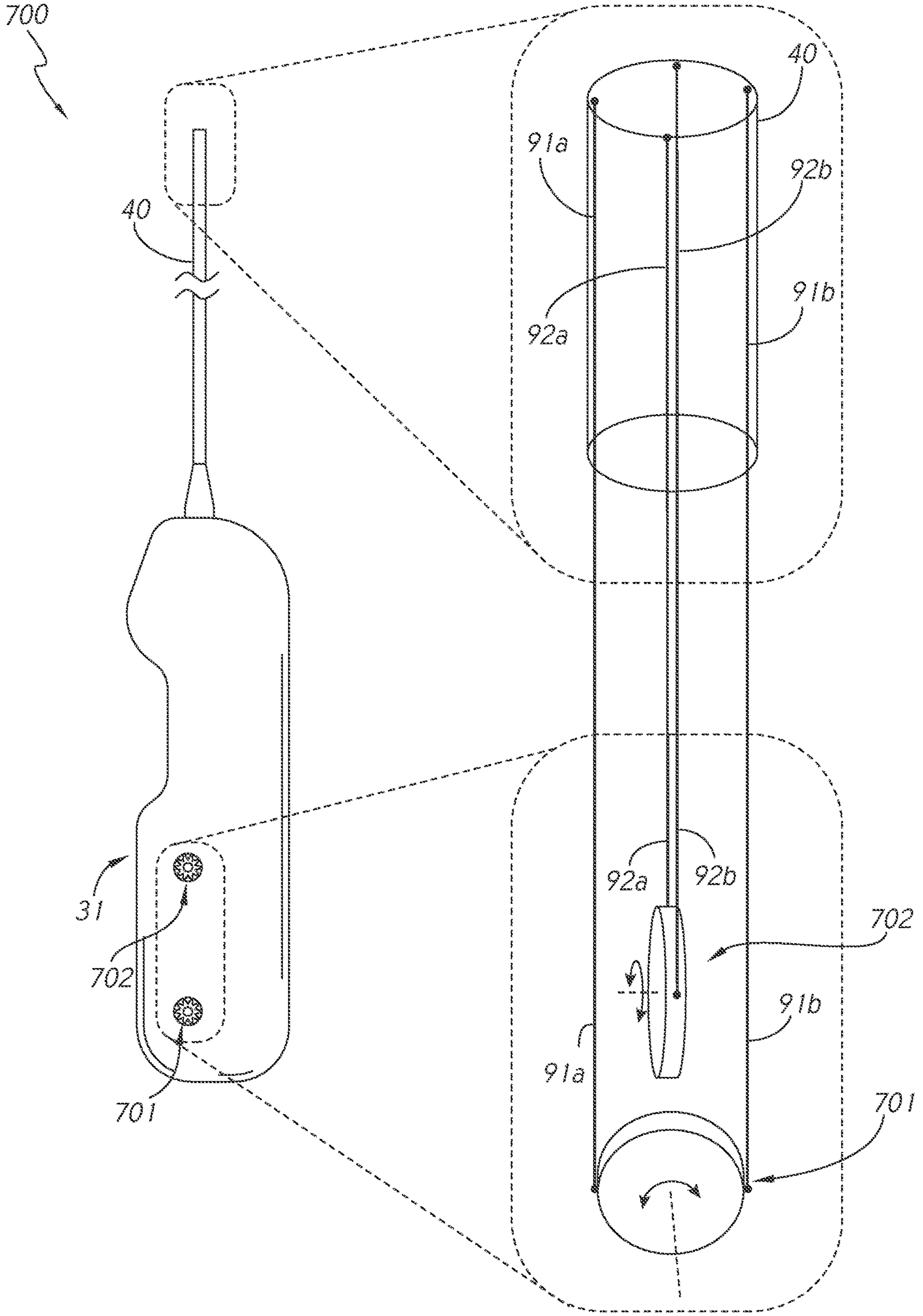
FIG. 7 shows an instrument having one or more dual-wire pulley systems for articulating a shaft of the instrument in accordance with one or more embodiments.

FIG. 7 shows an example instrument having one or more dual-wire pulley systems for articulating a shaft 40 of the instrument in accordance with one or more embodiments. As illustrated, the instrument 700 can include the shaft 40 and a handle 31. The handle 31 can include one or more dual-wire pulleys, such as a first dual-wire pulley 701 and a second dual-wire pulley 702. Each dual-wire pulley 701, 702 can be robotically controlled/rotated with received drive outputs (e.g., the drive output 309 of FIG. 6). In other words, the drive output can provide torque to cause each dual-wire pulley 701, 702 to rotate by a rotational amount. The dual-wire pulleys 701, 702 can be rotated in either clockwise or counterclockwise direction.

As illustrated, the first dual-wire pulley 701 can be configured to have a common rotational axis with a drive output. In some embodiments, the first dual-wire pulley 701 can rotate about on the first/primary plane $P_p$ of FIG. 5. As illustrated, the second dual-wire pulley 702 can be configured to have a rotational axis that is perpendicular to both a rotational axis of the drive output and an axis formed along the shaft 40 and the handle 31. In some embodiments, the second dual-wire pulley 702 can rotate about on the second/secondary plane $P_s$. The handle 31 can employ any known mechanisms to convert a torque/force received from a rotational axis of a drive output to the rotational axis of the second dual-wire pulley 702 and transfer the torque/force.

A first set of pull wires 91 can be attached to the first dual-wire pulley 701. In some embodiments, the first set of pull wires 91 can include a first pull wire 91*a* and a second pull wire 91*b* which may be referred to as an agonist pull wire and an antagonist pull wire, respectively. The first set of pull wires 91 can be coupled to the first dual-wire pulley 701 on opposing sides of the first dual wire pulley 701 such that it is possible to increase the tension on the first pull wire 91*a* via rotation of the first dual-wire pulley 701 without increasing tension on the second pull wire 91*b*, vice versa. For example, as illustrated, the first pull wire 91*a* can be coupled to the 'left' side of the first dual-wire pulley 701 and the second pull wire 91*b* can be coupled to the 'right' side of the first dual-wire pulley 701. Continuing with the illustrated example, counterclockwise rotation of the first dual-wire pulley 701 can pull (e.g., increase a tension on) the first pull wire 91*a* while potentially releasing a tension on the second pull wire 91*b*, vice versa.

Similarly, a second set of pull wires 92 can be attached to the second dual-wire pulley 702. In some embodiments, the second set of pull wires 92 can include a third pull wire 92*a* and a fourth pull wire 92*b* which may be referred to as an agonist pull wire and an antagonist pull wire, respectively. The second set of pull wires 92 can be coupled to the second dual-wire pulley 702 on opposing sides of the second dual wire pulley 701 such that it is possible to increase the tension on the third pull wire 92*a* via rotation of the second dual-wire pulley 702 without increasing tension on the fourth pull wire 92*b*, vice versa. For example, as illustrated, the third pull wire 92*a* can be coupled to the 'back' side of the second dual-wire pulley 702 and the fourth pull wire 92*b* can be coupled to the 'front' side of the second dual-wire pulley 702. Continuing with the illustrated example, the illustrated counterclockwise rotation of the second dual-wire pulley 702 can pull (e.g., increase a tension on) the third pull wire 92*a* while potentially releasing a tension on the fourth pull wire 92*b*, vice versa.

A tip of the shaft 40 can couple to the other ends of the pull wires 91*a*, 91*b*, 92*a*, 92*b*. More specifically, the first pull wire 91*a* and the second pull wire 91*b* of the first set of pull wires 91 can be coupled to opposing ends of the tip on the primary plane $P_P$. Likewise, the third pull wire 92*a* and the fourth pull wire 92*b* of the second set of pull wires 92 can be coupled to opposing ends of the tip on the secondary plane $P_S$. Enlarged views of the shaft 40 and the handle 31 illustrate corresponding attachments of the pull wires 91*a*, 91*b*, 92*a*, 92*b*.

Continuing with the example instrument 700, the tip can be articulated based on pulley rotations of the dual-wire pulleys 701, 702. For instance, to articulate the tip of the shaft 40 to the left, the first dual-wire pulley 701 can be rotated counterclockwise. A rotational force of the first dual-wire pulley 701 pulls the attached first pull wire 91*a* and thereby transfers the rotational force as a tension on the first pull wire 91*a*. The first pull wire 91*a* applies the tension on the other end of the first pull wire 91*a* that is attached to the tip. Simultaneously, the rotational force releases the attached second pull wire 91*b* and thereby enables the tip to more freely incline to a side attached to the first pull wire 91*a*. In combination with the increased tension on the first pull-wire 91*a*, the tip can incline left with the counterclockwise rotation of the first dual-wire pulley 701. In reverse, clockwise rotation of the dual-wire pulley 701 can cause the tip to incline to the right side. Accordingly, rotation of the first dual wire pulley 701 can change inclination of the tip in $P_P$. Similarly, counterclockwise and clockwise rotation of the second dual-wire pulley 702 can be converted to a tension(s) on the second set of pull wires 92 and change inclination of the tip in $P_S$, respectively toward the back of the page and out of the page.

The operations of the dual-wire pulleys 701, 702, resulting in respective changes in inclination of the tip in the respective planes $P_P$ and $P_S$, can be deemed independent of the other. Thus, a combined operation of the dual-wire pulleys 701, 702 can enable articulation of the tip in any direction.

The use of the dual-wire pulleys 701, 702 provides many advantages over a single-wire pulley (not shown). For example, a single-wire pulley having its only pull wire attached to the tip can articulate the tip in only one direction. It requires another pull wire attached to a different single-wire pulley and the tip if the tip is to be articulated in the opposing direction. Thus, bi-directional implementations based on the single-wire pulley requires overheads of an additional single-wire pulley and a corresponding drive output. The overheads can be costly not only in terms of additional pulley and drive output parts needed but also in use of limited physical space in the handle 31. Further, in the single-wire pulley implementations, the single-wire pulleys must be synchronized in tension application (e.g., pull of one pull wire must be accompanied with a release of the other pull wire) or the single-wire pulleys can apply an undesirably elevated tension which may be unsafe to the instrument. In contrast, the example instrument 700 based on the dual-wire pulleys 701, 702 can reduce a total number of drive outputs and greatly simplify synchronization of the sets of pull wires 91, 92.

Dual-Wire Pulley Articulation Responses

Figure 8:
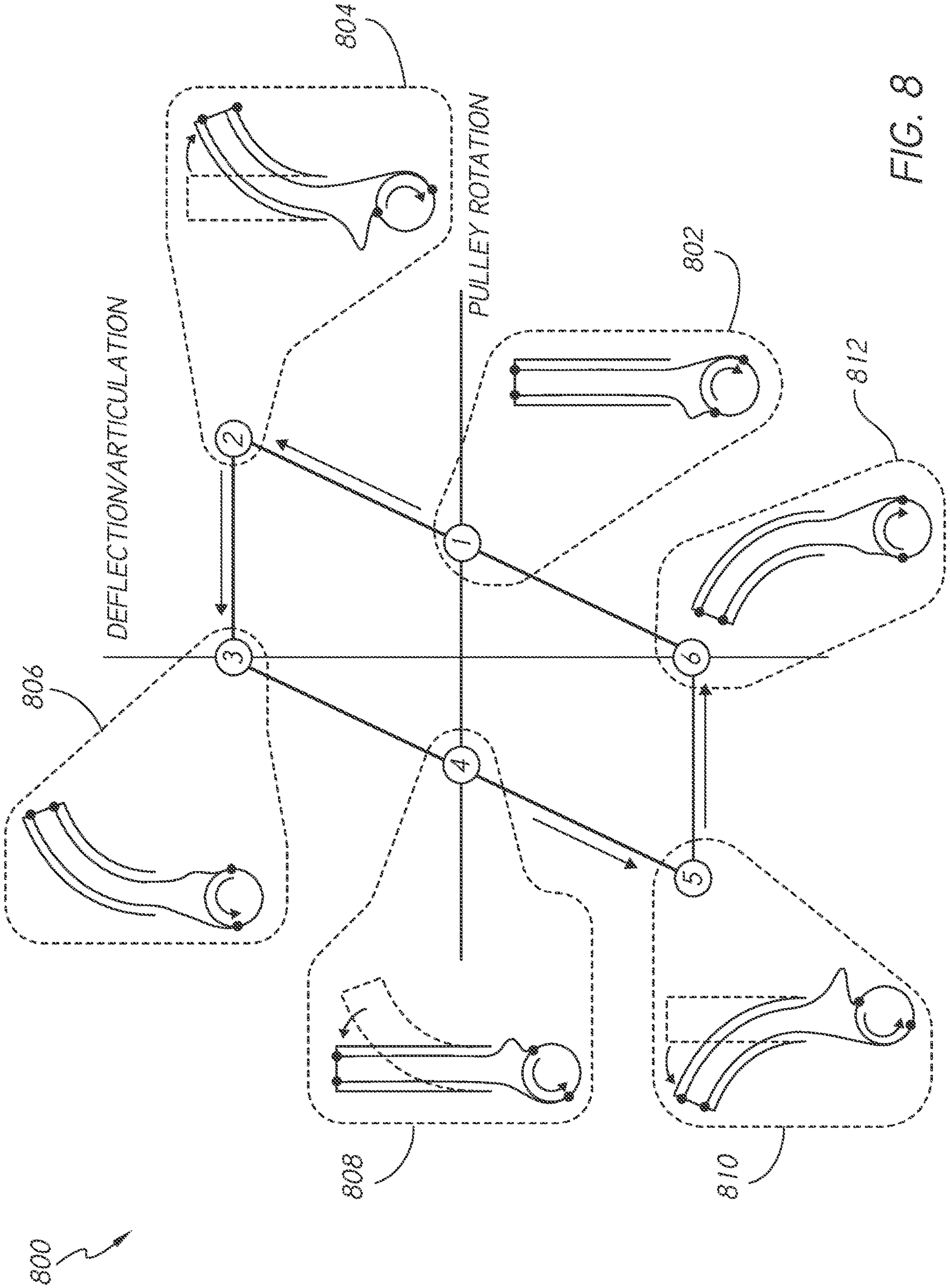
FIG. 8 is a graph showing a relationship between pulley rotation and instrument deflection for a plastic instrument shaft in accordance with one or more embodiments.
Figure 9:
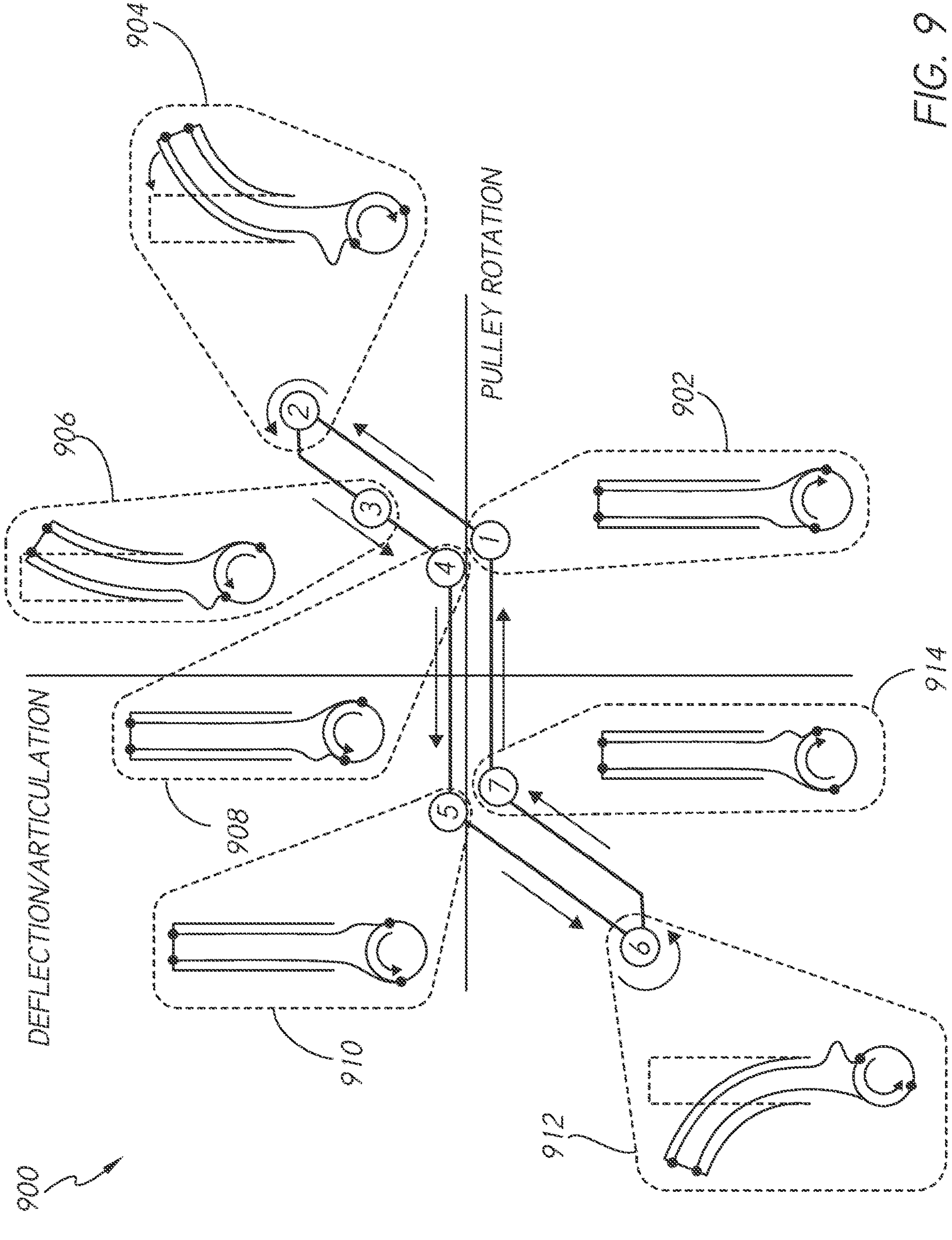
FIG. 9 is a graph showing a relationship between pulley rotation and instrument deflection for an elastic instrument shaft in accordance with one or more embodiments.
Figure 10:
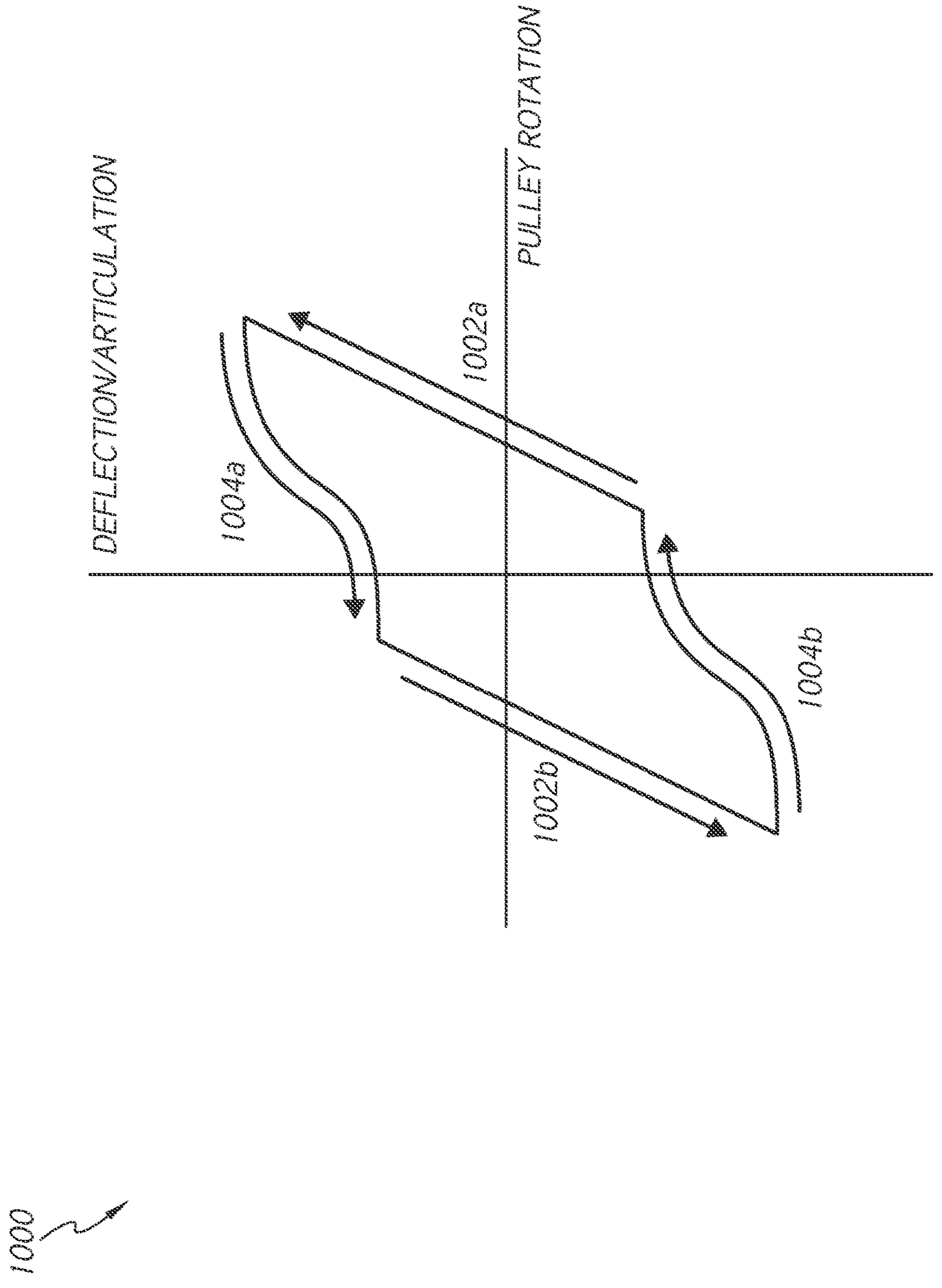
FIG. 10 is a graph showing a relationship between pulley rotation and instrument deflection for a hybrid plastic and elastic instrument shaft in accordance with one or more embodiments.

FIGS. 8-10 are graphs 800, 900, 1000 showing relationships between pulley rotation and instrument deflection/articulation. Each of the graphs 800, 900, 1000 are plotted on a plane having an X-axis that represents pulley rotation (e.g., a rotational amount) and a Y-axis that represents deflection/articulation (e.g., an inclination). The center line on the X-axis can indicate zero rotation of a dual-wire pulley that is rotated neither clockwise nor counterclockwise. Moving toward the right of the center line along the X-axis can indicate increased clockwise rotation while moving toward the left can indicate increased counterclockwise rotation. The center line on the Y-axis can indicate zero inclination of the tip that is neither toward left (e.g., negative inclination) nor right (e.g., positive inclination). Moving toward the top of the center line along the Y-axis can indicate increased rightward inclination while moving toward the bottom can indicate increased leftward inclination. With this understanding, each of the relationships will be described in a counterclockwise traversal of the relationship. It is to be understood that each starting coordinate and the counterclockwise traversal are selected to facilitate the following descriptions and may be deemed arbitrary. Additionally, some aspects of the graphs 800, 900, 1000 may be exaggerated to facilitate the descriptions.

FIG. 8 is a graph 800 showing a relationship between pulley rotation and instrument inclination for a tip of a plastic (e.g., malleable, pliable, flexible, supple, bendable, or the like) instrument shaft in accordance with one or more embodiments. The plastic instrument shaft can be a shaft that exhibits a tendency to remain inclined once positioned in an inclined position. An example of a plastic instrument shaft can be a shaft that is limp and does not return to a neutral position (e.g., zero inclination) on its own.

The relationship will be described in a counterclockwise manner, going from a first configuration 802 to a second configuration 804, a third configuration 806, a fourth configuration 808, a fifth configuration 810, a sixth configuration 812, and returning to the first configuration 802.

The first configuration 802 is plotted at a clockwise (e.g., positive) pulley rotation and zero inclination. At the first configuration 802, the left pull wire (e.g., the first pull wire 91*a* of FIG. 7) has zero or an insubstantial amount of tension while the right pull wire (e.g., the second pull wire 91*b* of FIG. 7) is taut based on the clockwise pulley rotation. Here, the traversal is about to start toward the second configuration 804. In other words, the tip is about to incline towards a rightward direction.

The second configuration 804 is plotted at an increased clockwise pulley rotation and a rightward inclination. Between the first configuration 802 and the second configuration 804, an increase in tension on the right pull wire causes a linear increase in the rightward inclination. While the right pull wire has increased tension compared to the first configuration 802, the left pull wire remains with zero or an insubstantial amount of tension.

The third configuration 806 is plotted at the zero pulley rotation and the rightward inclination. Between the second configuration 804 and the third configuration 806, counterclockwise pulley rotation steers pulley rotation toward zero and correspondingly decreases tension on the right pull wire. However, the counterclockwise pulley rotation does not alter the rightward inclination previously articulated at the second configuration 804. As illustrated, the flat (e.g., parallel to the X-axis) response between the second configuration 804 and the third configuration 806 indicates a constant inclination of the tip. The lack of inclination response during the traversal between the second configuration 804 and the third configuration 806 may be observed when both the left pull wire and the right pull wire are loose (e.g., without meaningful tension) and, therefore, unable to adjust the inclination. As the plastic instrument shaft is limp and does not return to its neutral position on its own, no change in inclination is observed during the traversal here.

When the traversal reaches the third configuration 806, the left pull wire becomes taut based on the counterclockwise pulley rotation. Here, the traversal is about to start toward the fourth configuration 808. In other words, the tip is about to start inclining toward leftward from its rightward inclination.

The fourth configuration 808 is plotted at a counterclockwise (e.g., negative) pulley rotation and the zero inclination. At the fourth configuration 808, the left pull wire is taut while the right pull wire has zero or an insubstantial amount of tension based on the counterclockwise pulley rotation.

The fifth configuration 810 is plotted at an increased counterclockwise pulley rotation and a leftward inclination. Between the third configuration 806 and the fifth configuration 810, an increase in tension on the left pull wire causes a linear increase in the leftward inclination. The right pull wire remains with zero or an insubstantial amount of tension.

The sixth configuration 812 is plotted at the zero pulley rotation and the leftward inclination. Between the fifth configuration 810 and the sixth configuration 812, clockwise pulley rotation steers pulley rotation toward zero and correspondingly decreases tension on the left pull wire. However, the clockwise pulley rotation does not alter the leftward inclination previously articulated at the fifth configuration 810. As illustrated, the flat (e.g., parallel to the X-axis) response between the fifth configuration 810 and the sixth configuration 812 indicates a constant inclination of the tip. The lack of inclination response during the traversal between the fifth configuration 810 and the sixth configuration 812 may be observed when both the left pull wire and the right pull wire are loose (e.g., without meaningful tension) and, therefore, unable to adjust the inclination. As the plastic instrument shaft is limp and does not return to its neutral position on its own, no change in inclination is observed during the traversal here.

When the traversal reaches the sixth configuration 812, the right pull wire becomes taut based on the clockwise pulley rotation. Here, the traversal is about to return toward the first configuration 802. In other words, the tip is about to start inclining toward right from its leftward inclination.

As shown, the plastic instrument shaft may exhibit at least two traversal zones/regions, between the second configuration 804 and the third configuration 806 and between the fifth configuration 810 and the sixth configuration 812, that exhibit unaltered inclinations even when supplied changes in pulley rotation. The zones are flat (or near flat) in the graph 800 due to their lack of changes in Y-axis in response to changes in X-axis. These flat zones can be considered as 'dead zones' in which the plastic instrument shaft may remain unresponsive to some amount of pulley rotation.

FIG. 9 is a graph 900 showing a relationship between pulley rotation and instrument inclination for a tip of an elastic (e.g., stiff, resilient, rigid, or the like) instrument shaft in accordance with one or more embodiments. The elastic instrument shaft can be a shaft that exhibits a tendency to return to its pre-inclination position when inclined. An example of an elastic instrument shaft can be a shaft that is stiff and returns to a neutral position (e.g., zero-degree inclination) on its own.

The relationship will be described in a counterclockwise manner, going from a first configuration 902 to a second configuration 904, a third configuration 906, a fourth configuration 908, a fifth configuration 910, a sixth configuration 912, a seventh configuration 914, and returning to the first configuration 902.

The first configuration 902 is plotted at a clockwise (e.g., positive) pulley rotation and zero inclination. At the first configuration 902, the left pull wire (e.g., the first pull wire 91*a* of FIG. 7) has zero or an insubstantial amount of tension while the right pull wire (e.g., the second pull wire 91*b* of FIG. 7) is taut based on the clockwise pulley rotation. Here, the traversal is about to start toward the second configuration 904. In other words, the tip is about to incline towards a rightward direction.

The second configuration 904 is plotted at an increased clockwise pulley rotation and a rightward inclination. Between the first configuration 902 and the second configuration 904, an increase in tension on the right pull wire causes a linear increase in the rightward inclination. While the right pull wire has increased tension compared to the first configuration 902, the left pull wire remains with zero or an insubstantial amount of tension.

The third configuration 906 is plotted after applying some counterclockwise pulley rotation during the rightward inclination. Here, as the shaft is stiff and exhibits a tendency to return to the neutral position, the right pull wire is taut and fighting against the tendency of the tip. The rightward inclination continues to be proportional to the total clockwise pulley rotation (e.g., the pulley rotation is to the right of the X-axis center line) and the tension on the right pull wire. The left pull wire has zero or insubstantial tension.

The fourth configuration 908 and the fifth configuration 910 are plotted over a range of pulley rotations that provide the neutral position. Between the fourth configuration 906 and the fifth configuration 908, any clockwise or counterclockwise pulley rotation is overcome by the elastic tendency of the shaft so that the shaft remains at the neutral position. In some embodiments, the pulley rotation within the range may not provide a threshold tension level required to cause the tip to incline. In some embodiments, the left pull wire and the right pull wire may provide zero or some insubstantial tension so that the elastic tendency fully controls the tip to return to the neutral position. In any event, the tip will only leftward incline when provided a counterclockwise pulley rotation that is to the left of the fifth configuration 910 and only rightward incline when provided a clockwise pulley rotation that is to the right of the first configuration 902. Referring again to the counterclockwise traversal of the graph 900, at the fifth configuration 910, a counterclockwise pulley rotation has not yet caused the leftward incline.

The sixth configuration 912 is plotted at an increased counterclockwise pulley rotation and a leftward inclination that is a mirror image of the second configuration 904. Between the fifth configuration 910 and the sixth configuration 912, an increase in tension on the left pull wire causes a linear increase in the leftward inclination. The right pull wire remains with zero or an insubstantial amount of tension.

From the sixth configuration 912 to the seventh configuration 914, clockwise pulley rotation is applied. Here, as the shaft is stiff and exhibits a tendency to return to the neutral position, the left pull wire is taut and fighting against the tendency of the tip. The leftward inclination continues to be proportional to the total counterclockwise pulley rotation (e.g., the pulley rotation is to the left of the X-axis center line) and the tension on the left pull wire. In the meanwhile, the right pull wire has zero or insubstantial tension.

At the seventh configuration 914, the tip reaches the neutral position again due to its elastic tendency. There until the first configuration 902, any clockwise or counterclockwise pulley rotation is overcome by the elastic tendency of the shaft so that the shaft remains at the neutral position. Here, the elastic instrument shaft behaves in a similar manner with its behavior between the fourth configuration 908 and the fifth configuration 910.

As shown, the elastic instrument shaft may exhibit at least two traversal zones/regions, between the fourth configuration 908 and the fifth configuration 910 and between the seventh configuration 914 and the first configuration 902, that exhibit unaltered inclinations even when supplied changes in pulley rotation. The zones are flat (or near flat) in the graph 900 due to their lack of changes in Y-axis in response to changes in X-axis. These flat zones can be considered as 'dead zones' in which the elastic instrument shaft may remain unresponsive to some amount of pulley rotation.

FIG. 10 is a graph 1000 showing a relationship between pulley rotation and instrument deflection for a hybrid (both plastic and elastic) instrument shaft in accordance with one or more embodiments. The hybrid instrument shaft can be desirably plastic and elastic. In other words, a tip of the hybrid instrument shaft can have a tendency, unlike the plastic instrument shaft, to return to its neutral position on its own but less so than that of the elastic instrument shaft. Accordingly, the hybrid instrument shaft can combine, or take into consideration, response profiles exhibited by various different materials to provide a response profile that is more desirable or optimal for a particular application. Further, the hybrid instrument shaft may better model articulation behavior of real-life instrument shafts.

In contrast with previous relationships regarding plastic and elastic instrument shafts, the relationship of the hybrid instrument shaft has linear regions 1002 and nonlinear regions 1004. The linear regions 1002 can include a clockwise linear region 1002*a* and a counterclockwise linear region 1002*b*. Within the linear regions 1002, pulley rotation can cause a proportional inclination associated with slopes of their respective lines.

The nonlinear regions 1004 can include a first nonlinear region 1004*a* and a second nonlinear region 1004*b*. As illustrated, the nonlinear regions 1004 connect the clockwise linear region 1002*a* and the counterclockwise linear region 1002*b*. In other words, a tip of the hybrid instrument shaft can traverse the first nonlinear region 1004*a* when reversing its dual-wire pulley rotational direction from clockwise to counterclockwise. Similarly, the tip of the hybrid instrument shaft can traverse the second nonlinear region 1004*b* when reversing its dual-wire pulley rotational direction from counterclockwise to clockwise.

Curves of the first and second nonlinear regions 1004*a*, 1004*b* illustrate little to no dead zones. Accordingly, the tip of the hybrid instrument shaft remains responsive to any change in pulley rotation. Furthermore, as the hybrid instrument shaft is neither too wobbly nor too stiff, it can reduce operator frustration and, in some instances, improve instrument durability.

Kinematic Model

The hybrid instrument shaft and its articulation response to pulley rotation can be represented based on a kinematic model. The kinematic model can estimate a relationship between pulley rotation and corresponding endoscope articulation (e.g., deflection/inclination) in a plane. Based on the relationship, the kinematic model can enable determination of a resulting articulation provided a given pulley rotation. In reverse, the kinematic model can enable determination of a predicted pulley rotation for a desired articulation. Where the kinematic model is concerned, determination of an articulation, a pulley rotation, an articulation response, or any regions thereof can be synonymously described as estimation, computation, calculation, or identification.

In some embodiments, the kinematic model can be a mathematical model that represents the articulation response in terms of formulas. Such a mathematical kinematic model can advantageously enable computation of the resulting articulation or the predicted pulley rotation. The formulas may rely on following example parameters and variables to represent the articulation response:

TABLE 1

Parameter and variable definitions used in the kinematic model

| Symbol | Definition |
|---|---|
| $\Phi$ | Articulation/deflection in a plane (e.g., a pulley plane) |
| j | Pulley rotation |
| $k_{flex}$ | Slope of linear articulation section |
| $k_{relax}$ | Slope of linear de-articulation section |
| dz0 | Center dead zone |
| C, Q, B, nu | Parameters defining a generalized logistic function |
| $(.)_{cmd}$ | Appendix to indicate 'commanded' (e.g., $j_{cmd}$ is commanded pulley rotation) |
| $(.)_{@EoS}$ | Appendix to indicate 'state at end of sigmoid/ transition region' |
| $(.)_{@Reversal}$ | Appendix to indicate 'state at reversal' |
| $j_c$ | Midpoint between reversal and EoS |

Depending on formulas used to represent the articulation response, there may be additional or fewer parameters and variables than shown in Table 1.

Figure 11A:
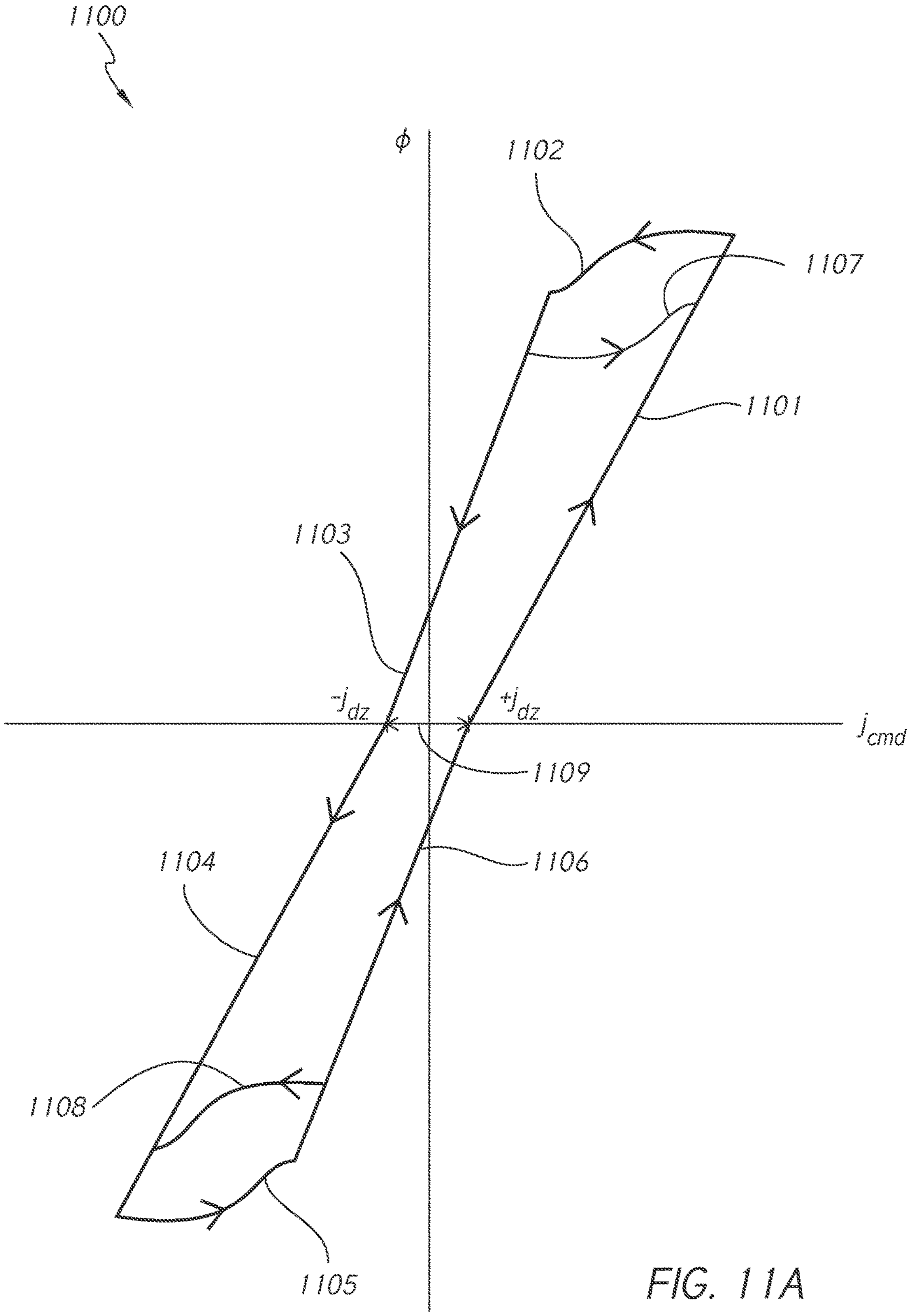
FIGS. 11A-11B are a kinematic model and a tension response in accordance with one or more embodiments.

FIG. 11A is a kinematic model 1100 of a hybrid instrument shaft showing a relationship between pulley rotation and instrument deflection in accordance with one or more embodiments. The kinematic model 1100 is plotted on a plane having an X-axis that represents commanded pulley rotation (denoted $j_{cmd}$) and a Y-axis that represents deflection (denoted $\phi$).

The kinematic model 1100 can be formulated using a combination of linear and nonlinear piecewise continuous functions. Specifically, the kinematic model can include eight articulation response regions: four linear regions (e.g., a first linear region 1101, a second linear region 1103, a third linear region 1104, and a fourth linear region 1106) and four nonlinear regions (e.g., a first nonlinear region 1102, a second nonlinear region 1105, a third nonlinear region 1107, and a fourth nonlinear region 1108). The kinematic model 1100 plots the linear regions and the nonlinear regions can be defined (e.g., determined) based at least in part on a pulley rotation, as shown on the X-axis, and an associated articulation, as shown on the Y-axis. The articulation response can be linear when either pull wire is in tension and, thus, linear functions can model the endoscope response during articulation in the first linear region 1101 or the third linear region 1104 and de-articulation in the second linear region 1103 or the fourth linear region 1106. Articulation in the first linear region 1101 or the third linear region 1104 is when the endoscope deflects and continues to deflect toward a direction from a neutral position. De-articulation in the second linear region 1103 or the fourth linear region 1106 is when the endoscope returns to the neutral position from its previous deflection. The response is nonlinear during tension transitions from a pull wire to another pull wire (e.g., an agonist wire to an antagonist wire). The tension transitions can occur during direction reversals. Nonlinear functions can model the endoscope response during reversals (e.g., when changing from articulation to de-articulation or vice versa) in the first nonlinear region 1102, the second nonlinear region 1105, the third nonlinear region 1107, or the fourth nonlinear region 1108. Articulation reversals in the first nonlinear region 1102 or the second nonlinear region 1105 may occur at any instant during the articulation in the first linear region 1101 or the third linear region 1104 and the de-articulation reversals in the third nonlinear region 1107 or the fourth nonlinear region 1108 may occur at any instant during the de-articulation in the second linear region 1103 or the fourth linear region 1106. In some embodiments, sigmoid functions can be used to model the articulation response during the reversals in the first nonlinear region 1102, the second nonlinear region 1105, the third nonlinear region 1107, or the fourth nonlinear region 1108. More specifically, generalized logistic functions can be used to model the articulation response.

The kinematic model 1100 includes one or more "dead zones," where pulley rotation does not readily result in endoscope articulation. The dead zone may occur because of various instrument properties, such as friction in endoscope mechanisms, anatomy of the endoscope, material properties, pulley properties, component wear, or the like. An example dead zone is the center dead zone 1109 in which pulley rotation above a positive threshold level (denoted $+j_{dz}$) or below a negative threshold level (denoted $-j_{dz}$) must be satisfied before a neutrally positioned endoscope is deflected. That is, pulley rotation within the center dead zone 1109 does not deflect the neutrally positioned endoscope.

Figure 11B:
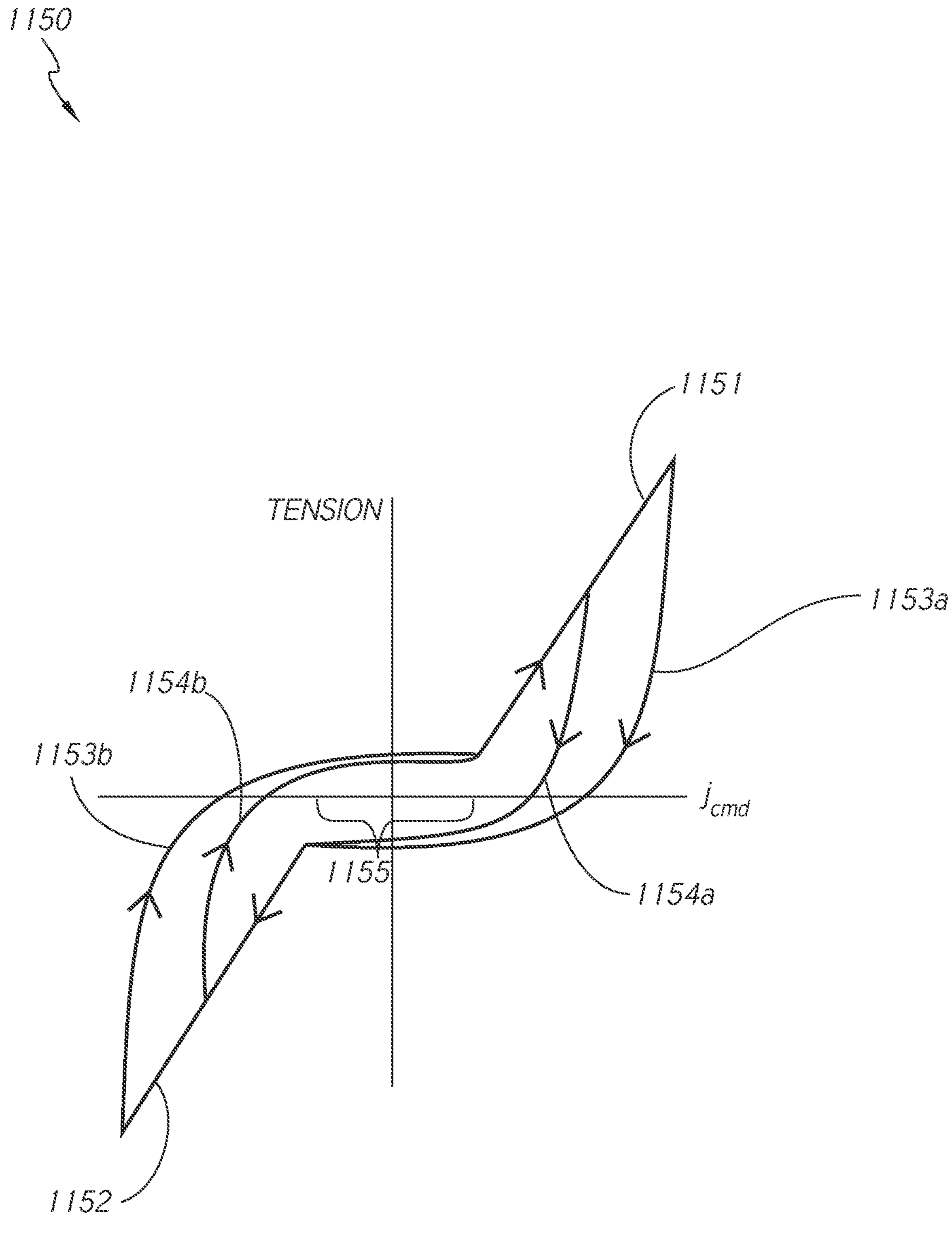

FIG. 11B is a tension response 1150 of a hybrid instrument shaft showing a relationship between pulley rotation and applied tension in accordance with one or more embodiments. The tension response 1150 is plotted on a plane having an X-axis that represents pulley rotation (denoted $j_{cmd}$) and a Y-axis that represents net tension on a pair of pull wires.

Much like the kinematic model, the tension response shows a combination of linear regions and nonlinear regions. Specifically, the tension response shows six regions: two linear tension regions 1151, 1152 and four nonlinear tension regions 1153*a*, 1153*b*, 1154*a*, 1154*b*. The tension response is linear when either pull wire is in tension. For example, a positive net tension (e.g., a first pull wire causes tension) within a first linear tension region 1151 and an endoscope articulation in a first direction. The positive net tension can cause the articulation in the first linear region 1101 and the de-articulation in the fourth linear region 1106 of the kinematic model 1100 in FIG. 11A. Similarly, a negative net tension (e.g., a second pull wire causes tension) within a second linear tension region 1152 and an endoscope articulation in a second direction, opposite the first direction. The negative net tension can cause the de-articulation in the second linear region 1103 and the articulation in the third linear region 1104 of the kinematic model 1100.

The tension is nonlinear during reversals associated with the nonlinear tension regions 1153*a*, 1153*b*, 1154*a*, 1154*b*. For example, a first reversal associated with a first nonlinear tension region 1153*a* may occur at an instant a dual-wire pulley starts to rotate counterclockwise from a maximum clockwise pulley rotation. The instant of the first reversal associated with the first nonlinear tension region 1153*a* can correspond to the top of the articulation in the first linear region 1101 of the kinematic model 1100. As the pulley continues to rotate counterclockwise, the first pull wire loses tension, resulting in decreased absolute net tension as illustrated during the reversal associated with the first nonlinear tension region 1153*a*. Eventually, the second pull wire starts to provide a negative net tension over the second linear tension region 1152 for the de-articulation in the second linear region 1103 and the articulation in the third linear region 1104 of the kinematic model 1100. In reverse, a second reversal associated with a second nonlinear tension region 1153*b* may occur at an instant the dual-wire pulley starts to rotate clockwise from a maximum counterclockwise pulley rotation. The instant of the second reversal associated with the first nonlinear tension region 1153*b* can correspond to the bottom of the articulation in the third linear region 1104 of the kinematic model 1100. As the pulley continues to rotate clockwise, the second pull wire loses tension, resulting in decrease in absolute net tension as illustrated during the reversal associated with the second nonlinear tension region 1153*b*. Eventually, the first pull wire starts to provide a positive net tension over the first linear tension region 1151 for the de-articulation in the fourth linear region 1106 and the articulation in the first linear region 1101 of the kinematic model 1100.

In some instances, a reversal may occur before the maximum pulley rotations. For example, a third reversal associated with a third nonlinear tension region 1154*a* may occur before the dual-wire pulley is at the maximum clockwise pulley rotation. Similarly, a fourth reversal associated with a fourth nonlinear tension region 1154*b* may occur before the dual-wire pulley is at the maximum counterclockwise pulley rotation. Tension responses of the third reversal associated with the third nonlinear tension region 1154*a* and the fourth reversal associated with the fourth nonlinear tension region 1154*b* are illustrated.

The tension response 1150 provides some insight into workings of dead zones, such as the center dead zone 1109 of the kinematic model 1100. During the tension transition from a pull wire to another pull wire during reversals, a range of pulley rotations 1155 may provide minimal tension (or minimal net tension) on the pull wires. Furthermore, during the range of pulley rotations 1155, there may be little to no change in the tension (or net tension). Thus, when in the range of pulley rotations 1155, clockwise or counterclockwise rotation of a dual-wire pulley is unlikely to cause endoscope deflections and contribute to formation of the dead zones.

It is noted that some aspects of the kinematic model 1100 and the tension response 1150 may be exaggerated to facilitate descriptions. For simplicity, the relationships in the kinematic model 1100 and the tension response 1150 are limited to a single dual-wire pulley setup. However, it is understood that modelling of a multiple dual-wire pulley setup can expand the relationships in the kinematic model 1100 and the tension response 1150 with an additional dimension for each additional dual-wire pulley without much difficulty.

The above described kinematic model 1100 and the tension response 1150 can be mathematically modeled using the parameters and variables of Table 1. First, the articulations in the first linear region 1101 or the third linear region 1104 can be modeled as:

$$\phi = k_{flex}(j_{cmd} - j_{dz0}). \quad \text{(Eq. 1)}$$

Second, the de-articulations in the second linear region 1103 or the fourth linear region 1106 can be modeled as:

$$\phi = j_{cmd} + k_{relax} + \text{constant.} \qquad \text{(Eq. 2)}$$

The articulation equation Eq. 1 and the de-articulation equation Eq. 2 are linear in nature and, hence, they are easily invertible.

Finally, the reversals of the first nonlinear region 1102, the second nonlinear region 1105, the third nonlinear region 1107, or the fourth nonlinear region 1108 can be modeled as:

$$\phi = \phi_{@\,EoS} + \frac{\phi_{@\,Reversal} - \phi_{@\,EoS}}{(C + Q \cdot \exp(-B \cdot f(j_{cmd})))^{1/nu}} \qquad \text{(Eq. 3)}$$

$$\text{where, } f(j_{cmd}) = \tan\left[\frac{\pi}{j_{@\,Reversal} - j_{@\,EoS}}(j - j_c)\right],\ j_c = \frac{(j_{@\,Reversal} - j_{@\,EoS})}{2}.$$

The reversal equation Eq. 3 is nonlinear in nature. While it is possible to model the reversals of the first nonlinear region 1102, the second nonlinear region 1105, the third nonlinear region 1107, or the fourth nonlinear region 1108 with a variety of nonlinear functions, the reversal equation Eq. 3 is selected to be a sigmoid using a generalized logistic function with advantageous properties. In general, nonlinear equations are not very straightforward to invert. In contrast, the reversal equation Eq. 3 is invertible and, furthermore, the inverted reversal equation has a unique solution. As will be described in greater detail, the straightforward invertibility makes the reversal equation Eq. 3 preferable compared to other nonlinear equations which are seldom not invertible or have closed form solutions.

Based on the equations Eq. 1, Eq. 2, and Eq. 3, all the linear regions and nonlinear regions in the kinematic model 1100 can be mathematically described. However, the kinematic model 1100 may need to be fitted for each individual endoscope (e.g., the individual endoscope may need to be calibrated to the kinematic model 1100). Parameters can include, for example, $k_{flex}$, $j_{dz0}$, Q, B, and nu, which can depend on manufacturing tolerances and may vary with each endoscope.

The variations can be due to many factors including part and assembly tolerances unique to each endoscope and cause the endoscope to respond differently to articulation commands (e.g., pull-wire commands). Endoscopes are flexible, soft and compliant mechanisms driven by cables (e.g., pull-wire cables) and mechanical characterization of the endoscopes can be essential for understanding endoscope motion, modeling endoscope behavior, developing control algorithms, making mechanical design decisions, and/or testing durability of the endoscope. Without characterizing the impact of these differences on the response of endoscopes, it can be challenging to control the endoscopes accurately and responsively, especially when trying to do so robotically.

Calibration can help characterize the differences for each endoscope. A method to characterize and calibrate an endoscope is described below. The method can characterize input to output behavior of each endoscope by using measured endoscope tip positions as basis for controlling articulation of the endoscope.

The method can involve a setup that can consist of a fixture to mount and hold an endoscope, mechanism(s)/sensor(s) to rotate and measure positions of the individual pulley shafts of the endoscope, mechanism(s)/sensor(s) to measure pull-wire displacement and tension, and/or mechanism(s)/sensor(s) to measure articulation (e.g., tip positions/orientation) of the endoscope. In some embodiments, a tip of an endoscope can be controlled by one or more pulleys attached to one or more pulley shafts. For example, the tip can be controlled by four pulleys attached to either two or four pulley shafts.

With the setup, some or all of the following steps can be performed to characterize the endoscope response:

1. An endoscope can be mounted in the setup and coupled to various input mechanisms.
2. Some sensors can be used to measure a starting/reference position of the one or more pulley shafts and the endoscope tip position/orientation in two/three-dimensional space can be recorded using other sensors (e.g., an EM sensor, an image sensor, and/or any other sensor).
3. Starting from the starting/reference position, the tip can be articulated by rotating the pulley shaft while continuously measuring/sampling pulley rotation, pull wire tension, and endoscope articulation. In some embodiments, for single wire movement characterization, a single pulley shaft can be rotated to articulate the tip while measuring the tip position/orientation using the tip position/orientation measurement sensor. In some embodiments, for a two-wire movement characterization, two pulley shafts can be rotated simultaneously by a fixed amount or by a predetermined ratio between the two pulley shafts. The step can be repeated until the endoscope reaches all of predetermined articulation targets and all the input combinations desired.
4. After the above input-output (e.g., articulation) data collected process, visualizations can be generated from the collected data. An articulation response (e.g., a V-plot, an I-plot, etc.) can be generated by plotting pulley rotation and endoscope tip articulation on a plane, such as on an X-axis and a Y-axis, or vice versa. A force/tension response (e.g., a V-plot, an I-plot, etc.) can be generated by plotting pull wire tension and endoscope tip articulation on a plane, such as on an X-axis and a Y-axis, or vice versa. FIGS. 11A-11B illustrate example articulation and tension responses, respectively.

The plotted responses can enable measurements of some endoscope specific mechanical characteristics including: the center dead zone, articulation and de-articulation slopes, direction reversal transition regions, and direction reversal deadzone(s). These features are described in relation to FIGS. 11A-11B. Based on the measurements and the equations, the endoscope can be calibrated. That is, for example, $k_{flex}$, $j_{dz0}$, Q, B, and nu, that adjust/fit a kinematic model for the endoscope can be determined.

With calibration, the endoscope-specific parameters can be determined for each endoscope. In some embodiments, the calibration parameters can be encoded on a scannable medium and affixed on an endoscope. For example, the parameters can be programmed in an RFID tag inserted in the endoscope or printed on a QR code printed material attached to the endoscope. A reader (e.g., a reader 304 of FIG. 6) may scan the parameters and accordingly fit the kinematic model 1100 to the endoscope. Once calibrated, the endoscope can be robotically controlled, such as determining predicted pulley rotation to effectuate a desired articulation, based on the fitted kinematic model.

In addition to the parameters, the equations Eq. 1, Eq. 2, and Eq. 3 can also depend on variables. The variables can include, for example, $k_\phi$, $k_j$, $\phi_{offset}$, $\phi_{@EoS}$, $\phi_{@Reversal}$, $j_{@EoS}$, $j_{@Reversal}$, $j_c$, and $j_{cmd}$. Some of the variables, such as reversal variables (e.g., $(\bullet)_{@Reversal}$ variables) may be determined at an instant specific to a reversal. For example, the reversal variables can capture specific articulation and pulley rotation at the instant of the reversal. The reversal variables can indicate an endoscope state at the instant including on which linear region the endoscope was traversing before the reversal. Some other variables, such as end of sigmoid variables (e.g., $(\bullet)_{@EoS}$ variables), can be computed. For example, end of sigmoid deflection ($\phi_{@EoS}$) and pulley rotation ($j_{@EoS}$) can be computed based on:

$$\phi_{@\,EoS} = k_\phi \phi_{@\,Reversal} - \phi_{offset} \quad \text{(Eq. 4)}$$

and, $$j_{@\,EoS} = \frac{j_{@\,Reversal}}{k_j} - j_{dz0}. \quad \text{(Eq. 5)}$$

Based on the parameters and variables, the kinematic model 1100 can be fitted for any endoscope and describe its current state with the equations Eq. 1, Eq. 2, and Eq. 3. Since all the equations are invertible and provide a unique solution given an endoscope state, a predicted pulley rotation to effectuate a desired or commanded deflection can be easily computed by solving the inverted equations. Such kinematic model can be received, computed, or otherwise acquired by a robotic cart/system and/or control tower/system of the present disclosure.

Figure 12:
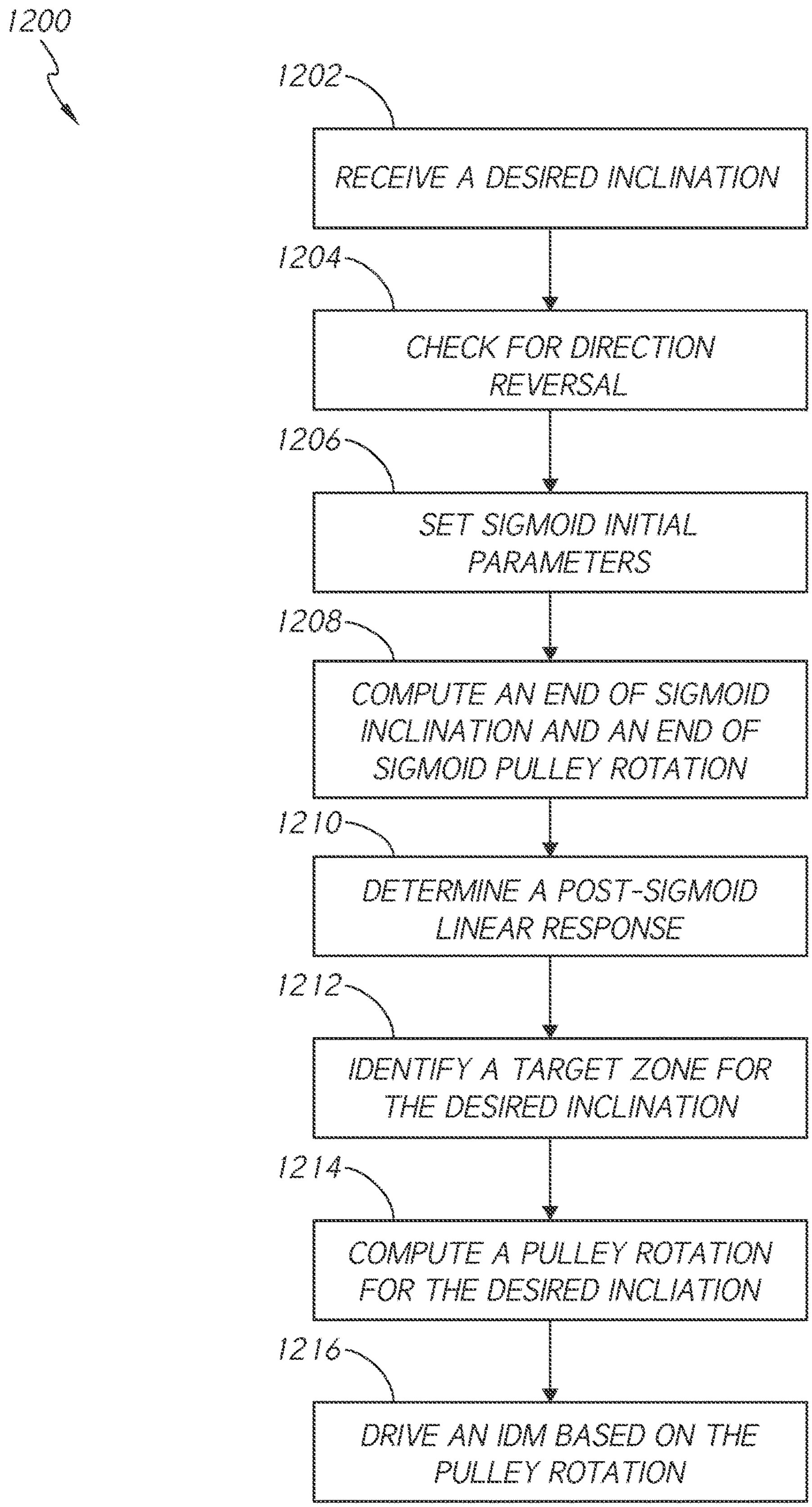
FIG. 12 is a flow diagram for a process of controlling instrument articulation based on a kinematic model in accordance with one or more embodiments.

FIG. 12 is a flow diagram 1200 for a process of controlling instrument articulation based on a kinematic model in accordance with one or more embodiments. The process can be used to compute a predicted pulley rotation (or a required tension) to effectuate a desired articulation of an endoscope. The process may be implemented in connection with articulation of the endoscope through robotic control of pull wire tensioning pulleys/mechanisms associated with the endoscope (e.g., incorporated with a handle of the endoscope). The process may be implemented at least in part by control circuitry of any of the system components disclosed herein, such as a robotic cart/system and/or control tower/system. For the purpose of facilitating descriptions, the endoscope is assumed to initially be in a neutral (e.g., straightened) position with pulley rotation reset. However, the process may be applied to the endoscope at any position and any pulley rotation as long as its position is accurately identified on its kinematic model.

At block 1202, a desired articulation can be received. The desired articulation can be a commanded articulation received from an operator. The desired articulation may be expressed as an angle within an articulable range defined about some reference in various manners. For example, some feasible articulable range definitions can include [−90°, 90°], [0°, 180°], [−π/2, π/2], [0, π], or the like.

At block 1204, whether the desired articulation causes a direction reversal can be checked. In some embodiments, the check for a direction reversal can involve comparing a currently commanded pulley rotation direction for the desired articulation with a previously commanded pulley rotation direction. For example, assume the last pulley rotation involved a clockwise rotation. If the commanded pulley rotation direction is also clockwise, then the commanded pulley rotation does not cause a direction reversal. Otherwise, if the commanded pulley rotation is counterclockwise, then the commanded pulley rotation causes a direction reversal.

In some embodiments, the check for a direction reversal can involve comparing the desired articulation with previous actual articulations. For example, a previous direction of articulation change can be determined by sampling the previous actual articulations. If the desired articulation continues in the same direction as the previous direction, then the desired articulation does not cause a direction reversal. On the other hand, if the desired articulation does not continue in the same direction as the previous direction, then the desired articulation causes a direction reversal.

When a direction reversal is not detected, blocks 1206, 1208, 1210, 1212 may be optional and the process may jump to block 1214. When a direction reversal is detected, the process continues with block 1206.

At block 1206, parameters and variables for a sigmoid can be set. As described, the parameters can include calibrated parameters, such as $k_{flex}$, $j_{dz0}$, Q, B, and nu, that fit a kinematic model to the endoscope. The variables can be observed variables associated with a current endoscope state, such as $k_\phi$, $k_j$, $\phi_{offset}$, $\phi_{@Reversal}$, $j_{@Reversal}$, and $j_c$. Specifically, a reversal articulation ($\phi_{@Reversal}$) and a reversal pulley rotation ($j_{@Reversal}$) observed can indicate at which articulation and pulley rotation the direction reversal occurred. Further, the reversal articulation and the reversal pulley rotation can help identify a region of the kinematic model in which robotic control of the endoscope is positioned.

At block 1208, an end of sigmoid articulation ($\phi_{@EoS}$) and an end of sigmoid pulley rotation ($j_{@EoS}$) can be computed. When the commanded articulation for the direction reversal occurs at a point corresponding to articulation response region of the first linear region 1101, the third linear region 1104, the third nonlinear region 1107, or the fourth nonlinear region 1108, the end of sigmoid articulation and the end of sigmoid pulley rotation can be calculated based on Eq. 4 and Eq. 5, respectively. However, if the direction reversal is towards one of the linear responses of the articulation in the first linear region 1101 or the third linear region 1104 (i.e., when the commanded articulation for the direction reversal occurs at a point corresponding to articulation response regions of the first nonlinear region 1102, the second linear region 1103, the second nonlinear region 1105, or the fourth linear region 1106), the end of sigmoid articulation can be calculated based on Eq. 4 while computation of the end of sigmoid pulley rotation can be simplified by using the inverted form of Eq. 1 at the end of sigmoid articulation (instead of using Eq. 5) since the end of sigmoid pulley rotation lies on one of the linear responses. The computed variables of the end of sigmoid articulation and the end of sigmoid pulley rotation together with the parameters and the observed variables from the block 1206 can define the sigmoid for the direction reversal.

At block 1210, a post-sigmoid linear response can be determined. When the commanded articulation for the direction reversal occurs at a point corresponding to articulation response region of the first linear region 1101, the third linear region 1104, the third nonlinear region 1107, or the fourth nonlinear region 1108, the post-sigmoid linear response can be determined by connecting the computed end of sigmoid articulation and the end of sigmoid pulley rotation to an end (e.g., $-j_{dz}$ or $+j_{dz}$) of the center dead zone 1109. However, if the direction reversal is towards one of the linear responses of the articulation in the first linear region 1101 or the third linear region 1104 (i.e., when the commanded articulation for the direction reversal occurs at a point corresponding to articulation response regions of the first nonlinear region 1102, the second linear region 1103, the second nonlinear region 1105, or the fourth linear region 1106), the determination of the post-sigmoid linear response can be simplified by considering the post-sigmoid linear response as equivalent to the linear responses in the first linear region 1101 or the third linear region 1104 (as the post-sigmoid linear response aligns with the articulation in the linear regions).

At block 1212, a target region for the desired articulation can be identified. Specifically, it is determined whether the desired articulation lies on the post-sigmoid linear response (e.g., the first linear region 1101, the second linear region 1103, the third linear region 1104, or the fourth linear region 1106) or lies on the sigmoid of the direction reversal, somewhere between the reversal articulation ($\phi_{@Reversal}$) and the end of sigmoid articulation ($\phi_{@EoS}$), on a nonlinear region (e.g., the first nonlinear region 1102, the second nonlinear region 1105, the third nonlinear region 1107, or the fourth nonlinear region 1108).

At block 1214, a predicted pulley rotation for the desired articulation is computed. The predicted pulley rotation is computed based on the identified target region. If the target region is the post-sigmoid linear response determined at the block 1210, then the predicted pulley rotation is computed using the equation Eq. 1 when the post-sigmoid linear response coincides with the articulation (e.g., in the first linear region 1101 or the third linear region 1104) or the equation Eq. 2 when the post-sigmoid linear response coincides with the de-articulation (e.g., in the second linear region 1103 or the fourth linear region 1106). Alternatively, if the target zone is on the sigmoid of the direction reversal at the block 1212, then the predicted pulley rotation is computed using the equation Eq. 3.

At block 1216, an IDM is driven based on the predicted pulley rotation computed at the block 1214 to effectuate the desired articulation. The provision of the predicted pulley rotation should result in the desired articulation.

Relaxation Tension Monitoring and Homing Algorithm

As described, robotic control of an endoscope can involve pulling one or more pull wires attached to a dual-wire pulley to articulate a tip of an endoscope. As illustrated with regard to FIG. 12, to achieve a desired articulation, a kinematic model can be used to compute a required pulley rotation. Then, the required pulley rotation can be applied by driving an IDM to a pulley rotation corresponding to the desired articulation. The required pulley rotation is computed based on a reference position, which is also referred as a home position or home. For simplicity, a robotic system may assign a pulley rotation that causes zero inclination as the home position. Homing can refer to a process of finding the home position (e.g., determining a homing offset that causes zero inclination) and, in some instances, may further include adjusting indexing of pulley rotations such that the home position is positioned at zero pulley rotation (e.g., indexing the homing offset to be at zero pulley rotation).

Generally, the above description of a kinematic model assumes that an endoscope is initialized with zero inclination (e.g., a neutral articulation, a reference articulation, a relaxed articulation, etc.) at zero pulley rotation. For example, the kinematic model 1100 illustrated in FIG. 11A is centered at zero pulley rotation, which has neither clockwise nor counterclockwise offset, and at zero inclination, which is pre-articulated neither leftward nor rightward. However, the assumption may not always be correct.

The assumption of initialization with zero inclination at zero pulley rotation may be violated when a pre-articulated endoscope (e.g., an endoscope with non-zero articulation) is docked. The violation of the assumption can result in a misalignment between predicted endoscope behavior, based on a kinematic model, and physical endoscope behavior. For example, a robotic system may rely on the kinematic model to predict an articulation given a pulley rotation. When the endoscope is pre-articulated, the pulley rotation can cause further articulation in addition to the pre-articulation, causing unpredicted physical endoscope behavior.

In part, the misalignment may be a result of information asymmetry between a robotic system sending an articulation command and an endoscope receiving the articulation command and articulating its elongated shaft. Before docking, the robotic system may be aware of its states, such as a current pulley rotation of a drive output, but may not be aware of states of the detached endoscope, such as a pre-articulation and/or actual tension on pull wires. That is, before docking, the robotic system may initialize its pulley rotation to zero or some other reference value but that initialization of the pulley rotation may not center the decoupled pre-articulated endoscope.

Figure 13B:
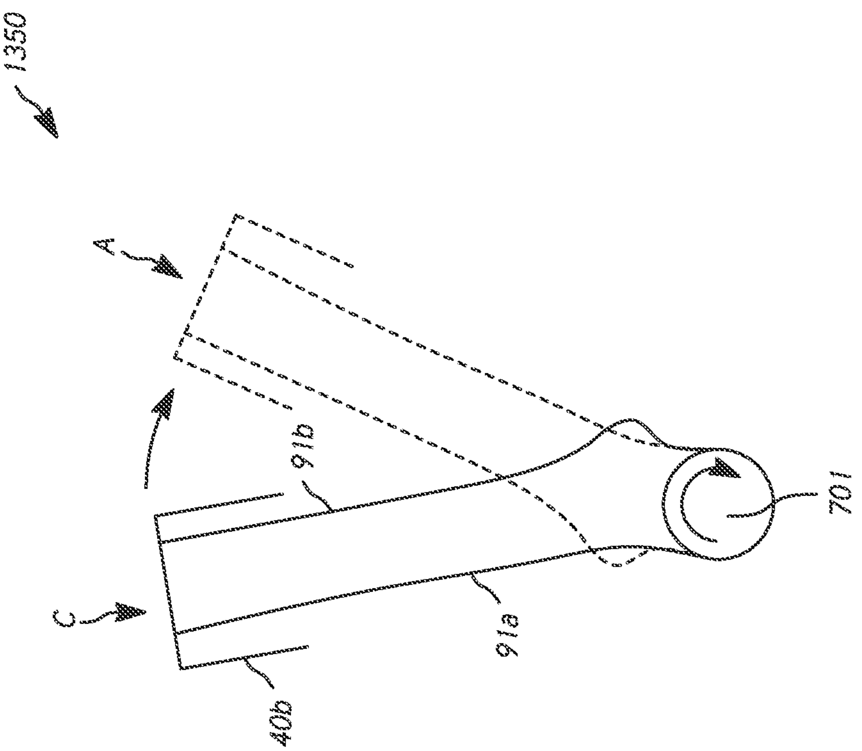
FIGS. 13A-13B illustrate an example articulation scenario of a pre-articulated endoscope and an example relaxation scenario of an articulated endoscope in accordance with one or more embodiments.
Figure 13A:
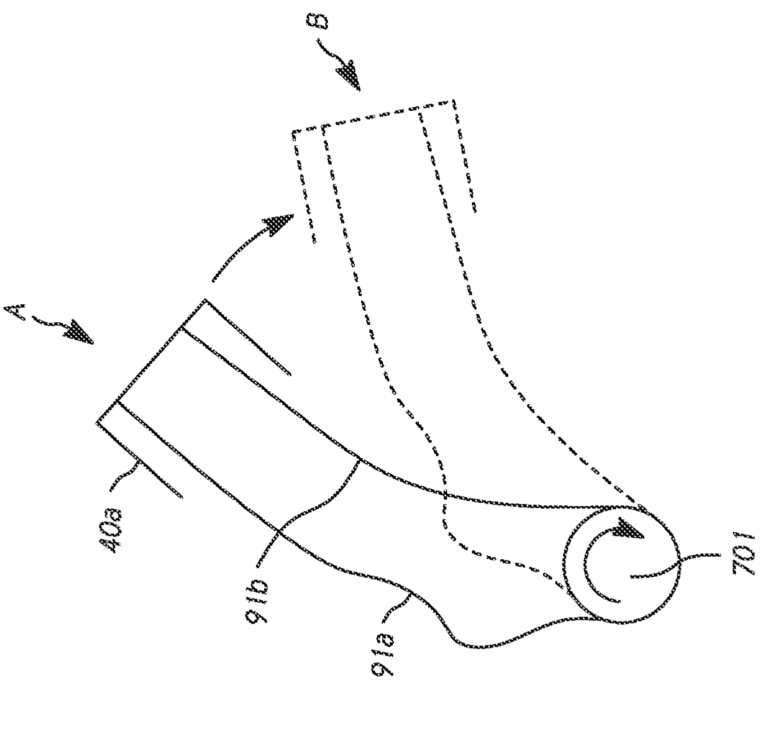

When the assumption that a straightened endoscope is docked is invalid, it can impact multiple facets of robotic endoscope control, including articulation and relaxation. Here, relaxation may indicate a process of decreasing magnitude of inclination for an endoscope to make the endoscope straight (e.g., zero inclination). FIGS. 13A-13B illustrate example scenarios in which the assumption can result in undesirable consequences.

FIG. 13A illustrates an example articulation scenario 1300 of a pre-articulated endoscope in accordance with one or more embodiments. The articulation scenario 1300 shows an endoscope 40*a* having a tip attached to ends of pull wires 91 including a first pull wire 91*a* and a second pull wire 91*b*. The opposing ends of the pull wires 91 are attached to a dual-wire pulley 701. As shown, when the endoscope 40*a* is docked to an end effector, the first pull wire 91*a* may be loose, the second pull wire 91*b* may be taut, and the endoscope 40*a* may be pre-articulated rightward in a pre-articulated state A.

Unless further articulation takes the pre-articulated state A into account, further articulation may result in undesired articulation that may cause harm to the endoscope and/or patient anatomy. In the articulation scenario 1300, assume a rightward articulation is desired. A robotic system, oblivious to the rightward pre-articulation, may command a clockwise pulley rotation to cause the further rightward articulation. When the clockwise pulley rotation is applied, the endoscope 40*a* is to be articulated from its pre-articulated state A to an articulated state B. Application of the clockwise pulley rotation may increase tension on the already taut second pull wire 91*b* beyond its acceptable tolerance and could cause irreparable harm to the second pull wire 91*b* and endoscope functionality. Further, as the articulated state B may result in an unintended articulation that goes further rightward than a desired articulation that would result from a zero inclination-initialized endoscope, the articulated state B may potentially cause harm to the patient anatomy.

FIG. 13B illustrates an example relaxation scenario 1350 of an articulated endoscope in accordance with one or more embodiments. Similar with the endoscope 40*a* of the articulation scenario 1300, an endoscope 40*b* can include a first pull wire 91*a*, a second pull wire 91*b*, and a dual-wire pulley 701. As shown, the first pull wire 91*a* may be taut, the second pull wire 91*b* may be loose, and the endoscope 40*b* may be articulated leftward in an articulated state C from the pre-articulated state A.

Unless relaxation takes the pull wire 91 conditions of the articulated state C into account, relaxation may result in undesired articulation that may cause harm to the patient anatomy. In the relaxation scenario 1350, it is assumed the endoscope 40*b* was docked with the pre-articulated state A at its initialization. When relaxation is commanded, a robotic system assuming zero inclination at initialization may apply a pulley rotation at initialization to return the endoscope 40*b* to zero inclination. However, that pulley rotation instead returns the endoscope 40*b* to the pre-articulated state A, which is not relaxed at zero inclination. The unintended return to the pre-articulated state A during relaxation may cause harm to the patient anatomy.

Figure 14:
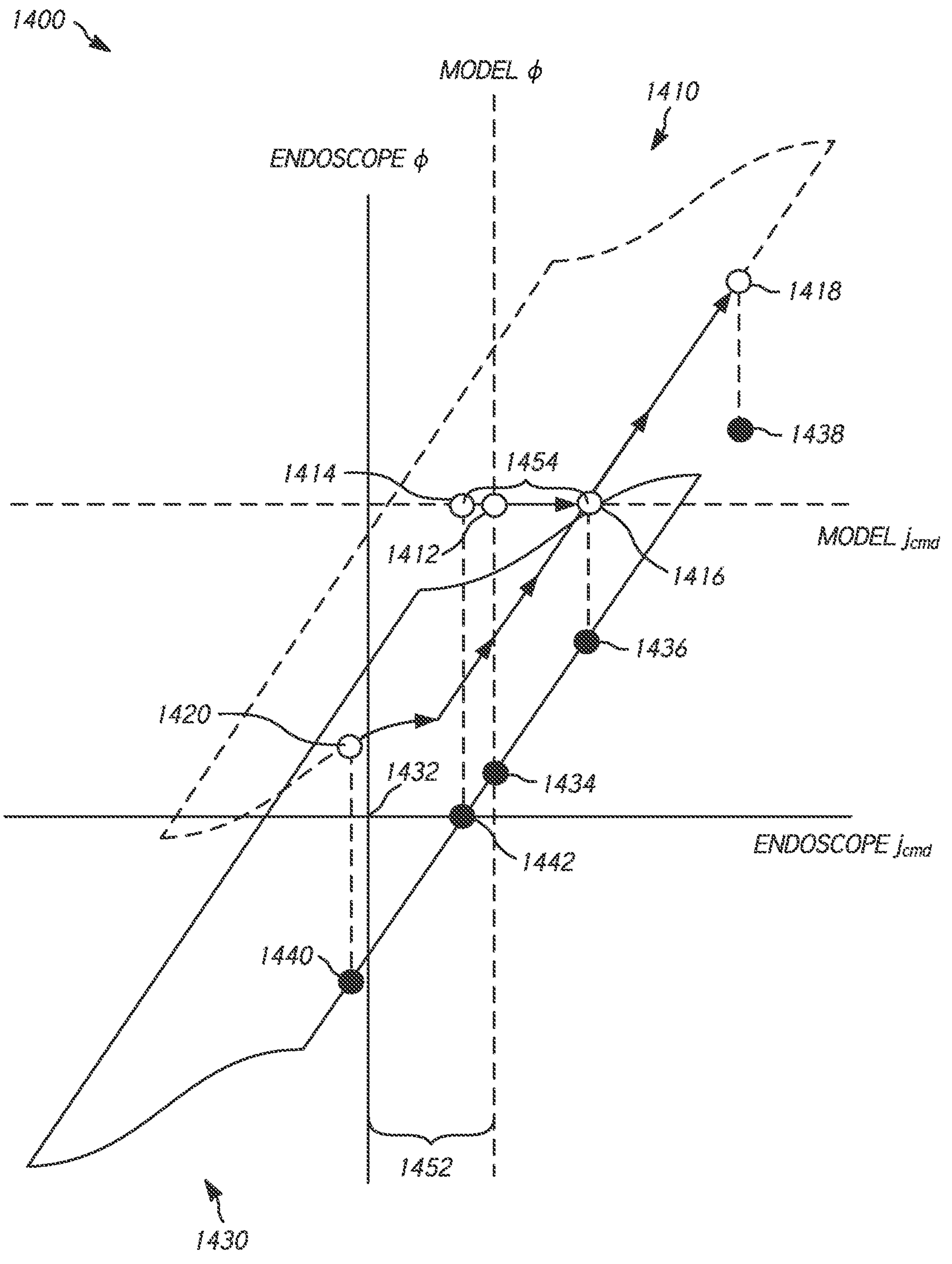
FIG. 14 illustrates an example articulation response plot showing a relationship between a modelled articulation response and physical endoscope behavior when a pre-articulated endoscope is docked in accordance with one or more embodiments.

FIG. 14 illustrates an example articulation response plot 1400 showing a relationship between a modelled response 1410 and physical endoscope behavior 1430 when a pre-articulated endoscope is docked in accordance with one or more embodiments. The articulation response plot 1400 plots the modelled response 1410 and the physical endoscope behavior 1430 on an XY-plane having an X-axis that represents pulley rotation (e.g., a rotational amount) and a Y-axis that represents deflection/articulation (e.g., an inclination).

The modelled response 1410 represents an expected endoscope articulation response based on a kinematic model of an endoscope. The modelled response 1410 is plotted from a perspective of a robotic system controlling the endoscope. The robotic system can center the modelled response 1410 in the XY-plane at zero inclination and zero pulley rotation, at the model origin 1412. That is, the modelled response 1410 uses the model origin 1412 as its reference point (e.g., home position).

The physical endoscope behavior 1430 represents an actual endoscope articulation response from a perspective of a pre-articulated endoscope. The physical endoscope behavior 1430 has an endoscope origin 1432 that is shifted/translated compared to the model origin 1412 of the modelled response 1410. As described previously, the misalignment between the modelled response 1410 and the physical endoscope behavior 1430 can be caused by a pre-articulation at docking. For example, a pre-articulation point 1434 on the physical endoscope behavior 1430 indicates that the endoscope is pre-articulated with a slight rightward inclination (e.g., the pre-articulation point 1434 is above the endoscope origin 1432). However, the robotic system controlling the endoscope based on the modelled response 1410 is oblivious to the slight rightward pre-articulation and assumes that the endoscope is at zero inclination. In some instances, the misalignment can be caused by component variations, tolerances, or degradations.

The misalignment can cause some undesirable consequences previously described in relation to FIGS. 13A and 13B during articulation and relaxation. For example, assume the robotic system desires to articulate a straightened endoscope rightward. Based on the modelled response 1410, the robotic system will issue a clockwise change in pulley rotation from the model origin 1412, through a first model point 1416, to a second model point 1418. The robotic system expects the change in pulley rotation to cause the endoscope to articulate from a straightened articulation at the model origin 1412 and the first model point 1416 to a rightward articulation at the second model point 1418. However, as shown in the physical endoscope behavior 1430, the commanded change causes the endoscope to articulate, from slightly rightward articulation at the pre-articulation point 1434, to a moderate rightward articulation at a first endoscope point 1436 to an unattainable rightward articulation at a second endoscope point 1438, which is outside the confines of the physical endoscope behavior 1430.

FIG. 13A provides visual aid for articulation of the endoscope receiving the commanded change. At the pre-articulation point 1434, the endoscope can be in the pre-articulated state A of the example articulation scenario 1300. At the first endoscope point 1436, the endoscope articulates toward the articulated state B. However, the endoscope cannot articulate much further beyond the articulated state B even when provided the pulley rotation at the second endoscope point 1438. In fact, the pulley rotation at the second endoscope point 1438 could apply too much tension on the pull wires 91 of the endoscope and may be potentially damaging to the endoscope. Additionally, from the model origin 1412 to the first model point 1416, the robotic system does not expect any articulation when providing a change in pulley rotation since the modelled response 1410 shows no change for its Y-axis. However, as the corresponding physical endoscope behavior 1430 shows, the change in pulley rotation causes significant articulation from the pre-articulation point 1434 to the first endoscope point 1436. The unintended articulation may cause harm to the patient anatomy.

As another example, assume the robotic system desires to relax a leftward articulated endoscope. Based on the modelled response 1410, the robotic system will issue a clockwise change in pulley rotation from a third model point 1420 to the first model point 1416. The robotic system expects the change in pulley rotation to cause the endoscope to change from the leftward articulation at the third model point 1420 to a straightened articulation at the first model point 1416. However, as shown in the physical endoscope behavior 1430, the commanded change causes the endoscope to articulate, from a leftward articulation at a third endoscope point 1440, through the straightened articulation at a fourth endoscope point 1442 and pre-articulation at the pre-articulation point 1434, to a rightward articulation at the first endoscope point 1436.

FIG. 13B provides visual aid for articulation of the endoscope receiving the commanded change. At the third endoscope point 1440, the endoscope can be in the articulated state C of the example relaxation scenario 1350 with the leftward articulation. At the pre-articulation point 1434 corresponding to the model origin 1412 for zero inclination, the endoscope has already articulated pas zero inclination and toward the pre-articulated state A. At the first endoscope point 1436, the endoscope articulates further rightward. That is, while the robotics system drives the commanded change to straighten the endoscope, the commanded change over-articulates the endoscope past zero inclination. The unintended articulation may cause harm to the patient anatomy.

The nonlinearities and the center dead zone can amplify/attenuate a discrepancy between a predicted articulation and an actual articulation. For example, during traversal between the third model point 1420 and the first model point 1416, the modelled response 1410 shows a smaller change in articulation compared to the physical endoscope behavior 1430 due to the nonlinearity. As another example, during traversal between the model origin 1412 to the first model point 1416, the modelled response 1410 shows no change in articulation but the physical endoscope behavior 1430 shows a significant articulation. Accordingly, the nonlinearities and the center dead zone, can further complicate delivery of a desired articulation.

The issues may be avoided/mitigated if the modelled response 1410 and the physical endoscope behavior 1430 can be aligned (e.g., homed) such that they share a common reference. That is, if the robotic system can determine a pulley rotation offset 1452, the robotic system can use the pulley rotation offset 1452 to shift/translate the modelled response 1410 onto the physical endoscope behavior 1430, or vice versa.

A homing algorithm can determine a homing offset (e.g., the pulley rotation offset 1452) and provide the alignment. The homing algorithm can be executed at any time, manually or automatically. In one embodiment, the homing algorithm can be executed when an endoscope is docked to address pre-articulation that was present before docking and to avoid potential harm to the patient anatomy. The homing algorithm can determine whether one or more homing condition(s) are satisfied and, when the condition(s) are satisfied, align the modelled response 1410 and the physical endoscope behavior 1430.

A relaxation algorithm can provide reliable relaxation (e.g., return to zero inclination) of the endoscope. Ability to reliably relax an endoscope may further mitigate potential articulation issues. For example, if the endoscope can reliably return to a relaxed position, then an operator noticing some undesired articulation can correct the undesired articulation by articulating the endoscope to a relaxed position. That is, the robotic system can minimize the discrepancy between an expected endoscope behavior and an actual endoscope behavior by resetting the endoscope to a relaxed position, e.g., zero inclination. The endoscope can then be articulated from the known articulation (e.g., zero inclination) before advancement into or retraction from the patient anatomy. Relaxation can be commanded at any time as desired.

In some embodiments, the relaxation algorithm can monitor tension on one or more pull wires during performance of relaxation. Generally, decreasing net magnitude of tension and articulation are expected during the relaxation. Thus, the robotic system can complete the relaxation by continuing to drive pulley rotation toward lower tension until zero articulation or some minimal tension (e.g., falling below a minimum tension threshold) is achieved.

In some embodiments, it may be advantageous to execute the homing algorithm in tandem or as a part of relaxation (e.g., execution of the relaxation algorithm). As described, the relaxation attempts to return an endoscope to a known inclination (e.g., zero inclination), which may be the home position. Accordingly, determining a pulley rotation associated with zero inclination may involve determining the pulley rotation offset 1452. A relaxation tension monitoring and homing algorithm that performs both relaxation and homing is described in relation to FIG. 15.

Figure 15:
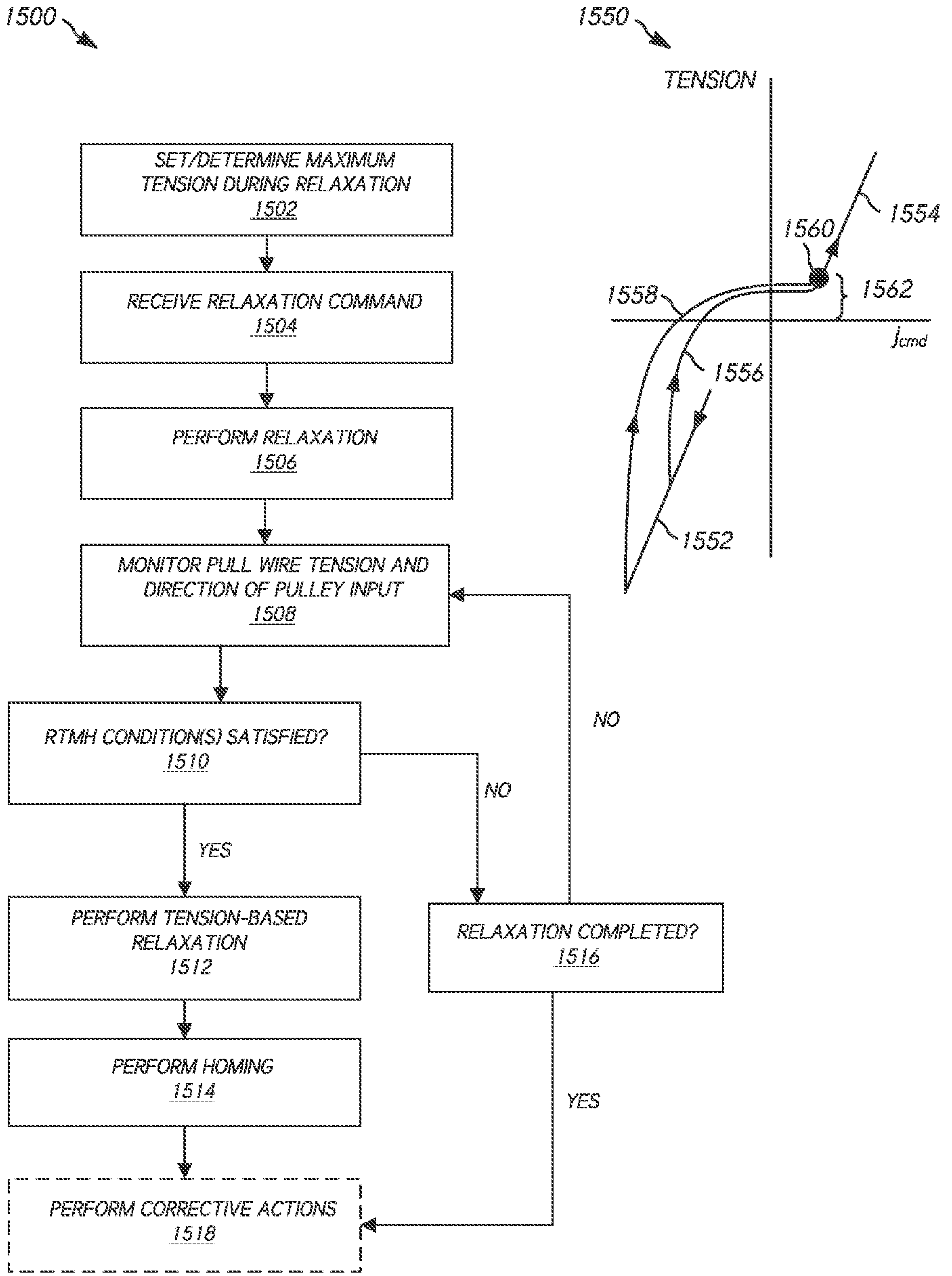
FIG. 15 is a flow diagram for a process of relaxing and homing an endoscope based at least in part on pull wire tension monitoring in accordance with one or more embodiments.

FIG. 15 is a flow diagram for a process 1500 of relaxing and homing an endoscope based at least in part on pull wire tension monitoring in accordance with one or more embodiments. The process 1500 can determine whether there exists a misalignment between a modelled endoscope response and an actual endoscope response during performance of a commanded relaxation. When the process 1500 identifies such misalignment, then the process 1500 can perform tension-based relaxation and homing to correct the misalignment. The process 1500 may be implemented in connection with articulation of an endoscope shaft through robotic control of pull wire tensioning pulleys/mechanisms associated with the endoscope (e.g., incorporated with a handle of the endoscope). The process 1500 may be implemented at least in part by control circuitry of any of the system components disclosed herein, such as a robotic cart/system and/or control tower/system. For the purpose of simplifying below descriptions, the robotic system is selected.

At block 1502, the process 1500 involves setting, receiving, accessing, or otherwise determining one or more tension threshold levels/values associated with respective relaxation and/or homing algorithms. Such threshold parameters may comprise a maximum tension during relaxation, which may be set during tuning/calibration of the endoscope based on safety requirements to avoid any damage to the endoscope and the patient anatomy. Such parameter(s) may be maintained as global values relevant to one or more endoscope devices, or may be determined/set by the robotic system as process- and/or instrument-specific values. In some implementations, the process 1500 may involve identifying a specific instrument/endoscope used in the process 1500, such as by a unique identifier or other identification, which may be manually identified and/or input, or may be automatically read/interrogated when the endoscope is docked to the robotic system (e.g., using radio-frequency identification (RFID) or other technology). The system may maintain/store specifications/parameters associated with various instrument identifiers and the process 1500 may involve accessing such parameters for the particular instrument/endoscope utilized.

At block 1504, the process 1500 involves receiving a relaxation command. There may be different types of "relaxation." For example, a first type of relaxation may be a straightforward relaxation involving rotation of one or more pulleys to relaxation pulley rotations that are presumed to articulate an endoscope to a reference articulation (e.g., de-articulate the endoscope to zero inclination). A relaxation pulley rotation can be computed based at least in part on a kinematic model (e.g., the modelled response 1410 of FIG. 14). If the first type of relaxation is based on the kinematic model, monitoring tension on one or more pull wires may be optional. When there is a misalignment (e.g., when the endoscope is docked pre-articulated), the first type of relaxation may not be able return the endoscope to the reference articulation. In the present application, the first type of relaxation will be referred as "relaxation."

A second type of relaxation may be a tension-based relaxation which relies on monitored tension to relax the endoscope. The second type of relaxation can rotate pulleys to decrease tension on pull wires until the monitored tension is below a threshold value, zero, or substantially zero, thereby ensuring that the endoscope is relaxed at a desired inclination such as a near zero inclination. In other words, the second type of relaxation is a relaxation based on an actual endoscope response (e.g., the physical endoscope behavior 1430 of FIG. 14). The second type of relaxation need not refer to the preset or supplied pulley rotation in relaxing the endoscope but, rather, can actively determine the relaxation pulley rotation. In the present application, the second type of relaxation will be referred as "tension-based relaxation" to distinguish from the first type of relaxation.

The relaxation command may be automatically received, such as upon docking of the endoscope, or manually instructed. Regarding the manual instruction, the robotic system utilized to implement the process 1500, which may comprise any of the features of any robotic system disclosed herein, may include a means for receiving the relaxation command from a user. Such user input may be received via a controller or other user input device, wherein manual (or other) engagement with one or more input mechanisms (e.g., button, joystick, slider, lever, knob, or the like) can generate the relaxation command received by the robotic system (e.g., robotic control tower/cart).

At block 1506, the process 1500 involves performing the commanded relaxation. When the user commands the scope to relax, the robotic system may attempt to de-articulate the endoscope with the relaxation pulley rotation which presumably should return the endoscope to zero inclination. In some implementations, the robotic system may select a direction of pulley rotation (e.g., clockwise, counterclockwise, or toward a particular direction in a plane) that would decrease a difference between a current pulley rotation and the relaxation pulley rotation. By rotating the pulley toward the direction, pulley displacement between the current pulley rotation and the relaxation pulley rotation can be reduced toward zero.

At block 1508, the process 1500 involves monitoring and/or determining tension/force (f) associated with one or more pull wires of the surgical instrument coupled to the robotic system (e.g., endoscope coupled to end effector of robotic cart) and/or a direction of pulley rotation. In some implementations, the tension can be net tension on the one or more pull wires. In other implementations, the tension can be of an individual pull wire. The robotic system may be configured to control articulation of the coupled instrument in a direction, dimension, and/or plane associated with the articulation input. The monitored tension/force may be associated with a pull wire coupled to a pulley or other actuator configured to cause tensioning/untensioning of the pull wire, and/or the tension/force may be associated with the pulley/actuator itself. That is, the monitoring of the tension in connection with block 1508 may involve directly monitoring tension on the pull wire(s) (e.g., through strain-gauge coupling/measurement) and/or monitoring tension/torque on a tensioning actuator (e.g., pulley), or component/actuator mechanically coupled thereto, such as output drive(s)/gear (s) of a robotic end effector coupled to the instrument base. In some embodiments, one or more torque sensors may be used to generate signals indicative of the pull wire tension, wherein such torque sensors may be associated with any component, device and/or system of the robotic system. For example, the torque sensors may be associated with a robotic end effector that is coupled to the instrument and is configured to drive articulation of the instrument. The torque sensor(s) may be utilized for monitoring torque on robotic output drive(s) (e.g., gears, splines) coupled to the tensioning pulley(s) of the instrument (e.g., associated with the instrument base/handle).

Tension monitoring in connection with block 1508 may be implemented with a lookback window configured to store the monitored tension and/or the direction of pulley rotation over time, such as over time samples. The lookback window may provide a mechanism with which samples of stored tension and direction of pulley input can be compared with one another to provide a measure of change in tension and, if any, change in direction of pulley rotation. The change in tension and/or direction of pulley rotation can provide, among other things, indications of whether one or more pull wire is undergoing an increase (e.g., pulled) or decrease (e.g., released) in tension during a continued pulley rotation in a particular direction.

At block 1510, the process 1500 involves determining whether relaxation tension monitoring and homing (RTMH) conditions are satisfied. The determination can be based on the change in monitored tension and direction of pulley rotation of block 1508. The conditions can include (i) whether the robotic system is rotating the pulleys toward a direction that should release the tension, (ii) the monitored tension is increasing in magnitude during the one or more most recent time sample(s), and (iii) the monitored tension during the most recent time sample is greater than the maximum tension during relaxation, which may have been set/determined at block 1502.

The conditions are described in reference to a tension response plot 1550, which depicts portions having similar shape with the tension response 1150 of FIG. 11B. The tension response plot 1550 shows two linear regions 1552, 1554 and two nonlinear regions 1556, 1558. As illustrated, the monitored tension should decrease in magnitude while the robotic system presumably de-articulates the endoscope toward the zero inclination during traversal on the nonlinear regions 1556, 1558 during performance of the commanded relaxation, which satisfies the first condition (i). Subsequently, tension starts increasing in magnitude after the traversal crosses the zero inclination and continues to increase, thereby satisfying the second condition (ii). Eventually, further traversal increases tension in magnitude beyond the maximum tension during relaxation 1562, thereby satisfying the third condition (iii). In the tension response plot 1550, the three conditions satisfied at a point 1560.

The satisfaction of the three conditions can trigger the RTMH algorithm. The satisfaction of the three conditions may occur as a result of a pre-articulated endoscope. As previously described in relation to FIG. 14, a pre-articulated endoscope can cause a misalignment between a kinematic model (e.g., the modelled response 1410 of FIG. 14) and an actual endoscope response (e.g., the physical endoscope behavior 1430 of FIG. 14). For example, upon receiving the relaxation command at block 1504, the robotic system computes or otherwise acquires the relaxation pulley rotation that it expects to return the endoscope to zero inclination. Applying the relaxation pulley rotation should normally only involve decrease in tension during performance of the command. When the computed pulley rotation instead causes increase in tension magnitude, the endoscope likely has an unaccounted for articulation (e.g., pre-articulation or undesired digression from commanded relaxation).

Referring to the articulation response plot 1400, the relaxation (e.g., the first type relaxation) commanded by the robotic system can be visually represented as a traversal from the third model point 1420 to the first model point 1416 where the robotic system applies a relaxation pulley rotation that is expected to bring an endoscope to zero inclination. However, when the robotic system drives the relaxation pulley rotation, the relaxation pulley rotation actually causes the physical endoscope behavior 1430 to articulate from a leftward articulation at the third endoscope point 1440 through zero inclination at the fourth endoscope point 1442 to a rightward articulation at the first endoscope point 1436. The endoscope articulation can satisfy the three conditions at or near the fourth endoscope point 1442, before the full traversal involving the relaxation pulley rotation. Thus, the satisfaction of the three conditions before the full traversal can indicate a failure of the commanded relaxation.

The failure of the commanded relaxation can be caused by the misalignment. To correct the misalignment, the process 1500 can proceed to block 1510 to perform RTMH algorithm, which can involve tension-based relaxation (e.g., the second type relaxation) and homing of the endoscope.

At block 1512, the process 1500 involves performing tension-based relaxation. The tension-based relaxation uses the monitored tension to relax the endoscope to the zero inclination. That is, the monitored tension is relied on to rotate the pulleys in the direction of decreasing tension. The robotic system may continue driving pulley rotation toward lower tension until zero or some minimal tension is achieved. If the robotic system can achieve the zero or minimal tension, then the endoscope can be assumed to be relaxed into the zero inclination. In some implementations, whether the minimal tension is achieved can be determined based on a comparison of the monitored tension to a minimum tension threshold. After the tension-based relaxation completes, the process 1500 can proceed to homing part of the RMTH algorithm.

At block 1514, the process 1500 involves performing homing. After completion of block 1512, the endoscope should be de-articulated with the zero inclination. In this block 1514, the robotic system can determine the current pulley rotation that resulted in the zero inclination and set the pulley rotation as the relaxation pulley rotation that presumably cause the endoscope to relax. That is, the homing can enable the first type relaxation that uses the relaxation pulley rotation to relax the endoscope in the future without reliance on tension monitoring.

Homing can resolve the misalignment between a modelled response and an actual response. Described in relation to the example articulation response plot 1400 of FIG. 14, the homing in connection with block 1514 may be implemented with an adjustment/shift/translation that aligns the modelled response 1410 with the physical endoscope behavior 1430. The homing can involve various steps.

As a step, block 1514 can involve setting/resetting current articulation to zero inclination. Here, the robotic system can reset its articulation from a current articulation to zero inclination. The reset can prepare the robotic system for application of a homing offset 1454.

As another step, block 1514 can involve computing the homing offset 1454. The homing offset 1454 can be computed based on the current pulley rotation that provided the zero inclination and the center dead zone. For example, a pulley rotation at the fourth model point 1414 in the modelled response 1410 may correspond to the current pulley rotation that actually provided the zero inclination, as indicated by the fourth endoscope point 1442 of the physical endoscope behavior 1430.

The homing offset 1454 can be determined based on a relationship between a pulley rotation that is, based on a kinematic model, expected to provide a certain articulation and a pulley rotation that actually provides the certain articulation. For example, the modelled response 1410 expects to have zero inclination with a pulley rotation at the first model point 1416. However, it was the pulley rotation corresponding to the fourth model point 1414 (e.g., the fourth endoscope point 1442) that actually provided the zero inclination. The homing offset 1454 may be calculated as a difference between (e.g., a subtraction between) an expected pulley rotation and an actual pulley rotation, such as between the pulley rotations at the fourth model point 1414 and the first model point 1416. The expected pulley rotation is at the first model point 1416 observed at an edge (e.g., the right edge) of the center dead zone. The expected pulley rotation may have a value of a half of the central dead zone range. In the articulation response plot 1400, when the expected pulley rotation is subtracted by the actual pulley rotation at the fourth model point 1414, the subtraction adds a magnitude of the actual pulley rotation to the expected pulley rotation since the actual pulley rotation is a negative value. The result is the homing offset 1454 which may be the same or substantially the same as the pulley rotation offset 1452.

In some embodiments, the homing offset 1454 can be applied to adjust pulley rotations. That is, all subsequent pulley rotations as controlled by the robotic system can be adjusted by the homing offset 1454. For example, after homing, the pulley rotation at the first model point 1416 may be subtracted by the homing offset 1454 and the robotic system may command articulation of the endoscope with the result. In reverse, when determining a pulley rotation that would result in a certain articulation, the robotic system can determine the pulley rotation based on the modelled response 1410 (e.g., a kinematic model for the endoscope) and adjust the pulley rotation by the homing offset 1454. For example, if an articulation at the third model point 1420 is desired, the robotic system can compute a pulley rotation for the third model point 1420 based on the modelled response 1410. Then, the robotic system can adjust the pulley rotation by applying the homing offset 1454 and control the endoscope with the resulting pulley rotation to articulate the endoscope to the desired articulation.

In some embodiments, the homing offset 1454 can be applied to permanently shift/translate the modelled response 1410 closer to the physical endoscope behavior 1430. The shift/translation can involve resetting an old X-axis, which was used to count/index pulley rotations, based on the homing offset 1454 to provide a new X-axis for subsequent counting/indexing of pulley rotations. The new X-axis becomes a new reference frame with which the robotic system counts/indexes pulley rotations. After the reset, the robotic system can count/index zero pulley rotation on the new X-axis where the old X-axis had a negative value of the homing offset 1454. Similarly, the robotic system can count/index the homing offset 1454 on the new X-axis where the old X-axis had zero pulley rotation. As a visual example, in the articulation response plot 1400, the resetting can leftward shift the modelled response 1410 by the homing offset 1454 so that a pulley rotation provided by the robotic system based on a shifted modelled response (not shown) aligns with the physical endoscope behavior 1430.

As yet another step, the homing can involve resetting a current inclination zone to post transition relaxation zone. Subsequent pulley rotations and expected articulations are affected by the application of the homing offset 1454. Accordingly, articulations previously expected on linear regions may now be on nonlinear regions, or vice versa. Similarly, articulations previously expected to de-articulate may now articulate, or vice versa. Thus, current inclination zone may need to be reset with a correct inclination zone (e.g., the post transition relaxation zone) after the application of the homing offset 1454 so that expected articulation in a zone matches with actual articulation in the zone. The reset of the current inclination zone can help performing relaxation that follows at block 1512.

Referring back to block 1510, if the conditions are not satisfied, the process 1500 can proceed to block 1516. At block 1516, the process 1500 involves determining whether the commanded relaxation of block 1506 has been completed. That is, the robotic system determines whether pulleys are fully rotated to the relaxation pulley rotation that presumably provides the zero inclination. If the pulleys are fully rotated or some other conditions indicate completion early termination of the relaxation, the process can proceed to block 1518. Otherwise, the process 1500 can proceed to block 1508 to continue monitoring tension.

At block 1518, the process 1500 involves performing any optional corrective actions. Block 1514 may be optional for instances where relaxation was paused, for example due to detection of a potential harm to the endoscope, the robotic system, or a patient, or where relaxation condition(s) were not achievable. The corrective actions can include various actions ranging from stopping the robotic control, reversing a direction of relaxation, or notifying the robotic system and/or the user of the failed relaxation.

It will be understood that any block and any step within a block may be performed/executed independently of other blocks and steps. Additionally, any block and any step within a block may be performed automatically or upon instruction. For example, the tension-based relaxation of block 1512 may be performed as part of the process 1500, when the robotic system is initializing, when the endoscope is docked, or when instructed by a user or the robotic system.

Passive Homing Algorithm

Robotic control of endoscopes involves computing a pulley rotation required to achieve a desired scope articulation. The pulley rotation is computed with respect to a home (e.g., a reference) position. As previously described, homing can refer to a process of finding the home position and, in some instances, may further include adjusting indexing of pulley rotations such that the home position is positioned at zero pulley rotation. That is, homing can configure the home position such that an endoscope is straightened at the home position which corresponds to zero pulley rotation.

Finding the home position can be frustrated by the existence of the center dead zone (e.g., the center dead zone 1109 in FIG. 11A), which is a characteristic exhibited by a dual-wire pulley. Within the center dead zone, pull wires attached to the dual-wire pulley may not apply enough tension to cause endoscope articulation. That is, if an endoscope is straightened, the endoscope remains straightened for a range of pulley rotations within the center dead zone. Since articulation responses for any pulley rotation within the center dead zone correspond to the straightened endoscope, any pulley rotation may be identified as the home position. Thus, finding a home position for a dual-wire pulley can additionally involve finding a pulley rotation that has a known relationship with the center of the center dead zone, such as at the center or at either end of the center dead zone.

Correct identification of the home position can be critical in endoscope control. If the home position is incorrectly identified, controlling the endoscope with the incorrect home position can cause significantly large pauses, rapid or jerky movement, and/or inconsistent articulation speed because a kinematic model for the endoscope will not accurately match with the actual endoscope articulation as designed. Furthermore, the incorrect home position may, in some instances, lead to unacceptably high forces on and potential damage to the patient anatomy.

A passive homing algorithm can enable a robotic system to identify a correct home position and, therefore, enable proper alignment between modeled and physical articulations. The passive homing algorithm is "passive" in a sense that (i) the algorithm does not execute separately but executes only when a robotic system actively commands articulation and/or (ii) the algorithm does not command any articulation but relies on articulation commanded independently of the algorithm. In other words, the passive homing algorithm may not initiate or command any articulation on its own but, rather, monitors for presence of a misalignment during other commanded articulations and, when appropriate, corrects the misalignment with homing. For example, the passive homing algorithm may be executing as a background process during actively commanded articulation to monitor tension on pull wires. The mere monitoring may not initiate or cause articulation but can inform the robotic system whether measured tension is aligned with expected tension of a model. When there is a misalignment, the passive homing algorithm may perform the homing. The passivity of the algorithm can be advantageous since there is no risk of un-commanded articulation caused by the algorithm due to its non-initiating and non-articulating nature. Accordingly, the algorithm cannot pose a patient safety risk. The algorithm is described in relation to FIG. 16.

Figure 16:
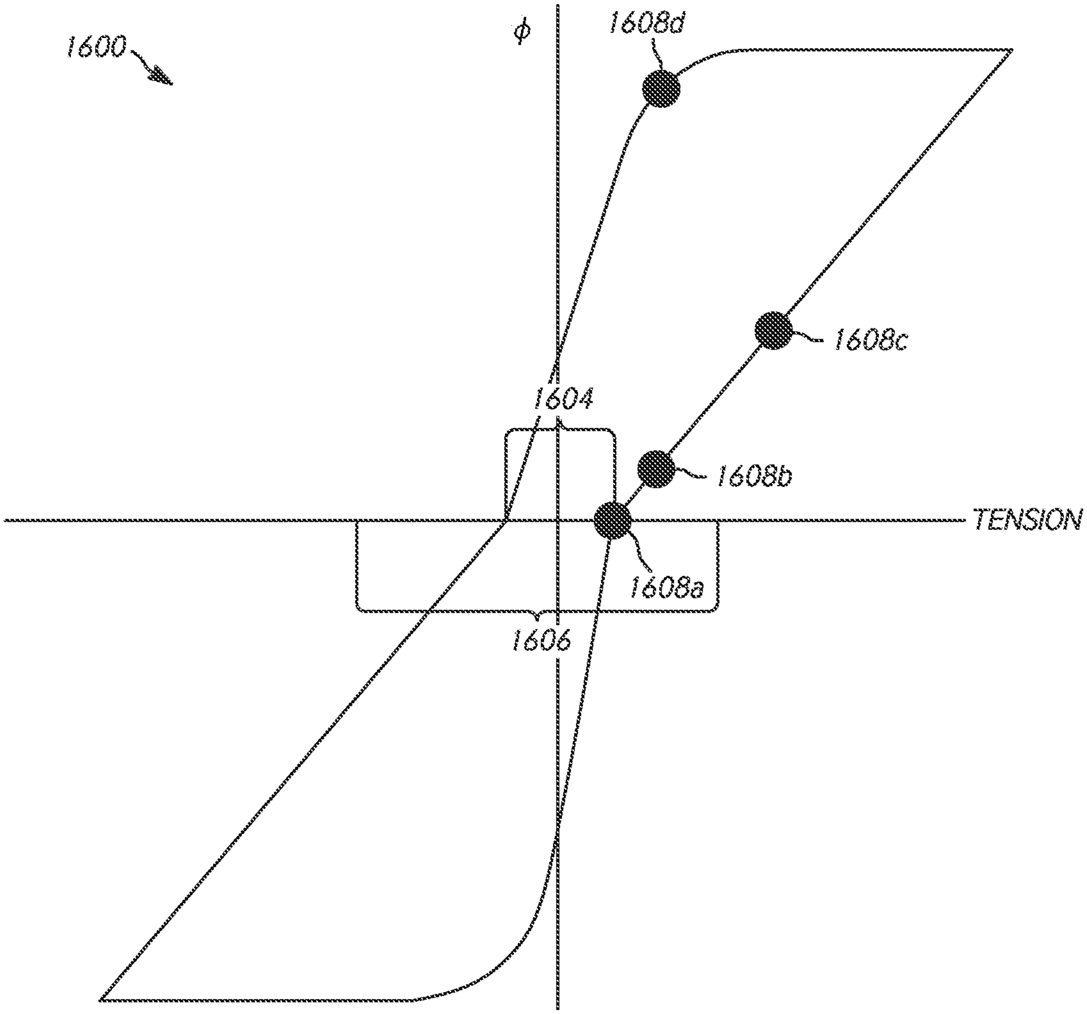
FIG. 16 is an example tension-articulation response plot showing a relationship between pull wire tension and endoscope articulation in accordance with one or more embodiments.

FIG. 16 is an example tension-articulation response plot 1600 showing a relationship between pull wire tension and endoscope articulation in accordance with one or more embodiments. The tension-articulation response plot 1600 is plotted on a plane having an X-axis that represents applied tension on the pull wires and a Y-axis that represents endoscope articulation (denoted $\phi$).

Passive homing algorithm uses the relationship in the tension-articulation response plot 1600 to identify the home position. Assume a dual-wire pulley is at initialization, has a pulley rotation that corresponds to a straightened endoscope (e.g., zero-inclined endoscope), and is then driven in either clockwise or counterclockwise direction. While the pulley is driven within the center dead zone, zero or minimal tension is expected on the pull wires. That is, tension should be at or near the origin of the tension-articulation response plot 1600. When the pulley is further driven, eventually, at least one pull wire becomes taut as the pulley exits (e.g., is driven with a pulley rotation associated with) either edge of the center dead zone. When the pull wire becomes taut, for example, tension may suddenly increase to a first tension point 1608*a*. That is, at the edge of the center dead zone, tension suddenly breaks out from the zero or minimal tension band observed in the center dead zone. A pulley rotation that causes the tension break out corresponds to a pulley rotation at the edge of the center dead zone. The algorithm can set/reset the home position based on the observation that the pulley rotation should correspond to the edge of the center dead zone. The algorithm is described in greater detail in relation to FIG. 17.

Figure 17:
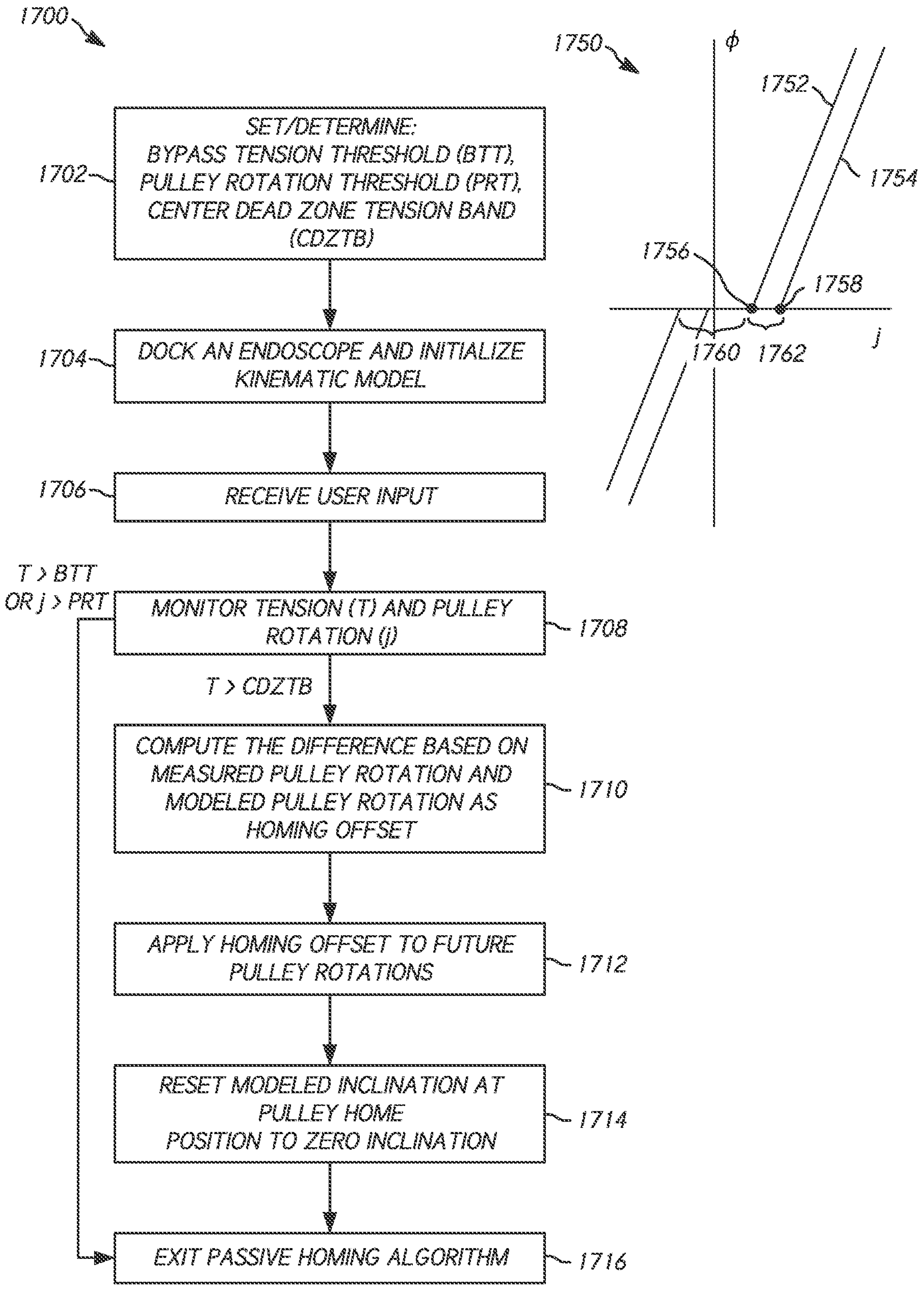
FIG. 17 is a flow diagram for a process of passively homing an endoscope in accordance with one or more embodiments.

FIG. 17 is a flow diagram for a process 1700 of passively homing an endoscope in accordance with one or more embodiments. For example, the process 1700 may be implemented in connection with articulation of an endoscope shaft through robotic control of pull wire tensioning pulleys/mechanisms associated with the endoscope (e.g., incorporated with a handle of the endoscope). The process 1700 may be implemented at least in part by control circuitry of any of the system components disclosed herein, such as a robotic cart/system and/or control tower/system. For the purpose of simplifying below descriptions, the robotic system is selected.

At block 1702, the process 1700 involves setting, receiving, accessing, or otherwise determining one or more threshold levels/values associated with the passive homing algorithm. Such threshold parameters may comprise a bypass tension threshold (BTT) 1606, an allowable pulley rotation threshold (PRT), and/or an allowable center dead zone tension band (CDZTB) 1604. Such parameter(s) may be maintained as global values relevant to one or more endoscope devices, or may be determined/set by the robotic system as process- and/or instrument-specific values, such as specific to a kinematic model of an endoscope device. In some implementations, the process 1700 may involve identifying a particular instrument/endoscope used in the process 1700, such as by a unique identifier or other identification, which may be manually identified and/or input, or may be automatically read/interrogated when the endoscope is docked to the robotic system (e.g., using radio-frequency identification (RFID) or other technology). The system may maintain specifications/parameters associated with various instrument identifiers and the process 1700 may involve accessing such parameters for the particular instrument/endoscope utilized.

At block 1704, the process 1700 involves docking an endoscope and initializing its kinematic model. The endoscope may be docked pre-articulated. The pre-articulation of the endoscope can cause a misalignment between the kinematic model and physical endoscope behavior. The passive homing algorithm can resolve the misalignment partially or completely.

At block 1706, the process 1700 involves receiving a user input commanding a user desired articulation. Such user input may be received via a controller or other user input device, wherein manual (or other) engagement with one or more input mechanisms (e.g., button, joystick, slider, lever, knob, or the like) can generate the command received by the robotic system (e.g., robotic control tower/cart). Subsequent to the receipt of user input, the robotic system begins articulating the endoscope by driving pulley rotation.

At block 1708, the process 1700 involves monitoring tension and pulley rotation. Tension and pulley rotation can be monitored for each time sample or for each sampling period. In some implementations, tension monitoring in connection with block 1706 may be implemented with a lookback window configured to store the monitored tension over time, such as for each time sample. The lookback window may provide a mechanism with which a mean, median, or mode of the monitored tension can be determined to provide a more accurate and/or more reliable measure of tension.

The tension can be compared against the bypass tension threshold (BTT) 1606. If the tension is greater than the bypass tension threshold (BTT) 1606, it may indicate that the endoscope is pre-articulated with a corresponding pulley rotation that has already exited the center dead zone. For example, in the tension-articulation response plot 1600 of FIG. 16, a third tension point 1608*c* is associated with a tension greater in magnitude than the bypass tension threshold (BTT) 1606. In these instances, it may be challenging to determine a tension with which the endoscope exits the center dead zone. Accordingly, the process 1700 can proceed directly to block 1716.

The pulley rotation can be compared against the allowable pulley rotation threshold (PRT). If the pulley rotation is greater than the allowable pulley rotation threshold (PRT), it may indicate that the endoscope is in an undesirable articulation for the homing. For example, in the tension-articulation response plot 1600 of FIG. 16, a second tension point 1608*b* and a fourth tension point 1608*d* are associated with tensions that are smaller in magnitude than the bypass tension threshold (BTT) 1606 and, thus, pass the above described tension condition. However, the tension-articulation response plot 1600 shows a substantial positive articulation at the fourth tension point 1608*d*, indicating that the endoscope is not near the central dead zone and any further articulation is unlikely to find a "break" point that exits the central dead zone. Such substantive articulations, including the articulation at the fourth tension point 1608*d*, can be prevented from undergoing the homing based on a determination that a corresponding pulley rotation is too large to associate the articulation with the central dead zone. For example, the fourth tension point 1608*d* is associated with a pulley rotation near the maximum articulation and at the start of de-articulation, which is associated with a substantially large pulley rotation. The substantially large pulley rotation is greater than the allowable pulley rotation threshold (PRT) and, thus, fails the pulley rotation threshold condition. In contrast, the second tension point 1608*b* is associated with a pulley rotation near the start of articulation, which is associated with a pulley rotation that smaller than the pulley rotation associated with the fourth tension point 1608*d* and could be less than or equal to the allowable pulley rotation threshold (PRT). The passive homing algorithm may be performed from the second tension point 1608*b*. That is, the allowable pulley rotation threshold (PRT) can provide a boundary for potential homing pulley rotations and prevent homing at physically irrelevant pulley rotations. When a pulley rotation is deemed physically irrelevant for the homing, the process 1700 can proceed directly to block 1716.

When both above conditions do not prevent (e.g., do not proceed to block 1716) the robotic system from further performing the passive homing algorithm, monitored tension can be compared against the allowable center dead zone tension band (CDZTB) 1604. If the tension is greater than the allowable center dead zone tension band (CDZTB) 1604, the robotic system has found the "break" point (e.g., the first tension point 1608*a*).

At block 1710, the process 1700 involves computing a homing offset based on a measured pulley rotation at the "break" point and a modelled pulley rotation. Specifically, the homing offset can be computed as the difference between the modelled pulley rotation at an edge of the center dead zone and the measured pulley rotation.

An example articulation response plot 1750 plotted on a plane having an X-axis that represents pulley rotation (denoted j) and a Y-axis that represents endoscope articulation (denoted) is shown as a reference. A center dead zone 1760 is shown on the X-axis. The modelled pulley rotation 1756 at the edge of the center dead zone 1760 is on a modelled response 1752 and the measured pulley rotation 1758 is on physical endoscope behavior 1754. The difference 1762 is the homing offset.

At block 1712, the process 1700 involves applying the homing offset to future pulley rotations. The application of the homing offset can align the modelled response 1752 and the physical endoscope behavior 1754. After the application, the physical endoscope behavior 1754 can have its pulley home position at the center of the center dead zone 1760.

In some implementations, block 1710 and block 1712 involving computation and application of a homing offset may be prevented from another execution until the endoscope is re-docked and its kinematic model is reinitialized. That is, the passive homing is executed once per docking. This prevention may be due to a consideration that, once execution of the block 1712 ensures alignment of the kinematic model, further alignment is not needed unless the endoscope is re-docked and block 1704 is executed. The prevention can involve resetting a flag indicative of an execution of the block 1712 during initialization at block 1704 and setting the flag after execution of this block 1712. The flag can be examined before block 1710 and/or block 1712 to determine whether or not to allow execution of either or both of the blocks.

At block 1714, the process 1700 involves resetting modelled articulation at the measured pulley rotation to an empirically known value. In the example articulation response plot 1750, the empirically known value at its pulley home position can be zero inclination.

At block 1716, the process 1700 involves exiting (e.g., terminating) the passive homing algorithm. In some implementations, if block 1712 has not been executed before reaching this block 1716 (e.g., tension is greater than the bypass tension threshold (BTT) 1606 or a measured pulley rotation is greater than the allowable pulley rotation threshold (PRT)), the passive homing algorithm can be executed again upon receiving another user input at block 1706.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A robotic system comprising:
- an end effector comprising one or more drive outputs configured to cause articulation of an elongate shaft of an instrument coupled to the end effector;
- a processor; and
- a memory storing computer-executable instructions, that when executed, cause the processor to:
  - determine a pulley rotation that, when applied to a pulley coupled to the elongate shaft by the end effector, is expected to relax the elongate shaft to a neutral position;
  - drive the one or more drive outputs based at least in part on the pulley rotation;
  - monitor tension on one or more pull wires coupled to the pulley; and
  - control the one or more drive outputs based at least in part on the tension.

2. The robotic system of claim 1, wherein the pulley is a dual-wire pulley and the pulley rotation is determined based on a kinematic model for the dual-wire pulley.

3. The robotic system of claim 1, wherein:
- the neutral position is a zero degree articulation;
- the instructions further cause the processor to:

determine that the tension is below a minimum tension threshold; and the controlling of the one or more drive outputs includes:

stopping the driving of the one or more drive outputs based on the tension falling below the minimum tension threshold.

4. The robotic system of claim 3, wherein the instructions further cause the processor to:

determine that a magnitude of the tension is increasing; and drive the one or more drive outputs in the opposite direction of the pulley rotation.

5. The robotic system of claim 1, wherein the instructions further cause the processor to:

determine a homing offset; and apply the homing offset to a kinematic model associated with the elongate shaft.

6. The robotic system of claim 5, wherein:

the elongate shaft is docked to the end effector with a non-zero articulation; and the determining of the homing offset includes:

determining the non-zero articulation.

7. The robotic system of claim 6, wherein the determining of the homing offset includes:

determining a point in the kinematic model where the driving of the one or more drive outputs causes the tension to increase for a time period and be greater than a maximum tension during relaxation threshold at an end of the time period.

8. The robotic system of claim 7, wherein the determining of the homing offset is based in part on a difference between the point in the kinematic model and a pulley rotation corresponding to an edge of a center dead zone.

9. The robotic system of claim 1, wherein the instructions further cause the processor to:

receive a relaxation command.

10. A method of robotically articulating an instrument, the method comprising:

determining a pulley rotation that, when applied to a pulley coupled to an elongate shaft by a robotic manipulator, is expected to relax the elongate shaft to a neutral position;

driving one or more drive outputs based at least in part on the pulley rotation;

monitoring tension on one or more pull wires coupled to the pulley; and controlling the driving of the one or more drive outputs based at least in part on the tension.

11. A robotic system comprising:

an end effector comprising one or more drive outputs configured to cause articulation of an elongate shaft of an instrument coupled to the end effector;

a processor; and a memory storing computer-executable instructions, that when executed, cause the processor to:

determine a pulley rotation that, when applied to a pulley coupled to the elongate shaft by the end effector, is expected to articulate the elongate shaft to a desired articulation;

drive the one or more drive outputs based at least in part on the pulley rotation; and during the driving of the one or more drive outputs:

monitor tension on one or more pull wires coupled to the pulley;

determine that the tension is greater than an allowable center dead zone tension band; and perform homing to determine a homing offset.

12. The robotic system of claim 11, wherein the pulley is a dual-wire pulley and the pulley rotation is determined based on a kinematic model for the dual-wire pulley.

13. The robotic system of claim 11, wherein the performing of the homing is based in part on a difference between the pulley rotation when the tension is greater than the allowable center dead zone tension band and a second pulley rotation corresponding to an edge of a center dead zone.

14. The robotic system of claim 13, wherein the performing of the homing is executed during an initial articulation of the elongate shaft.

15. The robotic system of claim 11, wherein the instructions further cause the processor to:

apply the homing offset to a kinematic model associated with the elongate shaft.

16. The robotic system of claim 11, wherein the monitoring of the tension on the one or more pull wires comprises:

sampling the monitored tension over a lookback window; and computing at least one of a mean, a median, or a mode of the monitored tension over the lookback window.

17. The robotic system of claim 11, wherein:

the elongate shaft is docked to the end effector with a non-zero articulation; and the determining of the homing offset includes:

determining the non-zero articulation.

18. The robotic system of claim 11, wherein the instructions further cause the processor to:

determine that the tension is greater than a bypass tension threshold; and terminate the performing of the homing based at least in part on the determining that the tension is greater than the bypass tension threshold.

19. The robotic system of claim 11, wherein the instructions further cause the processor to:

determine that a current pulley rotation is greater than an allowable pulley rotation threshold; and terminate the performing of the homing based at least in part on the determining that the current pulley rotation is greater than the allowable pulley rotation threshold.

20. The robotic system of claim 11, wherein at least one of an allowable center dead zone tension band, a bypass tension threshold, or an allowable pulley rotation threshold is associated with a kinematic model for the elongate shaft.

* * * * *